United States Patent [19]

Branch et al.

[11] Patent Number: 5,504,076
[45] Date of Patent: Apr. 2, 1996

[54] CEPHALOSPORIN COMPOUNDS

[75] Inventors: Clive L. Branch; Angela W. Guest; Richard G. Adams, all of Betchworth, England

[73] Assignee: Pfizer Inc., New York, N.Y.

[21] Appl. No.: 358,965

[22] Filed: Dec. 19, 1994

Related U.S. Application Data

[63] Continuation of Ser. No. 221,656, Apr. 19, 1994, abandoned, which is a continuation of Ser. No. 578,661, Sep. 4, 1990, abandoned.

[30] Foreign Application Priority Data

| Sep. 4, 1989 | [GB] | United Kingdom | 8919945 |
| Sep. 4, 1989 | [GB] | United Kingdom | 8919946 |
| May 8, 1990 | [GB] | United Kingdom | 9010265 |
| May 8, 1990 | [GB] | United Kingdom | 9010299 |

[51] Int. Cl.$^6$ ..................... C07D 501/57; A61K 31/545
[52] U.S. Cl. ............................................. 514/206; 540/225
[58] Field of Search ........................... 514/206; 540/227, 540/225

[56] References Cited

U.S. PATENT DOCUMENTS

| 4,785,090 | 11/1988 | Tsursoka et al. | 540/225 |
| 4,786,633 | 11/1988 | Wagatsuma et al. | 540/225 |
| 4,971,963 | 11/1990 | Sendai et al. | 514/206 |
| 5,008,260 | 4/1991 | Yamauchi et al. | 540/225 |
| 5,173,485 | 12/1992 | Sakane et al. | 540/225 |
| 5,275,816 | 1/1994 | Branch et al. | 424/114 |
| 5,336,673 | 8/1994 | Man et al. | 514/202 |

FOREIGN PATENT DOCUMENTS

| 01537099 | 9/1985 | European Pat. Off. . |
| 024865 | 6/1987 | European Pat. Off. . |

OTHER PUBLICATIONS

Journal of Heterocyclic Chemistry, vol. 11, No. 4, Aug. 1974, Action of Amines and Carbonyl Reagents on 3,5–Diphenyl–4–pyrone and its Thio . . . pp. 487–490.
Bulletin of the chemical Society of Japan, vol. 51, 1978, Reactions of 4H–Pyran–4–thiones with Ammonia, Hydrazine and Guanidine, pp. 179–181.
Journal of the Chemical Society, 1977, Preparation of NN'–Linked Bi(heteroaryls) from Dehydroacetic Acid and 2, 6–Dimethyl–4–pyrone, pp. 1428–1436.

*Primary Examiner*—Nicholas Rizzo
*Attorney, Agent, or Firm*—Peter C. Richardson; Paul H. Ginsburg; Lorraine B. Ling

[57] ABSTRACT

7β-[2-(aminothiazolyl and thiadiazolyl)-2-oxyiminoacetamido] cephalosporin derivatives having a 3-[N-(optionally substituted) aminopyridiniumthiomethyl] substituent have antibacterial activity and are of use in antibacterial therapy. Processes for the preparation of such cephalosporins plus intermediates for use in the preparation thereof, including N-(optionally substituted)amino-thiopyridones, are also described.

27 Claims, No Drawings

CEPHALOSPORIN COMPOUNDS

This application is a continuation of Ser. No. 08/221,656 filed Apr. 1, 1994, abandoned, which is a continuation of Ser. No. 07/578,661 filed Sep. 4, 1990, abandoned.

This invention relates to novel β-lactam containing compounds, in particular to a novel class of cephalosporin derivatives, their preparation and their use. These compounds have antibacterial properties and are therefore of use in the treatment of bacterial infections in humans and animals caused by a wide range of organisms.

7β-[2-(2-amino-4-thiazolyl)-2-oxyiminoacetamido] cephalosporin derivatives have been reported, of which a particular subgroup are those comprising at the 3-position a substituent —CH$_2$S-Het in which 'Het' is an optionally substituted heterocyclic group. EP-A-0 248 645 (Tanabe Seiyaku) discloses inter alia a class of such compounds in which 'Het' is a pyridinium ring (bonded through a ring carbon atom), optionally substituted on the pyridinium nitrogen by acylamino and exemplified by an N-acetyl derivative, in combination with a [2-oxopyrrolidin-3-yl]-oxyimino substituent.

In addition, EP-A-0 153 709 (Meiji Seika Kaisha) discloses generically another class of such compounds wherein 'Het' is a bicyclic heterocyclic system comprising a pyridinium ring (bonded through a ring carbon atom) fused to a carbocyclic ring and which may be substituted on the pyridinium nitrogen by an amino group, optionally substituted by alkyl. No exemplification thereof is however provided.

It has now been found that the range of substituents that can be accommodated on the pyridinium nitrogen may be substantially expanded, to give a class of cephalosporin derivatives that possess high antibacterial activity.

Accordingly, the present invention provides a compound of formula (I) or a salt thereof:

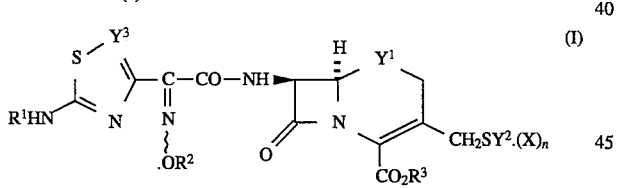

wherein:

Y$^1$ is oxygen, sulphur, —SO—, —SO$_2$— or CH$_2$;

R$^1$ is hydrogen or an amino protecting group;

R$^2$ is (C$_{1-12}$)alkyl, (C$_{2-12}$)alkenyl, (C$_{2-12}$)alkynyl, (C$_{3-7}$)cycloalkyl, (C$_{5-8}$)cycloalkenyl, each of which may be optionally substituted, hydrogen or aryl;

CO$_2$R$^3$ is carboxy or a carboxylate anion, or the group R$^3$ is a readily removable carboxy protecting group;

Y$^2$ is a group of the formula:

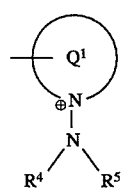

in which the moiety:

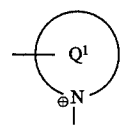

hereinafter referred to as the ring Q$^1$ is a pyridinium group which is bonded to sulphur via a ring carbon atom and which is optionally substituted at a ring carbon available for substitution by up to four substituents, two of which may be linked to form the residue of a heterocyclic or carbocyclic ring; R$^4$ and R$^5$ which may be the same or different are selected from hydrogen, a group R$^6$, formyl, a group —COR$^6$, a group —COR$^7$, a group —SO$_2$R$^6$, or a readily removable amino protecting group, in which R$^6$ is (C$_{1-6}$)alkyl, (C$_{3-7}$)cycloalkyl, (C$_{2-6}$)alkenyl, (C$_{5-8}$)cycloalkenyl, (C$_{2-6}$)alkynyl, each of which may be optionally substituted, aryl or heterocyclyl, and R$^7$ is a group —OR$^6$, amino, a group —NHR$^6$ or a group —NR$^6$R$^6$ (which two R$^6$ may be the same or different); or R$^4$ and R$^5$ together with the nitrogen atom to which they are attached form an amidine or heterocyclic group; or R$^4$ and R$^5$ together form a (C$_{1-6}$)alkylidene, (C$_{3-7}$)cycloalkylidene, aryl(C$_{1-6}$)alkylidene or heteroaryl(C$_{1-6}$)alkylidene group, optionally substituted in the alkylidene or cycloalkylidene moiety;

Y$^3$ is nitrogen or CH;

X is an inorganic or organic anion; and n is 0 or 1, with the proviso that when: (i) CO$_2$R$^3$ is carboxylate, n is 0, and (ii) CO$_2$R$^3$ is carboxy or the group R$^3$ is a readily removable carboxy protecting group, then n is 1 and the anion X is present in the appropriate stoichiometric proportion to balance the positive charge on the pyridinium group.

Examples of the group Y$^2$ include, for example, groups of the formulae (a), (b), and (c):

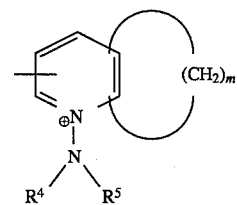

(a)

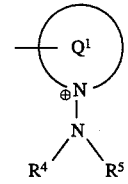

(b)

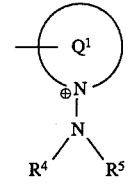

(c)

in which:

in formula (a), the pyridinium ring is bonded to sulphur via a ring carbon atom, m is an integer from 3 to 5, and R$^4$ and R$^5$ which may be the same or different are hydrogen, or optionally substituted (C$_{1-6}$)alkyl;

in formula (b), the ring Q$^1$ is as hereinbefore defined (with the proviso that two substituents together do not form a residue —$(CH_2)_m$— wherein m is as hereinbefore defined), and $R^4$ and $R^5$ which may be the same or different are hydrogen or optionally substituted $(C_{1-6})$alkyl; and in formula (c), ring $Q^1$ is as hereinbefore defined, $R^4$ is hydrogen or optionally substituted $(C_{1-6})$alkyl and $R^5$ is $(C_{3-7})$cycloalkyl, $(C_{2-6})$alkenyl, $(C_{5-8})$cycloalkenyl, $(C_{2-6})$alkynyl, each of which may be optionally substituted, aryl or heterocyclyl; or $R^4$ and $R^5$ are independently selected from $(C_{3-7})$cycloalkyl, $(C_{2-6})$alkenyl, $(C_{5-8})$cycloalkenyl, $(C_{2-6})$alkynyl, each of which may be optionally substituted, aryl, heterocyclyl, or a readily removable amino protecting group; or $R^4$ is —$COR^8$ or —$SO_2R^9$ and $R^5$ is hydrogen, or $R^4$ is formyl, —$COR^8$, —$SO_2R^9$, or —$COR^{10}$ and $R^5$ is formyl, —$COR^8$, —$SO_2R^9$, $R^9$, or —$COR^{10}$, in which $R^8$ is —$OR^9$, —$NH_2$, —$NHR^9$, —$NR^9R^9$ (which two $R^9$ may be the same or different) or $R^{11}$, $R^9$ is $R^{10}$ or $R^{11}$, $R^{10}$ is optionally substituted $(C_{1-6})$alkyl, and $R^{11}$ is $(C_{3-7})$cycloalkyl, $(C_{5-8})$cycloalkenyl, $(C_{2-6})$alkenyl, $(C_{2-6})$alkynyl, each of which may be optionally substituted, aryl or heterocyclyl; or $R^4$ and $R^5$ together with the nitrogen atom to which they are attached form an amidine or heterocyclic group; or $R^4$ and $R^5$ together form a $(C_{1-6})$alkylidene, $(C_{3-7})$cycloalkylidene, aryl$(C_{1-6})$alkylidene or heteroaryl$(C_{1-6})$alkylidene group, optionally substituted in the alkylidene or cycloalkylidene moiety.

It will be appreciated that the compounds of formula (I) are quaternary salts and the positive charge on the pyridinium group must always be balanced by a counter anion. The counter anion may be present on a negatively charged group within the molecule, such as the carboxylate anion $CO_2R^3$ (when n is 0), or the counter anion may be present as an external anion X (when n is 1).

It will be further appreciated that one or more chiral centres may be present in the compound of formula (I), for example in the oxime etherifying group. The invention includes within its scope the individual R and S forms at each chiral centre as well as mixtures thereof.

Suitable $(C_{1-12})$alkyl groups include straight and branched chain alkyl groups containing 1 to 12 carbon atoms. Preferred alkyl groups contain 1 to 6 carbon atoms, such as methyl, or ethyl.

Suitable $(C_{2-12})$alkenyl groups include straight and branched chain alkenyl groups containing 2 to 12 carbon atoms. Preferred alkenyl groups contain 2 to 6 carbon atoms, such as propenyl and butenyl.

Suitable $(C_{2-12})$alkynyl groups include straight and branched chain alkynyl groups containing 2 to 12 carbon atoms. Preferred alkynyl groups contain 2 to 6 carbon atoms such as propynyl and butynyl.

Suitable $(C_{3-7})$cycloalkyl groups include cyclopropyl, cyclopentyl, and cyclohexyl.

Suitable $(C_{5-8})$cycloalkenyl groups include cyclopentenyl and cyclohexenyl.

When used herein the term 'aryl' includes phenyl and naphthyl each optionally substituted with up to five, preferably up to three groups.

When used herein the terms 'heterocyclyl' and 'heterocyclic' suitably include, unless otherwise defined, aromatic and non-aromatic, single and fused, rings suitably containing up to four heteroatoms in each ring selected from oxygen, nitrogen and sulphur, which rings may be unsubstituted or substituted by, for example, up to three groups. Each heterocyclic ring suitably has from 4 to 7, preferably 5 or 6, ring atoms. A fused heterocyclic ring system may include carbocyclic rings and need include only one heterocyclic ring.

Some examples of optional substituents in groups for instance alkyl, cycloalkyl, alkenyl, cycloalkenyl, alkynyl, alkylidene, cycloalkylidene, amidine, pyridinium, ring $Q^1$, aryl or heterocyclyl, mentioned hereinbefore as being optionally substituted, include, unless otherwise defined, up to three groups (which may be the same or different) chosen from:

(i) halogen, cyano, azido, nitro, phthalimido, formyl, carboxy, carboxylate salts, sulphonyl, sulphonate salts, or oxo;

(ii) amino, hydrazino, guanidino, carbamoyl, or sulphonamido, in each of which groups a nitrogen may be further optionally substituted by one or two groups (which may be the same or different) selected from the groups listed in subparagraphs (iv), (v) and (vi);

(iii) hydroxy, oxyimino, or mercapto, in each of which groups hydrogen may be replaced by one of the groups listed in subparagraphs (iv), (v) and (vi);

(iv) a group $R^p$ wherein $R^p$ denotes aryl, or heterocyclyl;

(v) a group $R^p$ wherein $R^q$ denotes $(C_{1-6})$alkyl, $(C_{3-7})$cycloalkyl, $(C_{2-6})$alkenyl, $(C_{5-8})$ cycloalkenyl, or $(C_{2-6})$alkynyl, each of which may be further optionally substituted by up to three groups (which may be the same or different) chosen from the groups listed in subparagraphs (i), (ii), (iii), (iv) and (vi); and (vi) a group $R^pCO$—, $R^pOCO$—, $R^qCO$—, $R^qOCO$—, $R^pSO$—, $R^pSO_2$—, $R^qSO$—, or $R^qSO_2$— wherein $R^p$ and $R^q$ are as defined in subparagraphs (iv) and (v) respectively.

When used herein, the term 'halogen' refers to fluorine, chlorine, bromine and iodine.

Preferably a substituent which may be present on those groups $R^2$ defined hereinabove as being optionally substituted is selected from carboxyl, esterified carboxy, hydroxy, alkoxy, cyano, carbamoyl, N-substituted carbamoyl, aryloxy, aralkoxy, mercapto, alkylthio, arylthio, amino, substituted amino, halogen, nitro, azido, formyl, acyl, acyloxy, phthalimido, acylamino, alkoxycarbonylamino, aralkoxycarbonylamino, aryl and heterocyclyl.

Preferably a substituent for an alkyl, cycloalkyl, alkenyl, cycloalkenyl, alkylidene, cycloalkylidene, alkynyl or amidine group is selected from halogen, cyano, azido, nitro, carboxy, $(C_{1-6})$alkoxycarbonyl, carbamoyl, mono- or di-$(C_{1-6})$alkylcarbamoyl, sulphono, sulphamoyl, mono- and di-$(C_{1-6})$alkylsulphamoyl, amino, mono- and di-$(C_{1-6})$alkylamino, acylamino, $(C_{1-6})$alkoxycarbonyl amino, aryl, heterocyclyl, hydroxy, $(C_{1-6})$alkoxy, acyloxy, oxo, arylcarbonyl, heterocyclylcarbonyl, $(C_{1-6})$alkylthio, $(C_{1-6})$alkanesulphinyl, and $(C_{1-6})$alkanesulphonyl.

Preferably a substituent for an aryl group is selected from halogen, $(C_{1-6})$alkyl, phenyl, $(C_{1-6})$alkoxy, hydroxy$(C_{1-6})$alkyl, mercapto$(C_{1-6})$alkyl, halo$(C_{1-6})$alkyl, mercapto, hydroxy, amino, mono- or di-$(C_{1-6})$alkylamino, nitro, carboxy, $(C_{1-6})$alkoxycarbonyl, $(C_{1-6})$alkoxycarbonyl$(C_{1-6})$alkyl, $(C_{1-6})$alkylcarbonyloxy, formyl, and $(C_{1-6})$alkylcarbonyl.

Preferably a substituent for a heterocyclyl group, including a pyridinium group, or the ring $Q^1$ is selected from halogen, $(C_{1-6})$alkyl, $(C_{1-6})$alkoxy, $(C_{1-6})$alkoxy$(C_{1-6})$alkyl, halo$(C_{1-6})$alkyl, hydroxy, amino, mono- and di-$(C_{1-6})$alkylamino, acylamino, carboxy, carboxy salts, carboxy esters, carbamoyl, $(C_{1-6})$alkoxycarbonyl, aryloxycarbonyl, $(C_{1-6})$alkoxycarbonyl$(C_{1-6})$alkyl, aryl, and oxo groups.

Suitable amino protecting groups $R^1$, $R^4$ or $R^5$ are those well known in the art and which may be removed under conventional conditions without disruption of the remainder of the molecule. A comprehensive discussion of the ways in which amino groups may be protected and methods for cleaving the resulting protected derivatives is given in, for example, 'Protective Groups in Organic Synthesis' by T. W. Greene (Wiley-Interscience, New York, 1981). Particularly suitable protecting groups include, for example, amides and carbamates.

Examples of such amino protecting groups include $(C_{1-6})$ alkanoyl; benzoyl; benzyl optionally substituted in the phenyl ring by one or two substituents selected from $(C_{1-4})$alkyl, $(C_{1-4})$alkoxy, trifluoromethyl, halogen, or nitro; $(C_{1-4})$alkoxycarbonyl; benzyloxycarbonyl or trityl substituted as for benzyl above; allyloxycarbonyl, trichloroethoxycarbonyl or chloroacetyl.

Suitable groups for $R^2$ include, for example, hydrogen, optionally substituted $(C_{1-6})$alkyl and optionally substituted $(C_{3-7})$cycloalkyl.

Preferably the group for $R^2$ is methyl, optionally substituted by aryl, and optionally further substituted by carboxy. A suitable aryl group is 3,4-dihydroxyphenyl, optionally substituted by carboxy.

Specific examples of the group $R^2$ include hydrogen, methyl, 1-carboxy-1-methylethyl, cyclopentyl, ethyl, carboxy(3,4-dihydroxyphenyl)methyl and (methylenedioxy)benzyl, of which carboxy (3,4-dihydroxyphenyl)methyl is particularly preferred.

Suitable groups of $R^4$ and $R^5$ include, for example, $(C_{1-6})$alkyl, $(C_{3-7})$cycloalkyl, $(C_{3-7})$cycloalkyl$(C_{1-6})$alkyl, $(C_{2-6})$alkenyl, $(C_{2-7})$alkynyl, each of which may be optionally substituted, hydrogen, heterocyclyl, optionally substituted $(C_{1-6})$alkyl carbonyl, carbamoyl, optionally substituted $(C_{1-6})$alkylcarbamoyl, arylcarbonyl, and heterocyclylcarbonyl, or $R^4$ or $R^5$ may together form an optionally substituted $(C_{1-6})$alkylidene group or $R^4$ or $R^5$ may together with the nitrogen to which they are attached form a heterocyclic group.

Specific examples of the groups $R^4$ and $R^5$ include hydrogen, methyl, ethyl, carboxymethyl, methoxyethyl, cyanomethyl, propargyl, 4-carboxy-butan-1-yl, 2-amino-2-(methoxycarbonyl)ethyl, cyclopropylmethyl, propyl, cyclopentyl, prop-2-en-1-yl, butyl, hexyl, isopropyl, 2-hydroxyethyl, pyridyl, isoxazolylmethyl, thiazolylmethyl, chloropyridinyl, pyrazinyl, imidazolinyl, benzopyrazidinyl, acetyl, benzoyl, 3,4-dihydroxybenzoyl, 4-nitrobenzoyl, 4-methoxybenzoyl, 4-carboxybenzoyl, 4-aminobenzoyl, 2-furanoyl, 3,4-dihydroxycinnamoyl, carbamoyl and N-methylcarbamoyl. Specific examples of $R^4$ and $R^5$ together forming a $(C_{1-6})$alkylidene group include propylidene.

Specific examples of the groups $R^4$ and $R^5$ together with the nitrogen to which they are attached forming an optionally substituted heterocyclic group include piperazinyl, triazolyl, pyrrolidinyl and piperidinyl. Suitable values for the groups $R^4$ and $R^5$, when acting as a readily removable protecting group include amides and carbamates, for instance t-butoxycarbonyl.

Suitable substituents for the pyridinium group of the ring Q include $(C_{1-6})$alkoxy, for instance, methoxy and $(C_{1-6})$alkyl, for instance methyl. In the instance when two such substituents are linked to form the residue of a carbocyclic ring, this may be provided by an optionally substituted $(C_{1-6})$alkylene group, for instance a propylene group such that $Y^2$ is 2,3-cyclopentenopyridinium.

Included within the scope of readily removable carboxy protecting groups for $R^3$ are, for example, ester groups including pharmaceutically acceptable in vivo hydrolysable ester groups.

Compounds of the invention may exist in two or more tautomeric forms, e.g. those having the partial structures below:

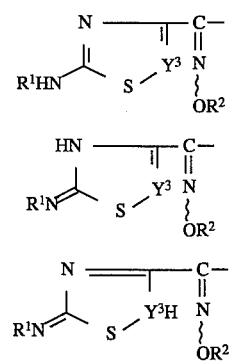

Compounds of the present invention may exist as either syn or anti isomers, or may exist as mixtures of syn and anti isomers containing at least 75% of one such isomer, or preferably at least 90% of one such isomer.

When used herein, the terms syn and anti refer to the configuration of the group $OR^2$ with respect to the carboxamido group, the syn-configuration (sometimes called the Z-configuration) being denoted thus:

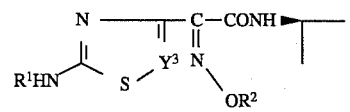

and the anti configuration (sometimes called the E-configuration ) being denoted thus:

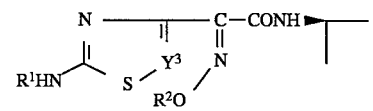

Preferred compounds of the present invention are the syn-isomers, the compounds of formula (II):

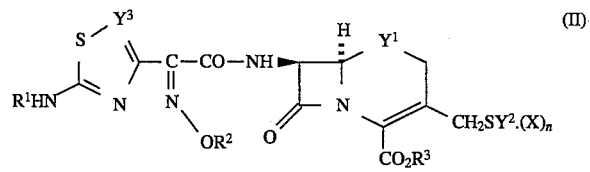

wherein $R^1$, $R^2$, $R^3$, X, $Y^1$, $Y^2$, $Y^3$ and n are as hereinbefore defined.

It will be appreciated that also included within the scope of the invention are salts and carboxy-protected derivatives, including in vivo hydrolysable esters, of any carboxy groups that may be present as optional substitutents in compounds of formula (I). Also included within the scope of the invention are acid addition salts of any amino or substituted amino groups that may be present as optional substituents in compounds of formula (I).

It will be appreciated that, in the group $Y^2$, the pyridinium ring may be bonded to sulphur by a ring carbon atom which is α-, β- or γ-, preferably α- or γ-, more preferably γ-, to the pyridinium nitrogen.

Since the β-lactam antibiotic compounds of the present invention are intended for use in pharmaceutical compositions, it will be readily appreciated that preferred compounds within formula (I) are pharmaceutically acceptable, i.e. are compounds of formula (Ia) or pharmaceutically acceptable salts or pharmaceutically acceptable in vivo hydrolysable esters thereof:

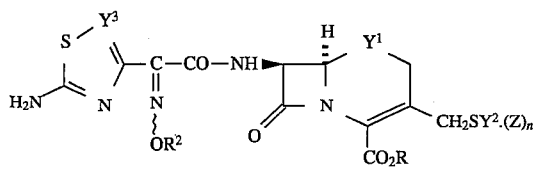

(Ia)

wherein $R^2$, $Y^1$, $Y^2$, $Y^3$ and n are as hereinbefore defined (with the proviso that $R^4$ or $R^5$ is not a readily removable amino protecting group), the group $CO_2R$ is carboxy or a carboxylate anion and Z is a pharmaceutically acceptable inorganic or organic anion present in the appropriate stoichiometric proportion to balance the positive charge on the pyridinium ring of the group $Y^2$.

Suitable values of Z include chloride, bromide, iodide, phosphate (i.e. ⅓ $PO_4^{3-}$), and sulphate (i.e. ½ $SO_4^{2-}$), when the anion is an inorganic anion; and acetate, hydrogen maleate, methyl sulphonate, dihydrogen citrate, and hydrogen fumarate when the anion is an organic anion.

Non-pharmaceutically acceptable salts of the compound of formula (I) wherein $R^3$ is hydrogen are primarily of use as intermediates in the preparation of a compound of formula (I) wherein $R^3$ is hydrogen or a pharmaceutically acceptable salt thereof.

Salts within compounds of formula (I) may be prepared by salt exchange in conventional manner.

Similarly, carboxy-protected derivatives of formula (I), i.e. those compounds of formula (I) wherein $R^3$ is a readily removable carboxy protecting group, may be used as intermediates in the preparation of a compound of the formula (I) wherein $R^3$ is hydrogen, or a pharmaceutically acceptable salt thereof. Included within the scope of readily removable carboxy protecting groups for $R^3$ are ester groups including pharmaceutically acceptable in vivo hydrolysable ester groups.

From the foregoing, it will be appreciated that within the compounds of the formula (Ia) there exists a sub-group of compounds of the formula (Ib):

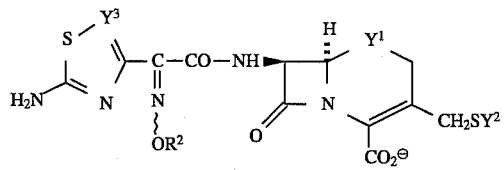

(Ib)

wherein $R^2$, $Y^1$, $Y^2$, and $Y^3$ are defined with respect to formula (Ia);
which compounds of formula (Ib) may also be described as betaines, a betaine being defined as an uncharged species having isolated non-adjacent cationic and anionic sites, and not possessing a hydrogen atom bonded to the cationic site.

There also exists within the compounds of formula (Ia) a second sub-group, the compounds of the formula (Ic):

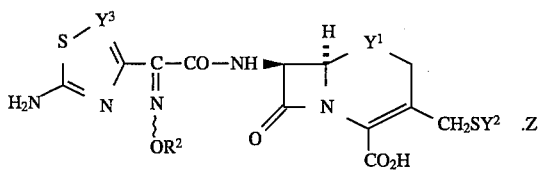

(Ic)

wherein $R^2$, $Y^1$, $Y^2$, $Y^3$, and Z are defined with respect to formula (Ia).

Since the β-lactam antibiotic compounds of the present invention are intended for use in pharmaceutical compositions, it will be further understood that they are each provided in substantially pure form, for example at least 50% pure, more suitably at least 75% pure and preferably at least 95% pure (% are on a wt/wt basis). Impure preparations of the compounds may be used for preparing the more pure forms used in the pharmaceutical compositions. Although the purity of intermediate compounds of the present invention is less critical, it will readily be understood that the substantially pure form is preferred as for the β-lactam antibiotic compounds. Preferably, whenever possible, the compounds of the present invention are obtained in crystalline form.

When some of the compounds of this invention are allowed to crystallise, or are recrystallised, from organic solvents, solvent of crystallisation may be present in the crystalline product. This invention includes within its scope such solvates. Similarly, some of the compounds of this invention may be crystallised or recrystallised from solvents containing water. In such cases water of hydration may be formed. This invention includes within its scope stoichiometric hydrates as well as compounds containing variable amounts of water that may be produced by processes such as lyophilisation.

Suitable readily removable carboxyl protecting groups for the group $—CO_2R^3$ include groups forming ester derivatives of the carboxylic acid, including in vivo hydrolysable esters. The derivative is preferably one which may readily be cleaved.

Suitable ester-forming carboxyl-protecting groups are those which may be removed under conventional conditions. Such groups for $R^3$ include benzyl, p-methoxybenzyl, benzoylmethyl, p-nitrobenzyl, 4-pyridylmethyl, 2,2,2-trichloroethyl, 2,2,2-tribromoethyl, t-butyl, t-amyl, allyl, diphenylmethyl, triphenylmethyl, adamantyl, 2-benzyloxyphenyl, 4-methylthiophenyl, tetrahydrofuran-2-yl, tetrahydropyran-2-yl, pentachlorophenyl, acetonyl, p-toluenesulphonylethyl, methoxymethyl, a silyl, stannyl or phosphorus-containing group, an oxime radical of formula $—N{=}CHR^{12}$ where $R^{12}$ is aryl or heterocyclic, or an in vivo hydrolysable ester radical such as defined below.

A carboxyl group may be regenerated from any of the above esters by usual methods appropriate to the particular $R^3$ group, for example, acid- and base-catalysed hydrolysis, or by enzymically-catalysed hydrolysis, or by hydrogenolysis under conditions wherein the remainder of the molecule is substantially unaffected.

Examples of suitable pharmaceutically acceptable in vivo hydrolysable ester groups include those which break down readily in the human body to leave the parent acid or its salt. Suitable ester groups of this type include those of part formula (i), (ii), (iii) and (iv):

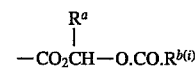

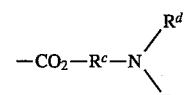
(ii)

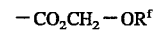
(iii)

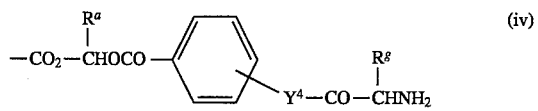
(iv)

wherein $R^a$ is hydrogen, $(C_{1-6})$alkyl, $(C_{3-7})$cycloalkyl, methyl, or phenyl; $R^b$ is $(C_{1-6})$alkyl, $(C_{1-6})$alkoxy, phenyl, benzyl, $(C_{3-7})$cycloalkyl, $(C_{1-6})$alkyl$(C_{3-7})$cycloalkyl, 1-amino$(C_{1-6})$alkyl, or 1-$(C_{1-6}$alkyl)-amino$(C_{1-6})$alkyl; or $R^a$ and $R^b$ together form a 1,2-phenylene group optionally substituted by one or two methoxy groups; $R^c$ is $(C_{1-}$ $_6$)alkylene optionally substituted with a methyl or ethyl group and $R^d$ and $R^e$ independently are $(C_{1-6})$alkyl; $R^f$ represents $(C_{1-6})$alkyl; $R^g$ is hydrogen or phenyl optionally substituted by up to three groups selected from halogen, $(C_{1-6})$-alkyl, or $(C_{1-6})$alkoxy; and $Y^4$ is oxygen or NH.

Examples of suitable pharmaceutically acceptable in vivo hydrolysable ester groups include, for example, acyloxyalkyl groups such as acetoxymethyl, pivaloyloxymethyl, α-acetoxyethyl, α-pivaloyloxyethyl, 1-(cyclohexylcarbonyloxy)prop-1-yl, and (1-aminoethyl)carbonyloxymethyl; alkoxycarbonyloxyalkyl groups, such as ethoxycarbonyloxymethyl and α-ethoxycarbonyloxyethyl; dialkylaminoalkyl especially di-loweralkylamino alkyl groups such as dimethylaminomethyl, dimethylaminoethyl, diethylaminomethyl or diethylaminoethyl; lactone groups such as phthalidyl and dimethoxyphthalidyl; and esters linked to a second β-lactam antibiotic or to a β-lactamase inhibitor.

A further suitable pharmaceutically acceptable in vivo hydrolysable ester group is that of the formula:

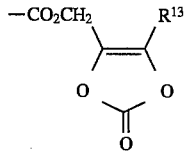

wherein $R^{13}$ is hydrogen, $(C_{1-6})$alkyl or phenyl.

Suitable pharmaceutically acceptable salts of the carboxy group of the compound of formula (I) include metal salts, for example aluminium, alkali metal salts such as sodium or potassium, alkaline earth metal salts such as calcium or magnesium; and ammonium or substituted ammonium salts, for example those with lower alkylamines such as triethylamine, hydroxy-lower alkylamines such as 2-hydroxyethylamine, bis-(2-hydroxyethyl)-amine or tris-(2-hydroxyethyl)amine, cycloalkylamines such as dicyclohexylamine, or with procaine, dibenzylamine, N,N-dibenzylethylenediamine, 1-ephenamine, N-methylmorpholine, N-ethylpiperidine, N-benzyl-β-phenethylamine, dehydroabietylamine, N,N'-bisdehydro-abietylamine, ethylenediamine or N-methylglucosamine; or basic amino acids such as lysine, arginine, or bases of the pyridine type such as pyridine, collidine or quinoline; or other amines which have been used to form salts with known penicillins and cephalosporins. Other useful salts include the lithium salt and silver salt.

Specific classes of compounds within compounds of formulae (I), (Ia), (Ib), Ic) and (II) as hereinbefore defined are those compounds in which $Y^1$ is sulphur or sulphoxide.

Specific compounds within this invention include the following and pharmaceutically acceptable salts and in-vivo hydrolysable esters thereof:

[6R,7R]-7-[2-(2-Amino-4-thiazolyl)-2-(Z)-(methoxyimino)acetamido] -3-[1-(dimethylamino)pyridinium- 4-thiomethyl]-ceph-3-em-4-carboxylate;

[6R, 7R]-7-[2-(2-Amino-4-thiazolyl)-2-(Z)-(methoxyimino)acetamido] -3-[1-(methylamino) pyridinium-4-thiomethyl]ceph-3-em-4-carboxylate;

[6R, 7R]-7-[2-(2-Amino-4-thiazolyl)-2-(Z)-(1 -carboxy-1-methylethoxyimino)acetamido]-3-[1 -(methylamino) pyridinium-4-thiomethyl]ceph-3 -em-4-carboxylate;

[6R,7R]-3-(1-Aminopyridinium-4-thiomethyl)-7-[2-(2 -amino-4-thiazolyl)-2-(Z)-(methoxyimino)acetamido] ceph- 3-em-4-carboxylate;

[6R,7R]-[2-(2-Amino-4-thiazolyl)-2-(Z)-(methoxyimino)acetamido] -3-[1-(carboxymethylamino)pyridinium-4 -thiomethyl]ceph-3-em-4-carboxylate;

[6R, 7R]-7-[2-(2-Amino-4-thiazolyl)-2-(Z)-(methoxyimino) acetamido]-3-[1-(ethylamino)pyridinium-4-thiomethyl] ceph-3-em-4-carboxylate;

[6R, 7R]-[2-(2-Amino-4-thiazolyl)-2-(Z)-(methoxyimino)acetamido] -3-[1-[4-(2-hydroxyethyl)piperazin-1-yl] pyridinium-4-thiomethyl]ceph-3-em-4-carboxylate;

[6R, 7R]-7-[2-(2-Amino-4-thiazolyl)-2-(Z)-(cyclopentyloxyimino)acetamido] -3-[1-(methylamino)pyridinium-4-thiomethyl]ceph-3-em-4-carboxylate;

[6R,7R]-7-[2-(2-Amino-4-thiazolyl)-2-(Z)-(hydroxyimino) acetamido]-3-[1-(methylamino)pyridinium-4-thiomethyl] ceph-3-em-4-carboxylate;

[6R, 7R]-7-[2-(2-Amino-4-thiazolyl)-2-(Z)-(methoxyimino) acetamido]-3-[1-(4-carboxybutan-1-yl)aminopyridinium-4 -thiomethyl]ceph-3-em-4-carboxylate;

[6R, 7R]-7-[2-(2-Amino-4-thiazolyl)-2-(Z)-(ethoxyimino) acetamido]-3-[1-(methylamino)pyridinium-4-thiomethyl] ceph-3-em-4-carboxylate;

[6R,7R]-3-[1-[(2S)-2-Amino-2-(methoxycarbonyl)ethylamino] pyridinium-4-thiomethyl]-7-[2-(2-amino-4 -thiazolyl)-2-(Z)-(methoxyimino)acetamido]ceph-3-em-4 -carboxylate;

[6R, 7R]-7-[2-(2-Amino-4-thiazolyl)-2-(Z)-(methoxyimino) acetamido]-3-[1-(cyclopropylmethylamino)pyridinium-4 -thiomethyl]ceph-3-em-4-carboxylate;

[6R,7R]-3-(1-Aminopyridinium-4-thiomethyl)-7-[2-amino-4-thiazolyl)-2-(Z)-(methoxyimino)acetamido]ceph-3-em-4 -carboxylate;

[6R,7R]-7-[2-(2-Amino-4-thiazolyl)-2-(Z)-(methoxyimino)acetamido] -3-[1-(isopropylidineamino)pyridinium-4 -thiomethyl]ceph-3-em-4-carboxylate;

[6R,7R]-7-[2-(2-Amino-4-thiazolyl)-2-(Z)-(methoxyimino) acetamido]-3-[1-(propylamino)pyridinium-4-thiomethyl] ceph-3-em-4-carboxylate;

[6R,7R]-7-[2-(2-Amino-4-thiazolyl)-2-(Z)-(methoxyimino)acetamido] -3-[1-(cyclopentylamino)pyridinium-4 -thiomethyl]ceph-3-em-4-carboxylate;

[6R, 7R]-7-[2-(2-Amino-4-thiazolyl)-2-(Z)-(methoxyimino)acetamido] -3-[1-(prop-2-en-1-yl)aminopyridinium-4-thiomethyl]ceph-3-em-4-carboxylate;

[6R, 7R]-7-[2-(2-Amino-4-thiazolyl)-2-(Z)-(methoxyimino)acetamido] -3-[1-butylaminopyridinium-4-thiomethyl] ceph-3-em-4-carboxylate;

[6R, 7R]-7-[2-(2-Amino-4-thiazolyl)-2-(Z) (methoxyimino) acetamido]-3-[1-(hexylamino)pyridinium-4-thiomethyl] ceph-3-em-4-carboxylate;

[6R,7R]-7-[2-(2-Amino-4-thiazolyl)-2-(Z)-(methoxyimino) acetamido]-3-[1-(1-isopropyl)aminopyridinium-4-thiomethyl] ceph-3-em-4-carboxylate;

[6R, 7R]-7-[2-(2-Amino-4-thiazolyl)-2-(Z)-(methoxyimino) acetamido]-3-[1-[(2-hydroxyethyl)amino]pyridinium-4 -thiomethyl]ceph-3-em-4-carboxylate;

[6R,7R]-7-[2-(2-Amino-4-thiazolyl)-2-(Z)-[(R,S)-carboxy( 3,4-dihydroxyphenyl)methyloxyimino]acetamido] -3-[1- (methylamino)pyridinium-4-thiomethyl]ceph-3-em-4 -carboxylate;

[6R,7R]-7-[2-(2-Amino-4-thiazolyl)-2-(Z)-[(S)-carboxy( 3,4-dihydroxyphenyl)methyloxyimino]acetamido] -3-[1- (methylamino)pyridinium-4-thiomethyl]ceph-3-em-4-carboxylate;

[6R,7R]-7-[2-(2-Amino-4-thiazolyl)-2-(Z)-[(R)-carboxy( 3,4-dihydroxyphenyl)methyloxyimino]acetamido] -3-[1- (methylamino)pyridinium-4-thiomethyl]ceph-3-em-4 -carboxylate;

[6R, 7R]-3-[1-Aminopyridinium-4-thiomethyl] -7-[2 (2-amino-4-thiazolyl)-2-(Z)-[(R, S )-carboxy(3,4 -dihydroxyphenyl)methyloxyimino]acetamido]ceph-3-em-4 -carboxylate;

[6R, 7R]-3-[1-Aminopyridinium-4-thiomethyl] -7-[2-(2-amino-4-thiazolyl)-2-(Z)-[(S)-carboxy( 3,4-dihydroxyphenyl)methyloxyimino]acetamido]ceph-3 -em-4-carboxylate;

[6R, 7R]-3-[1-Aminopyridinium-4-thiomethyl]-7 -[2-(2-amino-4-thiazolyl)-2-(Z)-[(R)-carboxy(3,4 -dihydroxyphenyl)methyloxyimino]acetamido]ceph-3 -em-4-carboxylate;

[6R,7R]-3-(1-Amino-2,3-cyclopentenopyridinium-4-thiomethyl)- 7-[2-(2-amino-4-thiazolyl)-2-(Z)-(methoxyimino) acetamido]-ceph-3-em-4-carboxylate;

[6R,7R]-7-[2-(2-Amino-4-thiazolyl)-2-(Z)-(methoxyimino) acetamido]-3-[1-(2-pyridylamino)pyridinium-4 -thiomethyl]ceph-3-em-4-carboxylate;

[6R, 7R]-7-[2-(2-Amino-4-thiazolyl)-2-(Z)-(methoxyimino)acetamido] -3-[1-(3,5-dimethylisoxazol- 4-yl)methylaminopyridinium-4-thiomethyl]ceph-3 -em-4-carboxylate;

[6R, 7R]-7-[2-(2-Amino-4-thiazolyl)-2-(Z)-(methoxyimino)-acetamido] -3-[1-[N-(3,4-dihydroxybenzoyl)N-methylamino] pyridinium-4-thiomethyl]ceph- 3-em-4-carboxylate;

[6R, 7R]-7-[2-(2-Amino-4-thiazolyl)-2-(Z)-(hydroxyimino)-acetamido] -3-[1-[N-(3,4-dihydroxybenzoyl)-N-methylamino] pyridinium-4-thiomethyl]ceph-3-em-4 -carboxylate;

[6R, 7R]-7-[2-(2-Amino-4-thiazolyl)-2-(Z)-(1 -carboxy-1-methylethoxyimino)acetamido]-3-[1-[N-( 3,4-dihydroxybenzoyl)-N-methylamino]pyridinium- 4-thiomethyl]ceph-3-em-4-carboxylate;

[6R, 7R]-7-[2-(2-Amino-4-thiazolyl)-2-(Z)-(1 -carboxy-1-methylethoxyimino)acetamido]-3-[1-(N-benzoyl-N-methylamino)pyridinium- 4-thiomethyl]ceph- 3-em-4-carboxylate;

[6R, 7R]-7-[2-(2-Amino-4-thiazolyl)-2-(Z)-(methoxyimino)-acetamido] -3-[1-(N-benzoyl-N-methylamino)pyridinium- 4-thiomethyl]ceph-3-em-4-carboxylate;

[6R, 7R]-7-[2-(2-Amino-4-thiazolyl)-2-(Z)-(methoxyimino)acetamido] -3-[1-[N-(3,4-dihydroxycinnamoyl)-N-methylamino] pyridinium-4-thiomethyl]ceph-3-em-4 -carboxylate;

[6R, 7R]-3-[1-(N-Acetyl-N-methylamino)pyridinium-4 -thiomethyl]-7-[2-(2-amino-4-thiazolyl)-2-(Z)-(methoxyimino)acetamido] ceph-3-em-4-carboxylate

[6R, 7R]-7-[2-(2-Amino-4-thiazolyl)-2-(Z)-(methoxyimino)-acetamido] -3-[1-[N-methyl-N-( 4-nitrobenzoyl)amino]pyridinium-4-thiomethyl] ceph-3-em-4-carboxylate;

[6R, 7R]-7-[2-(2-Amino-4-thiazolyl)-2-(Z)-(methoxyimino)-acetamido] -3-[1-[N-(4 -methoxybenzoyl)-N-methylamino]pyridinium-4-thiomethyl] ceph-3-em-4-carboxylate;

[6R, 7R]-7-[2-(2-Amino-4-thiazolyl)-2-(Z)-(methoxyimino)-acetamido] -3-[1-[N-(2-furoyl)-N-methylamino] pyridinium-4-thiomethyl]ceph-3-em-4 -carboxylate;

[6R, 7R]-7-[2-(2-Amino-4-thiazolyl)-2-(Z)-(methoxyimino) acetamido]-3-(1-ureidopyridinium-4-thiomethyl) ceph-3 -em-4-carboxylate;

[6R, 7R]-7-[2-(2-Amino-4-thiazolyl)-2-(Z)-(methoxyimino) acetamido]-3-[1-(1,3-dimethylureido)pyridinium-4-thiomethyl] ceph-3-em-4-carboxylate;

[6R, 7R]-7-[2-(2-Amino-4-thiazolyl)-2-(Z)-(methoxyimino)acetamido] -3-[1-(1-methylureido)pyridinium-4 -thiomethyl]ceph-3-em-4-carboxylate;

[6R, 7R]-7-[2-(2-Amino-4-thiazolyl)-2-(Z)-(methoxyimino)acetamido] -3-[1-(2-oxopyrrolidin-1-yl)pyridinium-4-thiomethyl]ceph-3-em-4-carboxylate;

[6R, 7R]-7-[2-(2-Amino-4-thiazolyl)-2-(Z)-(methoxyimino)acetamido] -3-[1-(2-oxopiperidin-1-yl)pyridinium-4-thiomethyl]ceph-3-em-4-carboxylate;

[6R, 7R]-7-[2-(2-Amino-4-thiazolyl)-2-(Z)-(methoxyimino)acetamido] -3-[1-[N-(4-carboxybenzoyl)-N-methylamino] pyridinium-4-thiomethyl]ceph-3-em-4-carboxylate;

[6R, 7R]-3-[1-[N-(4-Aminobenzoyl)-N-methylamino]pyridinium- 4-thiomethyl]-7-[2-(2-amino-4-thiazolyl)-2 -(Z)-(methoxyimino)acetamido]ceph-3-em-4-carboxylate;

[6R,7R]-7-[2-(5-Amino-1,2,4-thiadiazol-3-yl)-2 -(Z)-(methoxyimino)acetamido]-3-[1-(methylamino)pyridinium- 4-thiomethyl]ceph-3-em-4-carboxylate;

[6R, 7R]-7-[2-(2-Amino-4-thiazolyl)-2-(Z)-[3,4 -(methylenedioxy)benzyloxyimino]acetamido]-3-[1 -(methylamino)pyridinium-4-thiomethyl] ceph-3-em-4 -carboxylate;

[6R,7R]-3-[1-Amino-5-methoxy-2-(methoxymethyl) pyridinium-4-thiomethyl]-7-[2-(2-amino-4-thiazolyl)- 2-(Z)-(methoxyimino)acetamido]-ceph-3-em-4-carboxylate;

[6R, 7R]-3-(1-Amino-3-methoxy-2-methylpyridinium-4 -thiomethyl)-7-[2-(2-amino-4-thiazolyl)-2-(Z)-(methoxyimino)acetamido] -ceph-3-em-4-carboxylate;

[6R, 7R]-7-[2-(2-Amino-4-thiazolyl)-2-(Z)-(methoxyimino) acetamido]-3-[1-[(2-methoxyethyl)amino]pyridinium-4 -thiomethyl]ceph-3-em-4-carboxylate;

[6R,7R]-7-[2-(2-Amino-4-thiazolyl)-2-(Z)-(methoxyimino) acetamido]-3-[1-(1,2,4-triazol-4-yl)pyridinium-4 -thiomethyl]ceph-3-em-4-carboxylate;

[6R, 7R]-7-[2-(2-Amino-4-thiazolyl)-2-(Z)-(methoxyimino) acetamido]-3-[1-[(6-chloropyridin-2-yl)amino] pyridinium-4-thiomethyl]ceph-3-em-4-carboxylate;

[6R,7R]-7-[2-(2-Amino-4-thiazolyl)-2-(Z)-(methoxyimino) acetamido]-3-[1-(pyrazineamino)pyridinium-4-thiomethyl] ceph-3-em-4-carboxylate;

[6R, 7R]-7-[2-(2-Amino-4-thiazolyl)-2-(Z)-(methoxyimino) acetamido]-3-[1-[(2-methyl-4-thiazolyl)methylamino] pyridinium-4-thiomethyl]ceph-3-em-4-carboxylate;

[6R, 7R]-7-[2-(2-Amino-4-thiazolyl)-2-(Z)-(methoxyimino) acetamido]-3-[1-[(2-imidazolin-2-yl)amino]pyridinium-4 -thiomethyl]ceph-3-em-4-carboxylate;

[6R, 7R]-7-[2-(2-Amino-4-thiazolyl)-2-(Z)-(methoxyimino) acetamido]-3-[1-(phthalazin-1-yl)pyridinium-4 -thiomethyl]ceph-3-em-4-carboxylate;

[6R, 7R]-7-[2-(2-Amino-4-thiazolyl)-2-(Z)-(methoxyimino) acetamido]-3-[1-[(cyanomethyl)amino]pyridinium-4 -thiomethyl]ceph-3-em-4-carboxylate;

[6R, 7R]-7-[2-(2-Amino-4-thiazolyl)-2-(Z)-(methoxyimino) acetamido]-3-[1-(prop-2-yn-1-ylamino)pyridinium-4 -thiomethyl]ceph-3-em-4-carboxylate;

[6R,7R]-7-[2-(2-Amino-4-thiazolyl)-2-(Z)-(methoximino) acetamido]-3-[1-(methylamino)pyridinium-4-thiomethyl] ceph-3-em-4-carboxylate-1-oxide; and

[6R,7R]-3-(1-Amino-2,6-dimethylpyridinium-4-thiomethyl) -7-[2-(2-amino-4-thiazolyl)-2-(Z)-(methoxyimino) acetamido]ceph-3-em-4-carboxylate.

The antibiotic compounds according to the invention may be formulated for administration in any convenient way for use in human or veterinary medicine, according to techniques and procedures per se known in the art with reference to other antibiotics, and the invention therefore includes within its scope a pharmaceutical composition comprising an antibiotic compound according to the present invention such as, for example a pharmaceutically acceptable compound of formula (I) or a salt or in vivo hydrolysable ester thereof above together with a pharmaceutically acceptable carrier or excipient. The compositions may be formulated for administration by any suitable route, such as oral or parenteral, or by topical application. Normally administration will be via a parenteral route. The compositions may be in the form of tablets, capsules, powders, granules, lozenges, creams or liquid preparations, such as oral or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, methyl cellulose, glucose syrup, gelatin, hydroxyethylcellulose, carboxymethyl cellulose, aluminium stearate gel or hydrogenated edible fats; emulsifying agents, for example lecithin, sorbitan monooleate, or acacia; non-aqueous vehicles (which may include edible oils), for example almond oil, oily esters, glycerine, propylene glycol, or ethyl alcohol; preservatives, for example methyl or propyl p-hydroxybenzoate or sorbic acid; and, if desired conventional flavouring or colouring agents. Suppositories will contain conventional suppository base, eg cocoa-butter or other glyceride.

For parenteral administration, fluid unit dosage forms are prepared utilising the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing. Advantageously, agents such as local anaesthetic, preservative and buffering agents can be dissolved in the vehicle. To enhance the stability, the composition can be frozen after filling into the vial and the water removed under vacuum. The dry lyophilised powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

The composition may contain from 0.1% to 99.5% by weight, preferably from 10–60% by weight, of the active material, depending on the method of administration. Where the compositions comprise dosage units, each unit will preferably contain from 50–500 mg of the active ingredient. The dosage as employed for adult human treatment will preferably range from 100 mg to 12 g per day for an average adult patient (body weight 70 kg), for instance 1500 mg per day, depending on the route and frequency of administration. Such dosages correspond to approximately 1.5 to 170 mg/kg per day. Suitably the dosage is from 1 to 6g per day.

The daily dosage is suitably given by administering a compound of the invention several times in a 24-hour period. Typically, 250 mg is administered 4 times a day although, in practice, the dosage and frequency of administration which will be most suitable for an individual patient will vary with the age, weight and response of the patients, and there will be occasions when the physician will choose a higher or lower dosage and a different frequency of administration. Such dosage regimens are within the scope of this invention.

No toxicological effects are indicated when a pharmaceutically acceptable compound of the invention of formula (I) or a salt or in vivo hydrolysable ester thereof is administered in the above mentioned dosage range.

The antibiotic compounds according to the present invention may be the sole therapeutic agent in the compositions of the invention or a combination with other antibiotics and/or β-lactamase inhibitors may be employed.

Advantageously the compositions also comprise a compound of formula (III) or a pharmaceutically acceptable salt or ester thereof:

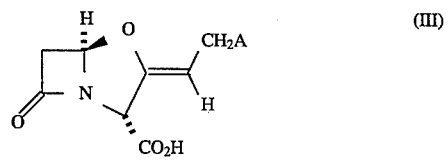

(III)

wherein A is hydroxyl; substituted hydroxyl; thiol; a group of formula $SO_2R^{14}$ wherein $R^{14}$ is $(C_{1-6})$alkyl; substituted thiol; amino; mono- or di-(hydrocarbyl) substituted amino; mono- or di-acylamino; an optionally substituted triazolyl group; or an optionally substituted tetrazolyl group as described in EP-A-0 053 893 (to Beecham Group plc).

A further advantageous composition comprises a pharmaceutically acceptable antibiotic compound of the formula (I) or a salt or an in vivo hydrolysable ester thereof and a pharmaceutically acceptable carrier or excipient together with a β-lactamase inhibitor of formula (IV) or a pharmaceutically acceptable salt or in vivo hydrolysable ester thereof:

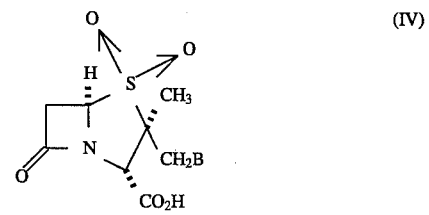

(IV)

wherein B is hydrogen, halogen or a group of formula:

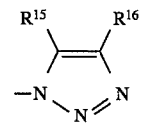

in which $R^{15}$ and $R^{16}$ are the same or different and each is hydrogen, $(C_{1-6})$alkoxycarbonyl, or carboxy or a pharmaceutically acceptable salt thereof.

Further suitable β-lactamase inhibitors include 6-alkylidene penems as described in EP-A-0 041 768 and EP-A-0 154 132 (to Beecham Group plc).

Further suitable β-lactamase inhibitors include 6β-bromopenicillanic acid and salts and in vivo hydrolysable esters thereof and 6β-iodopenicillanic acid and salts and in vivo hydrolysable esters thereof.

Such compositions of this invention comprising a β-lactamase inhibitor are formulated in conventional manner.

The present invention also includes a method of treating bacterial infections in humans and animals which method comprises administering a therapeutically effective amount of an antibiotic compound of the present invention of the formula (Ia) or a pharmaceutically acceptable salt or in vivo hydrolysable ester thereof.

In a further aspect, the present invention also provides for the use of a compound of formula (Ia) or a pharmaceutically acceptable salt or an in vivo hydrolysable ester thereof for the manufacture of a medicament for treating bacterial infection.

The pharmaceutically acceptable antibiotic compounds of the present invention of formula (Ia) or salts or in vivo hydrolysable esters thereof are active against a broad range of Gram-positive and Gram-negative bacteria, and may be used to treat a wide range of bacterial infections including those in immunocompromised patients.

Amongst many other uses, the pharmaceutically acceptable compounds of the invention of formula (Ia) or salts or in vivo hydrolysable esters thereof are of value in the treatment of respiratory tract and urinary tract infections in humans and may also be used to treat mastitis in cattle.

A particular advantage of the antibacterially active compounds of this invention is their stability to β-lactamase enzymes and they are therefore effective against β-lactamase producing organisms.

The present invention further provides a process for the preparation of a compound of formula (I) which process comprises treating a compound of formula (V):

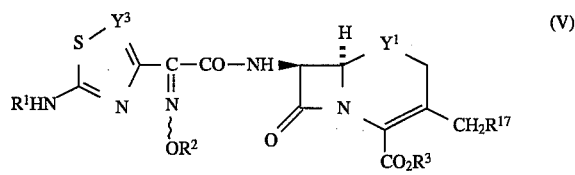

(V)

wherein $R^1$, $R^2$, $R^3$, $Y^1$, and $Y^3$ are as hereinbefore defined, and $R^{17}$ is a leaving group; and wherein any reactive groups may be protected;
with a thiopyridone compound of formula (VI):

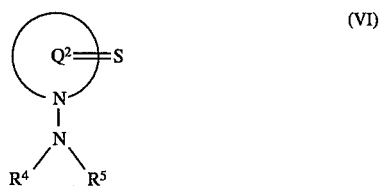

(VI)

wherein the nucleus:

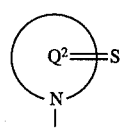

hereinafter referred to as the ring $Q^2$ is such that it is converted to the nucleus of the group $Y^2$ (as hereinbefore defined) in situ during the course of the reaction;
and $R^4$ and $R^5$ are as hereinbefore defined; with the proviso that when $R^{17}$ is an acyloxy group —$CO_2R^3$ must be in the free acid form or a salt thereof; and thereafter if necessary carrying out one or more of the following steps:

i) converting each or any one of the groups $R^2$, $R^3$, $R^4$ and $R^5$ into a different group $R^2$, $R^3$, $R^4$ and $R^5$;

ii) removing any protecting groups; or iii) converting the product into a salt.

At the end of the process described hereinabove and in other processes for the preparation of the compound of formula (I) described hereinbelow it may be necessary to remove protecting groups. Deprotection may be carried out by any convenient method known in the art that does not cause unwanted side reactions to occur to any appreciable extent.

Suitable leaving groups $R^{17}$ include halo such as chloro, bromo or iodo or an acyloxy group such as, for example, the acetoxy group. Preferred groups for $R^{17}$ are chloro and iodo.

This reaction is desirably conducted in a solvent. For example, use can be made of water, or of organic solvents inert to the starting compounds, such as dimethylformamide, dimethylacetamide, dioxane, acetone, dichloromethane, 1,2-dichloroethane, acetonitrile, dimethylsulfoxide or tetrahydrofuran, or mixtures thereof. The reaction temperature and time depend, among other factors, upon the starting compounds and solvent to be employed but generally the reaction is carried out at a selected temperature within the range of 0° to 100° C. for a selected time of a few minutes to several days.

Compounds of formula (V) wherein $R^{17}$ is acyloxy may be prepared by analogy with procedures described in Bucourt R., et al, *Tetrahedron*, 1978, 34, 2233.

Compound of formula (V) wherein $R^{17}$ is halo may be prepared from readily available starting materials by conventional methodology, for instance, by the coupling of compounds of formula (IX) and formula (XI), as hereinafter defined, wherein $R^{17}$ is halo.

Preferred compounds of the formula (V) include salts and esters in which $R^3$ is as hereinbefore defined and in particular in which $R^3$ is diphenylmethyl, p-methoxybenzyl or trimethylsilyl.

Compounds of formula (VI) may be prepared by treating the corresponding thiopyranone with a hydrazine derivative of the formula (VII):

$$H_2NNR^4R^5 \qquad\qquad (VII)$$

wherein $R^4$ and $R^5$ are as hereinbefore defined, by analogy with the process described by Ibrahim El-Sayad El-Kholy et al., *J. Het. Chem.*, 1974, 11, 487.

Alternatively, compounds of formula (VI) may be obtained by treating the corresponding pyridone with, for instance, Lawesson's reagent or phosphorus pentasulphide, according to conventional procedures. Suitable pyridones may be prepared according to the methodology of Freeman et al. *J. Amer. Chem. Soc.*, 1947, 69, 858.

Included within the compounds of formula (VI) are sub-groups of compounds of the formulae (VIa) and (VIb):

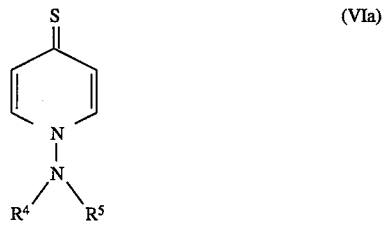

(VIa)

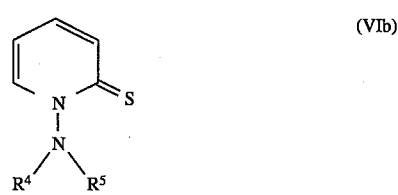

(VIb)

wherein $R^4$ and $R^5$ are as hereinbefore defined and in which the 4- or 2-thiopyridone ring may be optionally substituted at a ring carbon available for substitution by up to four substituents, of which two may be linked to form the residue of a heterocyclic or carbocyclic ring.

It will be appreciated that within the process hereinbefore described there exists a specific process in which in the compound of formula (V), $Y^1$ is sulphur, —SO— or —$SO_2$—.

The compounds of formula (I) may also suitably be prepared by reacting a compound of formula (VIII) or a salt thereof:

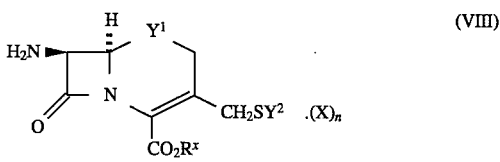

wherein X, $Y^1$, $Y^2$ and n are as hereinbefore defined, $R^x$ is hydrogen or a readily removable carboxyl blocking group and the 7β-amino group is optionally substituted with a group which permits acylation to take place; and any reactive groups may be protected;
with an N-acylating derivative of an acid of formula (IX):

wherein $R^2$ is as hereinbefore defined and $Y^5$ is a group of formula:

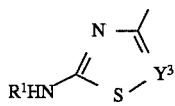

or a group which is convertible thereto, and $R^1$ is as hereinbefore defined; and wherein any reactive groups may be protected; and thereafter, if necessary, carrying out one or more of the following steps:

(i) removing any protecting group, including an amino-protecting group $R^1$;

(ii) converting the group $R^x$ into a group $R^3$;

(iii) converting the product to a salt;

(iv) converting a group which is convertible to $Y^5$ into $Y^5$, or (v) converting each or any one of the groups $R^4$ and $R^5$ into a different group $R^4$ and $R^5$.

Suitable groups which permit acylation to take place and which are optionally present on the amino group of the starting material of the formula (VIII) include silyl, stannyl and phosphorus groups, for example trialkylsilyl groups such as trimethylsilyl, trialkyltin groups such as tri-n-butyltin, phosphorus groups of formula —$PR^{18}R^{19}$ wherein $R^{18}$ is an alkyl, haloalkyl, aryl, aralkyl, alkoxy, haloalkoxy, aryloxy, aralkyloxy or dialkylamino group, $R^{18}$ is the same as $R^{19}$ or is halogen or $R^{18}$ and $R^{19}$ together form a ring; suitable such phosphorus groups being —$P(OC_2H_5)_2$, —$P(C_2H_5)_2$,

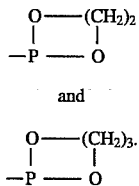

and

A group which may optionally be introduced in situ prior to acylation onto the amino group in the compound of formula (VIII) is trimethylsilyl.

An appropriate reactive N-acylating derivative of the acid (IX) is employed in the above process.

Suitable N-acylating derivatives include an acid halide, preferably the acid chloride or bromide.

Acylation with an acid halide may be effected in the presence of an acid binding agent, for example a tertiary amine (such as pyridine or dimethylaniline), molecular sieves, or an inorganic base (such as calcium carbonate or sodium bicarbonate) or a silylated derivate of acetamide [such as trimethylsllylacetamide or N,O-bis(trimethylsilylacetamide)] or an oxirane, which binds hydrogen halide liberated in the acylation reaction. The oxirane is preferably a ($C_{1-6}$)- 1,2-alkylene oxide, such as ethylene oxide or propylene oxide. The acylation reaction using an acid halide may be carried out at a temperature in the range −50° C. to +50° C., preferably −20° C. to +20° C., in aqueous or non-aqueous media such as water, acetone, tetrahydrofuran, ethyl acetate, dimethylacetamide, dimethylformamide, acetonitrile, dichloromethane, 1,2-dichloroethane, or mixtures thereof. Alternatively, the reaction may be carried out in an unstable emulsion of water-immiscible solvent, especially an aliphatic ester or ketone, such as methyl isobutyl ketone or butyl acetate. Preferred solvents include tetrahydrofuran, and anhydrous chlorinated hydrocarbons, especially dichloromethane.

The acid halide may be prepared by reacting the acid (IX) or a salt or suitable derivative thereof with a halogenating (eg chlorinating or brominating) agent such as phosphorus pentachloride, phosphorus oxychloride, thionyl chloride, oxalyl chloride, or phosgene.

Further suitable derivatives of the acid (IX) which may be employed in the above process include labile esters such as silyl esters. Suitable silyl esters include, for example, tri($C_{1-6}$)alkyl silyl esters, especially the trimethylsilyl ester.

Other suitable N-acylating derivatives of the acid (IX) include symmetrical and mixed anhydrides. Suitable mixed anhydrides are alkoxyformic anhydrides, or anhydrides with, for example, carbonic acid monoesters, trimethyl acetic acid, thioacetic acid, diphenylacetic acid, benzoic acid, phosphorus acids (such as phosphoric, phosphorous, and phosphinic acids) or aromatic or aliphatic sulphonic acids (such as p-toluenesulphonic acid or methanesulphonic acid). Preferably the N-acylating derivative of the acid (IX) is a mixed anhydride with methanesulphonic acid.

When a symmetrical anhydride is employed, the reaction may be carried out in the presence of 2,6-lutidine as catalyst.

When a mixed anhydride is employed the N-acylating derivative is preferably prepared in the presence of an organic base such as triethylamine and/or N,N-diisopropylethylamine in a suitable solvent such as DMF or dichloromethane at between −50° C. and 100°. Alternatively, the N-acylating derivative may be prepared from an alkali metal salt of the acid of formula (IX), such as the sodium salt, in a suitable solvent such as DMF at between −50° C. and room temperature. The N-acylating derivative of the acid of formula (IX) so derived may then be reacted with a compound of formula (VIII). The acylation reaction may conveniently be carried out at between −50° C. to +50° C. in a suitable solvent such as water, acetonitrile, DMF or dichloromethane. The reaction may be carried out in the presence of a suitable base such as triethylamine, sodium hydrogen carbonate, pyridine or N,N-diisopropylethylamine.

Further N-acylating derivatives of acid (IX) are the acid azide, or activated esters such as esters with cyanomethanol, p-nitrophenol, 2,4-dinitrophenol, thiophenol, halophenols, including pentachlorophenol, monomethoxyphenol, N-hydroxy succinimide, N-hydroxybenzotriazole, or 8-hydroxyquinoline; or amides such as N-acylsaccharins, N-acylthiazolidin- 2-thione or N-acylphthalimides; or an alkylidene iminoester prepared by reaction of the acid (IX) with an oxime.

Other N-acylating derivatives of the acid of formula (IX) are thioesters of formula (X):

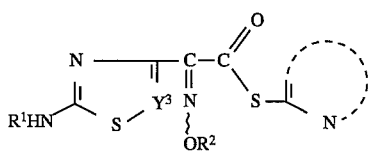

wherein $R^1$, $R^2$, and $Y^3$ are as hereinbefore defined and the moiety:

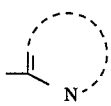

represents a 5- or 6-membered heterocyclic ring, which may contain, in addition to the nitrogen atom, one or two further heteroatoms, selected from oxygen, nitrogen and sulphur and which may be substituted or fused to a benzene ring which may itself be substituted.

Preferred thioester acylating agents derived from the acid of formula (IX) are the thioesters (Xa) or (Xb):

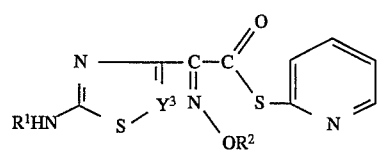

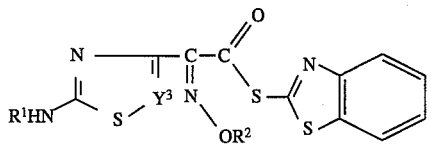

wherein $R^1$, $R^2$ and $Y^3$ are as hereinbefore defined.

Compounds of the formula (Xa) and (Xb) may be prepared by treatment of the acid (IX) with 2,2'-dipyridyldisulphide or 2,2'-dibenzothiazolyldisulphide respectively, in the presence of triphenylphosphine, analogously to the routes described in EP-A-0 037 380 (to Biochemie GmbH). Conveniently, in compounds of the formula (Xa) and (Xb), $R^1$ may be hydrogen.

Other suitable N-acylating derivatives of the acid (IX) include the reactive intermediates formed by reaction in situ with a condensing agent such as a carbodiimide, for example, N,N'-diethyl-, di-n-propyl- or diisopropylcarbodiimide, N,N'-di-cyclohexylcarbodiimide, or N-ethyl-N'-[3-(dimethylamino)propyl] carbodiimide; a suitable carbonyl compound, for example, N,N'-carbonyldiimidazole or N,N'-carbonylditriazole; an isoxazolinium salt, for example, N-ethyl- 5-phenylisoxazolinium-3-sulphonate or N-t-butyl-5 -methylisoxazolinium perchlorate; or an N-alkoxycarbonyl 2-alkoxy-1,2-dihydroquinoline, such as N-ethoxycarbonyl 2-ethoxy-1,2-dihydroquinoline. Other condensing agents include Lewis acids (for example $BBr_3.C_6H_6$); or a phosphoric acid condensing agent such as diethylphosphorylcyanide. The condensation reaction is preferably carried out in an organic reaction medium, for example, dichloromethane, dimethylformamide, acetonitrile, alcohol, benzene, dioxan or tetrahydrofuran.

A further method of forming the N-acylating derivative of the acid (IX) is to treat the acid of formula (IX) with a solution or suspension preformed by addition of a carbonyl halide, preferably oxalyl chloride, or a phosphoryl halide such as phosphorus oxychloride, to a halogenated hydrocarbon solvent, preferably dichloromethane, containing a lower acyl tertiary amide, preferably N,N-dimethylformamide. The N-acylating derivative of the acid (IX) so derived may then be caused to react with a compound of formula (VIII). The acylation reaction may conveniently be carried out at −40° to +30° C., if desired in the presence of an acid binding agent such as pyridine, trimethylsilylacetamide or N,O-bis(trimethylsilyl acetamide). A catalyst such as 4-dimethylaminopyridine may optionally also be added. A preferred solvent for the above acylation reaction is dichloromethane.

A preferred amino protecting group $R^1$ in the intermediate of formula (IX) is trityl, which $R^1$ group may be suitably removed from the product of formula (I) by treatment with formic acid or trifluoracetic acid.

Compounds of formula (IX) may be prepared by routes analogous to those disclosed in GB 2 025 398A and by Takasugi et al., *J. Antibiotics* [1983]36, 846 et seq and modifications thereto described in EP-A-0 210 815 (Beecham Group plc).

Compounds of formula (VIII) are novel and useful intermediates in the preparation of compounds of formula (I).

Accordingly, a further aspect of the invention provides compounds of formula (VIII) as hereinbefore defined.

The compounds of formula (VIII) herein which are, inter alia, intermediates for the compounds of formula (I) as hereinbefore defined may be prepared by reacting a compound of formula (XI) or acid addition salt thereof:

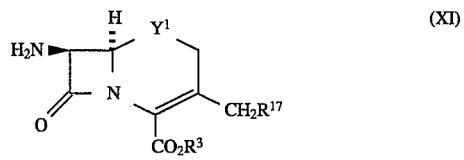

wherein $R^3$, $R^{17}$, and $Y^1$ are as hereinbefore defined, and the 7β-amino group is optionally protected with an amino protecting group; with a compound of the formula (VI) as hereinbefore defined;

with the proviso that when $R^{17}$ is an acyloxy group, the group $CO_2R^3$ must be in the free acid form or a salt thereof; and thereafter if necessary carrying out one or more of the following steps:

1) converting each or any of the groups $R^4$ and $R^5$ into a different group $R^4$ and $R^{5;}$ ii) removing any protecting group; or iii) converting the group $R^3$ into a group $R^x$.

Compounds of formula (V), as hereinbefore defined, may be prepared by reacting a compound of formula (XI) as hereinbefore defined or a derivative thereof in which the 7β-amino group is substituted with a group which permits acylation to take place; and any reactive groups may be protected; with an N-acylating derivative of an acid of formula (IX), as hereinbefore defined and thereafter, if necessary,carrying out one or more of the following steps:

(i) removing any protecting group, (ii) replacing a group $R^{17}$ by another group $R^{17}$; or (iii converting a group which is convertible to $Y^5$ into $Y^5$.

Compounds of formula (XI) are well known and readily available.

Compounds of the formula (I) in which $Y^1$ is sulphur, —SO—, or —$SO_2$— may be inter-converted by methods known in the art.

Thiopyridones of formula (VI), as hereinbefore defined, in particular, thiopyridones of formula (VIc):

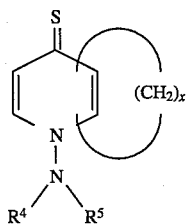

in which $R^4$ and $R^5$ are as hereinbefore defined and x is 0 or an integer from 3 to 5, are useful intermediates in the processes for the preparation of compounds of formulae (I) and (VIII) as hereinbefore described.

Accordingly, a further aspect of the invention provides compounds of formula (VI), as hereinbefore defined, excluding:
1-(optionally substituted)amino-2,6-dimethyl-4 -thiopyridones;
1-(optionally substituted)amino-3,5-diphenyl-4 -thiopyridones; and
1-(optionally substituted)amino-3-(hydroxy or methoxy)-2-methyl-4-thiopyridones.

A preferred sub-group of the compounds of formula (VI), are the compounds of formula (VIc), as hereinbefore defined.

Suitable examples of compounds for formula (VI) include:
1-(Methylamino)-4-thiopyridone;
1-[N-(t-Butyloxycarbonyl)-N-methylamino]-4 -thiopyridone;
1-(Dimethylamino)-4-thiopyridone;
1-(t-Butyloxycarbonylamino)-4-thiopyridone;
1-[N-(t-Butyloxycarbonyl)-N-(t-butyloxycarbonylmethyl)amino] -4-thiopyridone;
1-[N-(t-Butyloxycarbonyl)-N-ethylamino]-4-thiopyridone;
1-[4-(2-Hydroxyethyl)piperazin-1-yl]-4-thiopyridone;
1-[(3S)-3-(t-Butyloxycarbonylamino)-2-oxoazetidin-1-yl] -4-thiopyridone;
1-[N-(t-Butyloxycarbonyl)-N-(cyclopropylmethyl)amino] -4-thiopyridone;
1-[N-(t-Butyloxycarbonyl)-N-(prop-2-en-1-yl)amino]-4 -thiopyridone;
1-Amino-4-thiopyridone;
1-(Propylamino)-4-thiopyridone;
1-[N-(t-Butyloxycarbonyl)-N-(cyclopentyl)amino]-4-thiopyridone;
1-[N-Butyl-N-(t-butyloxycarbonyl)amino]-4-thiopyridone;
1-[N-(t-Butyloxycarbonyl)-N-hexylamino]-4-thiopyridone;
1-[N-(t-Butyloxycarbonyl)-N-(1-isopropyl)amino]-4-thiopyridone;
1-[N-(t-Butyloxycarbonyl)-N-(2-hydroxyethyl)amino]-4 -thiopyridone;
1-(2-Pyridylamino)-4-thiopyridone;
1-(3,5-Dimethylisoxazol-4-yl)methylamino-4-thiopyridone;
1-(N-Acetyl-N-methylamino)-4-thiopyridone;
1-[N-Methyl-N-(4-nitrobenzoyl)amino]-4-thiopyridone;
1-[N-(4-Methoxybenzoyl)-N-methylamino]-4-thiopyridone;
1-[N-(2-Furoyl)-N-methylamino]-4-thiopyridone;
1-[N-[3,4-bis(4-Methoxybenzyloxy)benzoyl]-N-methylamino] -4-thiopyridone;
1-(N-Benzoyl-N-methylamino)-4-thiopyridone;
1-[N-[3,4-bis(4-Methoxybenzyloxy)cinnamoyl]-N-methylamino] -4-thiopyridone;
1-Ureido-4-thiopyridone;
1-(1,3-Dimethylureido)-4-thiopyridone;
1-(1-Methylureido)-4-thiopyridone;
1-(2-Oxopyrrolidin-1-yl)-4-thiopyridone;
1-(2-Oxopiperidin-1-yl)-4-thiopyridone;
1-(t-Butyloxycarbonylamino)-2,3-cyclopenteno-4 -thiopyridone;
1-[N-(4-Diphenylmethoxycarbonylbenzoyl)-N-methylamino] -4-thiopyridone;
1-[N-[4-(t-Butoxycarbonylamino) benzoyl]-N-methylamino] -4-thiopyridone;
1-(t-Butyloxycarbonylamino)-5-methoxy-2-(methoxymethyl)- 4-thiopyridone;
1-[N-(t-Butyloxycarbonyl)-N-(2-methoxyethyl)amino]-4 -thiopyridone;
1-(1,2,4-Triazol-4-yl)-4-thiopyridone;
1-[(6-Chloropyridin-2-yl)amino]-4-thiopyridone;
1-(Pyrazineamino)-4-thiopyridone;
1-[N-(t-Butyloxycarbonyl)-N-(2-methyl-4-thiazolyl) methylamino]-4-thiopyridone;
1-[(2-Imidazolin-2-yl)amino]-4-thiopyridone;
1-(Phthalazin-1-ylamino)-4-thiopyridone;
1-[N-(t-Butyloxycarbonyl)-N-(cyanomethyl)amino]-4 -thiopyridone;
1-[N-(t-Butyloxycarbonyl)-N-(prop-2-yn-1-yl)amino]-4 -pyridone;
and corresponding analogues thereof lacking an amino protecting group such as, for example, t-butoxycarbonyl, a hydroxy protecting group, such as for example, 4-methoxybenzyloxy, or a carboxy protecting group, such as, for instance, 4-diphenylmethoxy.

The compounds of formulae (Ia), (Ib), and (Ic) may be prepared by similar processes to those described hereinabove as suitable for the preparation of a compound of the formula (I), except that each process for the preparation of the compound of formulae (Ia), (Ib) or (Ic) further comprises, if necessary, the step of converting the product into a pharmaceutically acceptable salt or pharmaceutically acceptable in vivo hydrolysable ester.

Conversion of betaines of formula (Ib) into salts of formula (Ic) and vice versa may readily be carried out by conventional methods. For example salts of the formula (Ic) may be prepared from betaines of formula (Ib) by treatment with a dilute mineral acid such as hydrochloric acid or sulphuric acid.

Quaternary salts within formula (Ic) may also be prepared by salt exchange in a conventional manner, for example by means of an ion-exchange resin.

The antibiotic compounds of the present invention are active against a wide range of Gram-negative and Gram-positive organisms including *E. coli* such as, for example ESS, JT4, JT425 and NCTC 10418; *Pseudomonas Spp.* such as *Ps. aeruginosa* for example 10662 and Dalgleish; *Serratia marcescens* US32; *Klebsiella aerogenes* A; *Enterobacter cloacae* N1; *P. mirabilis* such as, for example C977 and 889; *P. morganii; P. rettgeri; B. subtilis; Staph. aureus* such as, for example Oxford and Russell; *N. catarrhalis* 1502.

The following Examples illustrate the preparation of the compounds of the present invention.

PREPARATION 1

1-(Methylamino)-4-thiopyridone a) t-Butyl 1-methylhydrazinecarboxylate

N-Methylhydrazine (1.6 ml; 0.03 mol) in dichloromethane (20 ml) was treated with di-t-butyl dicarbonate (6.6 g; 0.03 mol) in dichloromethane (25 ml) dropwise, and stirred for 90 minutes. The mixture was decanted from the sticky residue and evaporated to minimum volume twice from dichloromethane and once from dichloromethane/toluene to give the title compound (4 g, 97%); $\delta_H$ (CDCl$_3$) 1.47 (9H, s), and 3.03 (3H, s).

b) 1-[N-(t-Butyloxycarbonyl)-N-methylamino]-4-thiopyridone t-Butyl 1-methylhydrazinecarboxylate (0.5 g; 3.4 mmol) and 4-thiopyrone (0.34 g; 3 mmol) in ethanol (20 ml) were refluxed for 24 hours. The solution was evaporated to dryness and the product purified by chromatography on silica gel eluting with mixtures of hexane and ethyl acetate to give the title compound (0.55 g, 76%); $\delta_H$ (CDCl$_3$) 1.47 (9H, s), 3.37 (3H, s), 7.19 and 7.32 (4H, ABq, J 7Hz); $\lambda_{max}$ (EtOH) 356 nm (E 29050 dm$^3$ mol$^{-1}$ cm$^{-1}$) (Found: M$^+$, 240.0945, C$_{11}$H$_{16}$N$_2$O$_2$S requires M, 240.0932).

c) 1-(Methylamino)-4-thiopyridone

1-[N-(t-Butyloxycarbonyl)-N-methylamino]-4-thiopyridone (1 g, 4.16 mmol) in dichloromethane (40 ml) was treated with trifluoroacetic acid (5 ml) and stirred for 2½ hours. On completion of the reaction the mixture was evaporated to dryness and the residue dissolved in ethyl acetate. The product was extracted into water maintained at pH 6.8 with sodium bicarbonate. The water was evaporated to low volume and then the product absorbed onto silica gel by evaporation. The product was then purified by chromatography on silica gel eluting with mixtures of ethanol in dichloromethane to give the title compound (0.4 g, 67%) $\upsilon_{max}$ (KBr) 1685, 1605, 1523 and 1108 cm$^{-1}$; $\delta_H$ (CDCl$_3$) 2.95 (3H, d, J 6Hz), 5.46 (1H, q, J 6Hz), and 7.34 (4H, s); M$^+$ 140.

PREPARATION 2

1-(Dimethylamino)-4-thiopyridone

4-Thiopyranone (0.112 g, 1.0 mmol) in N,N-dimethylformamide (2 ml) was treated with N,N-dimethylhydrazine (0.76 ml, 10 mmol) and stirred for 3 hours at room temperature. The solvent was evaporated under reduced pressure and the residue chromatographed on silica gel eluting with dichloromethane and mixtures of dichloromethane and ethanol to give the title compound (0.069 g, 5%); δ(CDCl$_3$) 7.55 (4H, s) 2.88 (6H, s); M$^+$ 154.

PREPARATION 3

1-(t-Butyloxycarbonylamino)-4-thiopyridone t-Butylcarbazate (0.13 g, 1.0 mmol) and 4-thiopyranone (0.11 g, 1.0 mmol) were heated at reflux in ethanol for 2 h. The mixture was allowed to cool, diluted with acetone, then evaporated under reduced pressure. Chromatography on silica gel 60 eluting with ethanol, dichloromethane (1:19) gave the title compound containing traces of unreacted t-butylcarbazate (0.49 g); $\upsilon_{max}$ (KBr) 1745, 1611, and 1503cm$^{-1}$; $\delta_H$ (CDCl$_3$) 1.51 (9H, s), and 7.33 (4H, s); M$^+$ 226.

PREPARATION 4

1-[N-(t-Butyloxycarbonyl)-N-(t-butyloxycarbonylmethyl)amino]-4-thiopyridone a) 1-(t-Butyloxycarbonylamino)-4-pyridone 4-Pyranone (1 g, 10.4 mmol) and t-butylcarbazate (1.32 g, 10 mmol) were heated at reflux in ethanol for 48 h. The solvent was gradually allowed to distil from the mixture and the residue was chromatographed on silica gel 60, eluting with ethanol, dichloromethane (1:19) to give the title compound (1.16 g, 50%); $\upsilon_{max}$ (KBr) 1723, 1630, and 1550cm$^{-1}$; $\delta_H$ 1.54 (9H, s), 6.47 (2H, d), and 7.60 (2H, d); M$^+$ 210.

(b) 1-[N-(t-Butyloxycarbonyl)-N-(t-butyloxycarbonylmethyl)amino]-4-pyridone 1-(t-Butyloxycarbonylamino)-4-pyridone (0.057 g, 0.25 mmol) in N,N-dimethylformamide (5 ml) was treated successively with potassium carbonate (0.035 g, 0.25 mmol) and t-butyl bromoacetate (0.04 ml, 0.25 mmol). The reaction mixture was stirred for 0.5 h, evaporated under reduced pressure and chromatographed on silica gel 60 eluting with ethanol, dichloromethane (1:19) to give the title compound containing traces of solvent (0.09 g); $\upsilon_{max}$ (CH$_2$Cl$_2$) 1740, 1735 (sh), 1635, and 1590cm$^{-1}$; $\delta_H$ (CDCl$_3$) 1.47 (9H, s), 1.51 (9H, s), 4.33 (2H, s), 6.37 (2H, d), and 7.70 (2H, d); M$^+$ 324.

c) 1-[N-(t-Butyloxycarbonyl)-N-(t-butyloxycarbonylmethyl)amino]-4-thiopyridone

The product from 4(b) (0.09 g, from 0.25 mmol) in toluene (5 ml) was treated with Lawesson's Reagent (0.057 g, 0.14 mmol). The mixture was heated at 80° C. for 5 mins, allowed to cool, then chromatographed on silica gel 60 eluting with ethanol, dichloromethane mixtures to give the title compound (0.081 g, 95%); $\upsilon_{max}$ (CH$_2$Cl$_2$) 1740, 1615, and 1115cm$^{-1}$; $\delta_H$ (CDCl$_3$) 1.49 (9H, s), 1.72 (9H, s), 4.41 (2H, s), and 7.42 (4H, s); M$^+$ 340.

PREPARATION 5

1-[N-(t-Butyloxycarbonyl)-N-ethylamino]-4-thiopyridone a) 1-[N-(t-Butyloxycarbonyl)-N-ethylamino]-4-pyridone 1-(t-Butyloxycarbonylamino)-4-pyridone (0.23 g, 1.1 mmol) in N,N-dimethylformamide (5 ml) was treated with potassium carbonate (0.14 g, 1.0 mmol) followed by ethyl iodide (0.08 ml, 1.0 mmol). The mixture was stirred for 1 h, evaporated under reduced pressure and chromatographed on silica gel 60, eluting with ethanol, dichloromethane (1:19) to give the title compound (0.124 g, 49%); $\delta_H$ (CDCl$_3$) 1.21 (3H, t, J 7Hz), 1.45 (9H, s), 3.82 (2H, q, J 7Hz), 6.44 (2H, d, J 8Hz), and 7.41 (2H, d, J 8Hz); M$^+$ 238.

(b) 1-[N-(t-Butyloxycarbonyl)-N-ethylamino]-4-thiopyridone

The product from (a) was reacted in a similar manner to that described in Preparation 4(c) to give the title compound: $\upsilon_{max}$ (CH$_2$Cl$_2$) 1725, 1620, and 1598cm$^{-1}$; $\delta_H$ (CDCl$_3$) 1.23 (3H, t, J 7Hz), 1.48 (9H, s), 3.95 (2H, m), 7.0–7.7 (4H, m); M$^+$ 254.

PREPARATION 6

1-[4-(2-Hydroxyethyl)piperazin-1-yl]-4-thiopyridone

1-Amino-4-(2-hydroxyethyl)piperazine (0.145 g, 1.0 mmole) in ethanol (5 ml) was treated with 4-thiopyranone (0.112, 1.0 mmole) and heated at reflux under argon for 6.0 h. The solvent was evaporated under reduced pressure and the residue chromatographed on silica gel 60 (<230 Mesh ASTM) eluting with ethanol, dichloromethane (1:4) to give the title compound (0.09 g, 38%).

PREPARATION 7

1-[(3S)-3-(t-Butyloxycarbonylamino)-2-oxoazetidin-1-yl] -4-thiopyridone (3S)-1-Amino-3-(t-butyloxycarbonylamino)-2-oxoazetidine (0.1 g, 0.5 mmol) and 4-thiopyranone (0.056 g, 0.5 mmol) were dissolved in pyridine (5 ml) and heated for 4 h at 40° C. then 18 h at 35° C. The volatiles were removed under reduced pressure and the residue chromatographed on silica gel 60, eluting with dichloromethane then ethyl acetate, to yield the title compound (0.036 g, 25%);$\upsilon_{max}$(CH$_2$Cl$_2$) 1805, 1710 and 1615cm$^{-1}$; $\delta_H$ (CDCl$_3$) 1.46 (9H,s), 4.00 (1H, t, J 5Hz), 4.12–4.19 (1H,m), 4.43–4.58 (1H,m), 5.40 (1H, d, J 7Hz), and 7.40 (4H,s).

PREPARATION 8

1-[N-(t-Butyloxycarbonyl)-N-(cyclopropylmethyl)-amino]-4 -thiopyridone.

a) 1-[N-(t-Butyloxycarbonyl)-N-(cyclopropyl-methyl)amino] -4-pyridone 1-(t-Butyloxycarbonylamino)-4-pyridone (0.23 g, 1.0 mmol) in N,N-dimethylformamide (5 ml) was treated successively with potassium carbonate (0.14 g, 1.0 mmol) and cyclopropylmethyl bromide (0.1 g, 1.0 mmol). The reaction mixture was stirred for 3 h and evaporated under reduced pressure. Purification on silica gel 60 eluting with ethanol, dichloromethane (1:19) gave the title compound (0.22 g, 76%); $\upsilon_{max}$ (KBr) 1708, 1649, 1629, and 1583 cm$^{-1}$; $\delta_H$ (CDCl$_3$) 0.18 (2H, q, J 5Hz),0.59(2H,m), 0.88–1.04 (1H,m) 1.45 (9H,s), 3.54 (2H,d, J 7Hz), 6.40 (2H,d, J 6Hz), and 7.30 (2H,d, J 6Hz); M$^+$ 264.

b) 1-[N-(t-Butyloxycarbonyl)-N-(cyclopropyl-methyl)amino] -4-thiopyridone

The product of Preparation 8(a) (0.22 g 0.8 mmol) in toluene (5 ml) was treated with Lawesson's reagent (0.17 g, 0.4 mmol) and heated at 80° C. for 1 h. The mixture was allowed to cool and chromatographed on silica gel 60 eluting with ethanol, dichloromethane mixtures to give the title compound (0.079 g, 35%); $\delta_H$ (CDCl$_3$) 0.19 (2H,q, J 5.5Hz), 0.60 (2H,q, J 5.5Hz), 0.88 (1H,t, J 5.5Hz), 1.29 (9H,s), 3.62 (2H,d, J 7Hz), and 7.2–7.8 (4H,m); M$^+$ 280.

PREPARATION 9

1-[N-(t-Butyloxycarbonyl)-N-(prop-2-en-1-yl)amino]-4 -thiopyridone a) 1-[N-(t-Butyloxycarbonyl)-N-(prop-2-en-1-yl)-amino] -4-pyridone (i) 1-(t-Butyloxycarbonylamino)-4-pyridone (0.21 g, 1.0 mmol) in 1,2-dimethoxyethane (10 ml) was treated successively with 50% sodium hydride dispersion in oil (0.048 g, 1.0 mmol) and cyclopropyl bromide (1.0 ml, 2.5 mmol). After being stirred for 48 h, the mixture was evaporated under reduced pressure. Purification on silica gel 60 eluting with ethanol, dichloromethane (1:9) gave the title compound (0.042 g, 17%); $\delta_H$ (CDCl$_3$) 1.37 (9H,s), 4.24 (2H,d, J 9Hz), 5.0–5.9 (3H,m), 6.35 (2H,m), and 7.26 (2H,m); M$^+$ 250.

(ii) 1-(t-Butyloxycarbonylamino)-4-pyridone (0.42 g, 2.0 mmol) in N,N-dimethylformamide was treated with potassium carbonate (0.3 g, 2.2 mmol) and cyclopropylbromide (1.0 ml, 12.5 mmol). The mixture was stirred for 12 days, then evaporated under reduced pressure and chromatographed on silica gel 60 eluting with ethanol, dichloromethane (1:9) to give the title compound (0,046 g, 9%).

b) 1-[N-(t-Butyloxycarbonyl)-N-(prop-2-en-1-yl)-amino] -4-thiopyridone

The product from Preparation 9(a) (0.199 g, 0.48 mmol) in toluene (5 ml) with Lawesson's reagent (0,194 g, 0.48 mmol) was heated at 80° C. for 2 h, then allowed to cool and chromatographed in silica gel 60 eluting with ethanol, dichloromethane (1:50) to give the title compound (0.089 g, 70%); $\upsilon_{max}$ (KBr) 1711, and 1615 cm$^{-1}$; $\delta_H$ (CDCl$_3$) 1.46 (9H,s), 4.26 (2H,d, J 7Hz), 5.10–5.40 (2H,m), 5.62–5.77 (1H,m), 7.03 (2H,d, J 6Hz), and 7.39 (2H,d, J 6Hz); M$^+$ 266.

PREPARATION 10

1-Amino-4-thiopyridone 1-(t-Butyloxycarbonylamino)-4-thiopyridone (0.155 g, 0.69 mmol) was treated with trifluoroacetic acid (2.0 ml, 26 mmol) and stirred for 5 mins. The reaction mixture was diluted with toluene (1 ml) and evaporated to dryness under reduced pressure. The residue was dissolved in water and adjusted to pH6.5 by addition of aqueous sodium hydrogen carbonate solution. The solution was washed with diethyl ether and evaporated under reduced pressure. The crude product was purified by chromatography on silica gel 60 eluting with ethanol, dichloromethane mixtures to give the title compound; $\upsilon_{max}$ (KBr) 1684 and 1624 cm$^{-1}$; $\delta_H$ (CDCl$_3$+CD$_3$OD) L0 7.41 (2H,d, J 7Hz), and 7.50 (2H,d, J 7Hz); M$^+$ 126.

PREPARATION 11

1-(Propylamino)-4-thiopyridone a) 1-[N-(t-Butyloxycarbonyl)-N-propylamino]-4 -pyridone 1-(t-Butyloxycarbonylamino)-4-pyridone (0.1 g, 0.047 mmol) in N,N dimethylformamide (2 ml) was treated successively with potassium carbonate (0.064 g, 0.047 mmol) and iodopropane (0.081 g, 0.047 mmol). The reaction mixture was stirred at room temperature for 3 h and evaporated under reduced pressure. Purification on silica gel 60 eluting with ethanol, dichloromethane (1:9) gave the title compound (0.098 g, 82%); $\delta_H$ (CDCl$_3$) 0.98 (3H,t J 7Hz), 1.45 (9H,s), 1.53–1.68 (2H,m) 3.62 (2H,t, J 7.5Hz), 6.35 (2H,d, J 8Hz), and 7.21 (2H,d, J 8Hz); M$^+$ 252.

b) 1-[N-(t-Butyloxycarbonyl)-N-propylamino]-4-thiopyridone

The product of Preparation 11(a) (0.098 g, 0.39 mmol) in toluene (10 ml) was treated with Lawesson's reagent (0.15 g, 0.37 mmol) and heated at 80° C. for 0.5 h. The mixture was allowed to cool and chromatographed on silica gel 60 eluting with ethanol, dichloromethane mixtures to give the title compound (0.05 g, 48%); $\delta_H$ (CDCl$_3$) 0.96 (3H,t, J 7Hz), 1.45 (9H,s), 1.5–1.65 (2H,m), 3.64 (2H,t, J 7Hz), 7.03 (2H,d, J 7Hz), and 7.40(2H,d, J 7Hz); M$^+$ 268.

c) 1-[N-Propylamino]-4-thiopyridone

The product of Preparation 11(b) (0.2 g, 0.75 mmol) was dissolved in trifluoroacetic acid (3 ml), the reaction mixture was stirred for 10 minutes, toluene (10 ml) was added and the mixture was evaporated under reduced pressure. A further two (10 ml) volumes of toluene were added and evaporated under reduced pressure. Water (10 ml) was added and the pH adjusted to 7.2 using aqueous sodium hydrogen carbonate. The product was extracted into dichloromethane and dried over magnesium sulphate, filtered and evaporated under reduced pressure. Purification on silica gel 60 eluting with ethanol, dichloromethane (1:9) gave the title compound (0.074 g, 59%); $\delta_H$ (CDCl$_3$) 1.0 (3H,t, J 7Hz), 1.5–1.6 (2H,m), 3.09 (2H,t, J 7Hz), and 7.29–7.38 (4H,m); M$^+$ 168.

PREPARATION 12

1-[N-(t-Butyloxycarbonyl)-N-(cyclopentyl)amino]-4-thiopyridone a) 1-[N-(t-Butyloxycarbonyl)-N-(cyclopentyl)-amino]- 4-pyridone 1-(t-Butyloxycarbonylamino)-4-pyridone (0.2 g, 0.94 mmol) in N,N dimethylformamide (4 ml) was treated successively with potassium carbonate (0.128 g, 0.94 mmol) and 1-iodocyclopentane (0.184 g, 0.94 mmol). The reaction mixture was stirred at room temperature for 3 h and evaporated under reduced pressure. Purification on silica gel 60 eluting with ethanol, dichloromethane (1:9) gave the title compound (0.109 g, 41%) $\delta_H$ (CDCl$_3$), 1.45 (9H,s), 1.5–2.07 (8H,m), 4.5–4.62 (1H,m), 6.4 (2H,d, J 8Hz) and 7.2 (2H,d, J 8Hz); M$^+$ 278.

b) 1-[N-(t-Butyloxycarbonyl)-N-(cyclopentyl)-amino]- 4-thiopyridone

The product of Preparation 12(a) (0,104 g, 0.37 mmol) in toluene (10 ml) was treated with Lawesson's reagent (0.15 g, 0.37 mmol) and heated at 80° C. for 0.5 h under Argon. The mixture was allowed to cool and chromatographed on silica gel 60 eluting with ethanol, dichloromethane mixtures to give the title compound (0.042 g, 37%); $\delta_H$ (CDCl$_3$) inter alia 1.45 (9H,s), 1.5–2.25 (8H,m), 4.5–4.65 (1H,m), 7.25 and 7.6 (4H, 2 s); M$^+$ 294.

PREPARATION 13

1-[N-(t-Butyloxycarbonyl)-N-(prop-2-en-1-yl)amino]-4-thiopyridone a) 1-[N-(t-Butyloxycarbonyl)-N-(prop-2-en-1-yl)-amino]- 4-pyridone 1-(t-Butyloxycarbonylamino)-4-pyridone (0.2 g, 0.94 mmol) in N,N dimethylformamide (3 ml) was treated successively with potassium carbonate (0.31 g, 0.95 mmol) and allyl bromide (0,114 g, 0.94 mmol). The reaction mixture was stirred for 1 h and evaporated under reduced pressure. Purification on silica gel 60 eluting with ethanol, dichloromethane (1:9) gave the title compound (0,185 g, 78%); identical to the product in Preparation 9(a).

b) 1-[N-(t-Butyloxycarbonyl)-N-(prop-2-en-1-yl)-amino] -4-thiopyridone

The product of Preparation 13(a) (0,185 g, 0.74 mmol) in toluene (15 ml) was treated with Lawesson's reagent (0,225 g, 0.56 mmol) and heated at 80° C. for 0.5 h. The mixture was allowed to cool and chromatographed on silica gel 60 eluting with ethanol, dichloromethane mixtures to give the title compound (0.09 g, 46%); identical to the product of Preparation 9(b).

PREPARATION 14

1-[N-Butyl-N-(t-butyloxycarbonyl)amino]-4-thiopyridone a) 1-[N-Butyl-N-(t-butyloxycarbonyl)amino]-4-pyridone 1-(t-Butyloxycarbonylamino)-4-pyridone (0.1 g, 0.47 mmol) in N,N dimethylformamide (2 ml) was treated successively with potassium carbonate (0.66 g, 0.47 mmol) and -bromobutane (0,065 g, 0.47 mmol). This mixture was stirred for 4 h and then evaporated under reduced pressure. Purification on silica gel 60 eluting with ethanol, dichloromethane (1:9) gave the title compound (0.088 g, 70%); $\delta_H$ (CDCl$_3$) 0.96 (3H,t, J 7Hz), 1.3–1.64 (4H,m), 1.45 (9H,s) 3.66 (2H,t, J 7Hz), 6.32 (2H,d, J 7Hz), 7.21 (2H,d, a 7Hz); M$^+$ 266.

b) 1-[N-Butyl-N-(t-butyloxycarbonyl)amino]-4-thiopyridone

The product of Preparation 14(a) (0,088 g, 0.33 mmol) in toluene (10 ml) was treated with Lawesson's reagent (0.13 g, 0.32 mmol) and heated at 80° C. for 0.5 h. The mixture was allowed to cool and chromatographed on silica gel 60 eluting with ethanol, dichloromethane (1:9) to give the title compound (0.053 g, 57%); $\delta_H$ (CDCl$_3$) 0.95 (3H,t, J 7Hz) 1.25–1.63 (4H ,m ), 1.45 (9H, s), 3.67 (2H, t, J 7.5Hz), 7.02 (2H, d, J 7.5Hz ), and 7.40 (2H,d, J 7.5Hz); M$^+$ 282.

PREPARATION 15

1-[N-(t-Butyloxycarbonyl)-N-hexylamino]-4-thiopyridone a) 1-[N-(t-Butyloxycarbonyl)-N-hexylamino]-4-pyridone 1-(t-Butyloxycarbonyl amino)-4-pyridone (0.2 g, 0.94 mmol) in N, N dimethylformamide (4 ml) was treated successively with potassium carbonate (0,132 g, 0.95 mmol) and 1-bromohexane (0,203 g, 1.22 mmol). The mixture was stirred for 18 h and then evaporated under reduced pressure. Purification on silica gel 60 eluting with ethanol, dichloromethane (1:9) $\delta_H$ (CDCl$_3$) 0.89 (3H,t, J 6Hz), 1.21–1.76 (17H, m), 3.65 (2H,t, J 7.5Hz), 6.35 (2H,d, J 8Hz), and 7.21 (2H,d, J 8Hz); M$^+$ 294.

b) 1-[N-(t-Butyloxycarbonyl)-N-hexylamino]-4-thiopyridone

The product of Preparation 15(a) (0.28 g, 0.95 mmol) in toluene (10 ml) was treated with Lawesson's reagent (0.38 g, 0.94 mmol) and heated at 80° C. for 35 minutes. The mixture was allowed to cool and chromatographed on silica gel 60 eluting with ethanol, dichloromethane (1:9) to give the compound (0.179 g, 66% ); $\delta_H$ (CDCl$_3$) 0.89 (3H,t,J 6Hz), 1.23–1.70 (8H,m), 1.45 (9H,s), 3.67 (2H, t, J7.5Hz), 7.02 (2H, d, J 7Hz), and 7.4 (2H, d,J 7Hz) M⁺ 310.

PREPARATION 16

1-[N-(t-Butyloxycarbonyl)-N-(1-isopropyl)amino]-4-thiopyridone a) 1-[N-(t-Butyloxycarbonyl)-N-(1-isopropyl)-amino]-4-pyridone 1-(t-Butyloxycarbonyl amino)-4-pyridone (0.2 g, 0.94 mmol) in N,N dimethylformamide (4 ml) was treated successively with potassium carbonate (0.132 g, 0.95 mmol) and 2-bromopropane (0.152 g, 1.22 mmol). The mixture was stirred for 24 h and then evaporated under reduced pressure. Purification on silica gel 60 eluting with ethanol, dichloromethane (1:9) gave the title compound (0.116 g, 49%); $\delta_H$ (CDCl$_3$) 1.21 (6H,d, J 7Hz), 1.44 (9H,s), 4.61 (1H,t, J 7Hz), 6.33 (2H,d, J 8Hz) and 7.15 (2H,d, J 8Hz); M⁺ 252.

b) 1-[N-(t-Butyloxycarbonyl)-N-(1-isopropyl)-amino]-4-thiopyridone

The product of Preparation 16(a) (0.116 g, 0.46 mmol) in toluene (10 ml) was treated with Lawesson's reagent (0.124 g, 0.31 mmol) and heated at 80° C. for 35 minutes. The mixture was allowed to cool and chromatographed on silica gel 60 eluting with ethanol, dichloromethane (1: 9) to give the title compound (0.05 g, 41%); $\delta_H$ (CDCl$_3$) 1.22 (6H, d, J 7Hz), 1.45 (9H,s), 4.65 (1H,t, J 7Hz), 6.96 (2H, d, J 7Hz), and 7.38 (2H, d, J 7Hz) M⁺ 268.

PREPARATION 17

1-[N-(t-Butyloxycarbonyl)-N-(2-hydroxyethyl)amino]-4-thiopyridone a) N-(t-Butyloxycarbonyl)-N-(2-hydroxyethyl)-hydrazine 2-Hydroxyethylhydrazine (0.228 g, 3.0 mmol) in dichloromethane (10 ml) was treated with di-t-butyldicarbonate (0.65 g, 3.0 mmol). The reaction mixture was stirred for 0.75 h and then evaporated under reduced pressure. Purification on silica gel 60 eluting with ethanol, dichloromethane (1:9) gave the title compound (0.413 g, 78%); $\delta_H$ (CDCl$_3$) 1.48 (9H,s), 3.58 (2H,t, J 4.5Hz) 3.83 (2H, t, J 4.5Hz), and 3.3–4.0 (1H, brs).

b) 1-[N-(t-Butyloxycarbonyl)-N-(2-hydroxyethyl)-amino]-4-thiopyridone

N-(t-Butyloxycarbonyl)-N-(2-hydroxyethyl)hydrazine (0.413 g, 2.37 mmol) in ethanol (10 ml) was treated with 4-thiopyranone (0.16 g 1.43 mmol). The mixture was stirred at 60° C. for 18 h, then allowed to cool and evaporated under reduced pressure. Purification on silica gel 60 eluting with ethanol, dichloromethane (1:9) gave the title compound (0.351 g, 91%); $\delta_H$ (CDCl$_3$), 1.47 (9H,s), 3.30–3.95 (5H,m), and 7.32 (4H,d, J 5Hz); M⁺ 270.

PREPARATION 18

2-[(Z)-[S]-(3,4-Diacetoxyphenyl)(diphenylmethyloxycarbonyl)methyloxyimino]-2-(2-tritylamino-4-thiazolyl)acetic acid and 2-[(Z)-[R]-(3,4-Diacetoxyphenyl)(diphenylmethyloxycarbonyl)methyloxyimino]-2-(2-tritylamino-4-thiazolyl)acetic acid a) R-(+)-α-Methylbenzylamine salt of [S]-2-(3,4-diacetoxyphenyl)-2-(phthalimidooxy)acetic acid and S-(−)-α-methylbenzylamine salt of [R]-2-(3,4-diacetoxyphenyl)-2-(phthalimidooxy)acetic acid Diphenylmethyl [RS]-2-(3,4-diacetoxyphenyl)-2-(phthalimidooxy)acetate (3.8 g, 6.56 mmol) was dissolved in dichloromethane (100 ml), treated with trifluoroacetic acid (10 ml) and stirred for 2 h. The mixture was diluted with toluene (50 ml) and evaporated to dryness under reduced pressure. The residue was triturated under hexane (2×200 ml) and then dissolved in acetone (30 ml). The resulting solution was treated with R-(+)-α-methylbenzylamine (0.84 ml, 6.53 mmol) and, after 30 minutes the solid was collected by filtration and washed with acetone, to give the R-(+)-α-methylbenzylamine salt of [S]-2-(3,4-diacetoxyphenyl)-2-(phthalimidooxy)acetic acid (1.05 g, 60%); $[a]_D^{21}$ +189° (c 0.05 in EtOH); $\delta_H$ (CDCl$_3$) 1.48 (3H, d, J 6Hz), 2.19 (3H, s), 2.23 (3H, s), 4.25 (1H, q, J 6Hz), 5.76 (1H, s), 7.00–7.50 (8H, m), and 7.60–7.70 (4H, s). The filtrate from above was evaporated under reduced pressure and partitioned between dilute hydrochloric acid and ethyl acetate. The ethyl acetate layer was dried (MgSO$_4$) and evaporated to dryness under reduced pressure. The residue was dissolved in acetone (15 ml) and treated with S-(−)-α-methylbenzylamine (0.69 ml, 5.3 mmol). After 30 minutes the solid was collected by filtration and washed with acetone to give the S-(−)-α-methylbenzyl amine salt of [R]-2-(3,4-diacetoxyphenyl)-2-(phthalimidooxy)acetic acid (1.07 g, 67%); $[a]_D^{21}$ −184° (c 0.04 in EtOH); $\delta_H$ (CDCl$_3$) 1.50 (3H, d, J 6 Hz), 2.21 (3H, s), 2.24 (3H, s), 4.28 (1H, q, J 6 Hz), 5.78 (1H, s), 7.05–7.50 (8H, m), and 7.70 (4H, s).

b) Diphenylmethyl [S]-2-(3,4-diacetoxyphenyl)-2-(phthalimidooxy)acetate

R-(+)-α-Methylbenzylamine salt of [S]-2-(3,4-diacetoxyphenyl)- 2-(phthalimidooxy)acetic acid (1.31 g, 2.45 mmol) was partitioned between dilute hydrochloric acid and ethyl acetate. The ethyl acetate later was dried and treated with an excess of diphenyldiazomethane. The solution was evaporated under reduced pressure and the residue purified by chromatography on silic gel 60, eluting with mixtures of hexane and ethyl acetate, to give the title compound (1.4 g, 98%); $\delta_H$ (CDCl$_3$), 2.21 (6H, s), 6.00 (1H, s), 6.87 (1H, s), 7.00–7.60 (13H, m), and 7.65–7.75 (4H, m).

c) 2-[(Z)-[S]-(3,4-Diacetoxyphenyl)(diphenylmethyloxycarbonyl)methyloxyimino]-2-(2-tritylamino-4-thiazolyl)acetic acid Diphenylmethyl [S]-2-(3,4-diacetoxyphenyl)-2-(phthalimidooxy)acetate (1.36 g, 2.35 mmol) was dissolved in dichloromethane (25 ml) and cooled to −60° C. This solution was treated with methylhydrazine (0.125 ml, 2.35 mmol) and the temperature allowed to rise slowly to +5° C. The mixture was then stirred at ambient temperature for 1 h. The solid was removed by filtration and the filtrate evaporated to dryness under reduced pressure. The residue was dissolved in methanol (40 ml) and treated with 2-(2-tritylamino-4-thiazolyl)glyoxylic acid (0.95 g, 2.3 mmol). After 2 h, the reaction mixture was evaporated to dryness under reduced pressure. Chromatography on silica gel 60, eluting with mixtures of dichloromethane and ethanol gave the title compound (1.15 g, 58%); $\delta_H$ (CDCl$_3$) 2.27 (3H, s), 2.29 (3H, s), 6.00 (1H, s), 6.76 (1H, s), 6.85 (1H, s), and 6.90–7.40 (29H, m).

d) 2-[(Z)-[R]-(Diacetoxyphenyl)(diphenylmethyloxycarbonyl)methyloxyimino]-2-(2-tritylamino-4-thiazolyl) acetic acid This was prepared from the [S]-(−)-α-methylbenzylamine salt of [R]-2-(3,4-diacetoxyphenyl)-2-(phthalimidooxy)acetic acid (1.20 g, 2.28 mmol) as described in Preparation 18 (b) and (c) (0.91 g, 47%), $\delta_H$ (CDCl$_3$), 2.27 (3H, s), 2.29 (3H, s), 6.01 (1H, s), 6.79 (1H, s), 6.85 (1H, s), and 6.90–7.40 (29H, m).

PREPARATION 19

1-(t-Butyloxycarbonylamino)-2,3-cyclopenteno-4-thiopyridone a) 2,3-Cyclopenteno-4-thiopyranone 2,3-Cyclopenteno-4-pyranone (0.56 g, 4.12 mmol) (G. J äger, *Justus Liebigs Ann. Chem.*, 1976, 1689–1712) in toluene (30 ml) was heated at 80° C. with Lawessons reagent (1.67 g, 4.13 mmol) under Argon and stirred for 40 minutes, then allowed to cool and chromatographed on silica gel 60 eluting with dichloromethane to give the title compound (0.506 g, 81%); $\delta_H$ [(CD$_3$)$_2$CO] 2.0–2.16 (2H, m), 2.7–2.81 (2H, m), 2.81–3.0 (2H, m), 7.00 (1H, d, J 5.34), and 7.83 (1H, d, J 5.33); MH$^+$ 153.

b) 1-(t-Butyloxycarbonylamino)-2,3-cyclopenteno-4-thiopyridone 2,3-Cyclopenteno-4-thiopyranone (0.125 g, 0.82 mmol) in ethanol (8 ml) was treated with t-butylcarbazate (0.108 g, 0.82 mmol) and heated at reflux under Argon for 4 days. The solvent was evaporated under reduced pressure and the residue chromatographed on silica gel 60 eluting with ethanol, dichloromethane (1:9) to give the title compound (0.083 g, 38%); $\delta_H$ (CDCl$_3$) 1.4–1.63 (9H, m), 2.05–2.20 (2H, m), 2.68–3.08 (4H, m), 7.04 (1H, d, J 7Hz), and 7.11 (1H, d, J 7Hz); M$^+$ 266.

PREPARATION 20

1-(2-Pyridylamino)-4-thiopyridone

4-Thiopyranone (0.112 g, 1 mmol) and 2-hydrazinopyridine (0.109 g, 1 mmol) in ethanol (5 ml) was heated at reflux for 7 h, cooled, evaporated to dryness and the residue chromatographed to afford the title compound (0.035 g, 17%); $\upsilon_{max}$ (KBr) 3430, 1616 and 1572cm$^{-1}$; $\delta_H$ (CDCl$_3$ (CD$_3$)$_2$SO) 6.5 9 (1H, d, J 8.3Hz), 6.91 (1H, dd, J 6.6 and 7.6Hz), 7.3 3 and 7.42 (4H, 2ABq, J 7.2Hz), 7.58 (1H, m), 8.18 (1H, d, J 4.6 Hz), and 10.12 (1H, br s, exch.); M$^+$ 203.

PREPARATION 21

1-(3.,5-Dimethylisoxazol-4-yl)methylamino-4-thiopyridone a) 1-[N-(t-Butyloxycarbonyl)-N-[(3,5-dimethylisoxazol-4-yl)methyl]amino]-4-pyridone 1-(t-Butyloxycarbonylamino)-4-pyridone (0.105 g, 0.5 mmol) in N,N-dimethylformamide (2.5 ml) containing 4-chloromethyl-3,5-dimethylisoxazole (0.072 g, 0.5 mmol) was treated with powdered potassium carbonate (0.07 g, 0.5 mmol). The reaction was stirred for 2 h, diluted with dichloromethane (20 ml) and washed with water (x2), brine, dried (Na$_2$SO$_4$) and evaporated. The residue was chromatographed to afford the title compound (0.142 g, 90%); $\upsilon_{max}$ (KBr) 1718, 1646, 1628 and 1586cm$^{-1}$; $\delta_H$ (CDCl$_3$) 1.47 (9H, s), 2.18 (3H, s), 2.20 (3H, s), 4.62 (2H, s), 6.29 (2H, d, J 7.8Hz), and 6.96 (2H, d, J 7.8Hz); M$^+$ 319.

b) 1-[N-(t-Butyloxycarbonyl)-N-[(3,5-dimethylisoxazol-4-yl)methyl]amino]-4-thiopyridone To a solution of the product from preparation 21(a) (0.133 g, 0.42 mmol) in dry toluene (5 ml) at 80° C. was added Lawessons reagent (0.084 g, 0.21 mmol). The mixture was stirred for 20 minutes, cooled and the solution decanted and chromatographed on silica gel to afford the title product (0.90 g, 64%); $\upsilon_{max}$ (KBr) 1728, and 1616cm$^{-1}$; $\delta_H$ (CDCl$_3$) 1.47 (9H, s), 2.18 (3H, s), 2.19 (3H, s), 4.63 (2H, s), 6.76 (2H, d, J 7.4Hz), and 7.31 (2H, d, J 7.4 Hz); M$^+$ 335.

c) 1-(3,5-Dimethylisoxazol-4-yl)methylamino-4-thiopyridone

To the product from preparation 21(b) (0.083 g, 0.35 mmol) in dichloromethane (5.2 ml) was added trifluoroacetic acid (0.57 ml, 10.5 mmol) and the mixture stirred for 3 h. The solution was evaporated to low volume and added dropwise to vigorously stirred ether (50 ml). The precipitate was filtered off, washed with ether and dried in vacuo to afford the title product (0.033 g, 574); $\upsilon_{max}$ (KBr) 1611 and 1530cm$^{-1}$; $\delta_H$ (CDCl$_3$+(CD$_3$)$_2$SO) 2.18 (3H, s), 2.24 (3H, s), 3.95 (2H, s), 7.31 (2H, d, J 7 Hz), and 7.38 (2H, d, J 7 Hz); M$^+$ 235.

PREPARATION 22

1-(N-Acetyl-N-methylamino)-4-thiopyridone 1-(Methylamino)-4-thiopyridone (0.21 g, 1.5 mmol) in dichloromethane (20 ml) was treated with triethylamine (0.21 ml, 1.5 mmol) and then acetic anhydride (0.15 ml, 1.6 mmol) and stirred for 5 minutes. The product was obtained by purification on silica gel 60 eluting with 20% ethanol in dichloromethane (0.17 g, 62%); $\nu_{max}$ (CH$_2$Cl$_2$) 1700 and 1615 cm$^{-1}$; δH (CDCl$_3$) 2.02 (3H, s), 3.40 (3H, s), 7.08 (2H,d, J 7.5 Hz), and 7.41 (2H, d, J 7.5 Hz); M$^+$ 182.

PREPARATION 23

1-[N-Methyl-N-(4-nitrobenzoyl)amino]-4-thiopyridone

1-Methylamino-4-thiopyridone (0.05 g, 0.36 mmol) in dichloromethane (2 ml) was treated with triethylamine (0.05 ml, 0.36 mmol) followed by p-nitrobenzoyl chloride (0.066 g, 0.36 mmol) dissolved in dichloromethane (5 ml) and stirred for 0.5h. Purification on silica gel 60 eluting with methanol and dichloromethane mixtures gave the title compound (0.092 mg, 89%); δH [(CD$_3$)$_2$SO] 3.36 (3H, s), 7.8 (2H, brs), 7.96 (2H, s), 7.99 (2H, s), and 8.35 (2H, brs); M$^+$ 289.

PREPARATION 24

1[N-(4-Methoxybenzoyl)-N-methylamino]- 4-thiopyridone

Reaction of 1-methylamino-4-thiopyridone (0.078 g, 0.56 mmol), triethylamine (0.056 g, 0.56 mmol) and p-anisoyl chloride (0.095 g, 0.56 mmol) in tetrahydrofuran (25 ml) for 0.5h followed by purification on silica gel 60 eluting with mixtures of methanol and dichloromethane gave the title compound (0.148 g, 96%); ν$_{max}$ (CHCl$_3$) 1670 and 1615cm$^{-1}$; δH (CDCl$_3$) 3.49 (3H, s), 3.80 (3H, s), 6.86 (2H, d, J 8 Hz), 7.11 and 7.3 (4H, 2d, J 7 Hz), and 7.44 (2H, d, J 8 Hz); M$^+$ 274.

PREPARATION 25

1-[N-(2-Furoyl)-N-methylamino]-4-thiopyridone

Reaction of 1-methylamino-4-thiopyridone (0.090 g, 0.64 mmol), triethylamine (0.09 ml, 0.64 mmol) and 2-furoyl chloride (0.084 g, 0.64 mmol) in dichloromethane (15 ml) for 0.5h followed by purification on silica gel 60 eluting with mixtures of methanol, dichloromethane gave the title compound (0.138 g, 92%); ν$_{max}$ (CHCl$_3$) 1660 and 1615 cm$^{-1}$; δH (CDCl$_3$/CD$_3$OD) 3.55 (3H, s), 6.46 (1H, dd, J 2 and 4 Hz), 6.90 (1H, d, J 4 Hz), 7.29 (2H, s), 7.38 (2H, s), and 7.45 (1H, brs); M$^+$ 234.

PREPARATION 26

1-[N-[3,4-bis(4-Methoxybenzyloxy)benzoyl]-N-methylamino]- 4-thiopyridone a) 4-Methoxybenzyl 3,4-bis(4-methoxybenzyloxy)benzoate.

3,4-Dihydroxybenzoic acid (3.08 g, 0.02 mol) was dissolved in N,N-dimethylformamide (50 ml) and treated with 4-methoxybenzyl chloride (10 ml, 0.07 mol) and potassium carbonate (10 g, 0.07 mol). The mixture was warmed to 60° C. for 6h and then stirred overnight. The mixture was partitioned between water and ethyl acetate. The organic phase was washed exhaustively with water and then the product was purified on silica gel 60 eluting with mixtures of ethyl acetate and hexane to give the title compound (6.48 g, 63%).

b) 3,4-bis(4-Methoxybenzyloxy)benzoic acid.

4-Methoxybenzyl 3,4-bis(4-methoxybenzyloxy)benzoate (6.48 g, 0.013 mol) was suspended in ethanol and treated with 2.5N aqueous sodium hydroxide solution (7.6 ml, 0.015 mol). The mixture was warmed to 60° C. for 4h. The mixture was evaporated to low volume and then partitioned between water and ethyl acetate. The aqueous layer was washed again with ethyl acetate and then acidified and extracted into ethyl acetate. As the ethyl acetate solution was concentrated the product precipitated from solution and was filtered off to give the title compound (4.36 g, 87%).

c. N-[3,4-bis(4-Methoxybenzyloxy)benzoyl]-N-methylhydrazine.

3,4-bis-(4-Methoxybenzyloxy)benzoic acid (0.792 g, 2.0 mmol) was dissolved in dichloromethane (20 ml) and treated with N,N-diisopropylethylamine (0.35 ml, 2.0 mmol). The solution was cooled to −40° C. and treated with methanesulphonyl chloride (0.15 ml, 2.0 mmol). The mixture was allowed to warm to room temperature for 10 minutes and then re-cooled to −40° C. and added to a solution of methylhydrazine (0.215 ml, 4 mmol) in dichloromethane (10 ml) at −40° C. The mixture was allowed to warm to room temperature for 1.5h and then evaporated to dryness under reduced pressure. The residue was dissolved in ethyl acetate which was washed with water and brine. Evaporation of the solvent gave the title compound (0.823 g, 94%); δ$_H$ (CDCl$_3$) 3.08 (3H, s), 3.74 (6H, s), 4.25 (2H, brs), 5.03 (4H, s), and 6.70–7.40 (11H, m).

d) 1-[N-[3,4-bis(4-Methoxybenzyloxy)benzoyl]-N-methylamino]- 4-thiopyridone

N-[3,4-bis-(4-Methoxybenzyloxy)benzoyl]-N-methylhydrazine (0.80 g, 1.8 mmol) was heated at reflux in ethanol (60 ml) with 4-thiopyranone (0.224 g, 2.0 mmol) for 48 hours. After evaporation under reduced pressure, purification on silica gel 60 gave the title compound (0.404 g; 43%); ν$_{max}$. (KBr) 1656, 1612, and 1513 cm$^{-1}$; δH (CDCl$_3$) 3.40 (3H, s), 3.88 (6H, s), 5.02 (2H, s), 5.07 (2H, s), 6.90–7.30 (7H, m), 6.85 (2H, d), J 9 Hz), and 7.30 (2H, d, J 9 Hz); M$^+$ 516.

PREPARATION 27

1-(N-Benzoyl-N-methylamino)-4-thiopyridone a) N-Benzoyl-N-methylhydrazine

Methylhydrazine (0.212 ml, 4.0 mmol) was dissolved in dichloromethane (10 ml) and was treated dropwise with benzoylchloride (0.232 ml, 2.0 mmol) in dichloromethane (5 ml). After stirring for 0.5h the solution was evaporated to dryness. The residue was partitioned between water and ethyl acetate. The organic phase was dried and evaporated under reduced pressure to give the title compound (0.20 g, 65%); δ$_H$ (CDCl$_3$) 3.13 (3H, s), 4.5 (2H, brs), and 7.30 (5H, s).

b) 1-(N-Benzoyl-N-methylamino)-4-thiopyridone.

N-Benzoyl-N-methylhydrazine (0.20 g, 1.3 mmol) in ethanol (10 ml) was heated at reflux for 28h with 4-thiopyranone (0.15 g, 1.3 mmol). The solvent was evaporated and the product purified by chromatography on silica gel eluting with mixtures of ethyl acetate and hexane to give the title compound (0.114 g, 36%); δH (CDCl$_3$) 3.50 (3H, s), 7.09 (2H, d, J 8 Hz), 7.12 (2H, d, J 8 Hz), and 7.43 (5H, s).

PREPARATION 28

1-[N-[3,4-bis(4-Methoxybenzyloxy)cinnamoyl-N-methylamino]- 4-thiopyridone a) N-[3,4-bis(4-Methoxybenzyloxy)cinnamoyl]-N-methylhydrazine The title compound was obtained by the method of Preparation 26 using 3,4-dihydroxycinnamic acid in place of 3,4-dihydroxybenzoic acid; δ$_H$ (CDCl$_3$) 3.25 (3H, s), 3.86 (6H, s), 3.95 (2H, brs), 5.05 (4H, s), and 6.65–6.80 (13H, m).

b) 1-[N-[3,4-bis(4-Methoxybenzyloxy)cinnamoyl]-N-methylamino]- 4-thiopyridone

N-[3,4-bis(4-Methoxybenzyloxy)cinnamoyl]-N-methylhydrazine (0.225 g, 0.54 mmol) in ethanol (15 ml) containing 4-thiopyranone (0.056 g, 0.48 mmol) was heated at reflux for 96h. Purification on silica gel 60 eluting with mixtures of ethyl acetate and hexane gave the title compound (0.86 g, 35%); δ$_H$ (CDCl$_3$) 3.36 (3H, s), 3.74 (6H, s), 4.98 (2H, s), 5.02 (2H, s), 5.94 (1H, d, J 15 Hz), 6.75–7.45 (15H, m), and 7.63 (1H, d, J 15 Hz).

PREPARATION 29

1-Ureido-4-thiopyridone

4-Thiopyranone (0.265 g, 2.37 mmol), semicarbazide hydrochloride (0.265 g, 2.37 mmol), and triethylamine (0.4 ml, 5.4 mmol) in ethanol (20 ml), were heated at reflux for 24h then cooled. The white precipitate was filtered off, washed with ethanol and then dried in vacuo to give the title compound (0.224 g, 60%); $\delta_H$ [(CD$_3$)$_2$SO], 6.62 (2H, brs), 7.13 (2H, d, J 9 Hz), and 7.51 (2H, d, J 9 Hz).

PREPARATION 30

1-(1,3-Dimethylureido)-4-thiopyridone

4-Thiopyranone (0.267 g, 2.38 mmol) and 1,3-dimethylsemicarbazide (0.245 g, 2.38 mmol) were heated at reflux in ethanol (10 ml) for 45h. The mixture was evaporated and the residue was purified on silica gel 60 eluting with dichloromethane, methanol mixtures to give the title compound as a white solid (0.333 g, 71%); m/z (F.A.B., thioglycerol) M$^+$ 197.

PREPARATION 31

1-(1-Methylureido)-4-thiopyridone

4-Thiopyranone (0.143 g, 1.28 mmol) and 2-methylsemicarbazide (0.114 g, 1.28 mmol) were heated at reflux in ethanol (10 ml) for 48h. The reaction mixture was evaporated and the residue was purified on silica gel 60 eluting with acetone to give the title compound as a white solid (0.031 g, 13%); $\delta_H$ [(CD$_3$)$_2$SO] 3.27 (3H, s), 6.74 (2H, s, exch. with D$_2$O), 7.13 (2H, d, J 6 Hz), and 7.69 (2H, d, J 6 Hz).

PREPARATION 32

1-(2-Oxopyrrolidin-1-yl)-4-thiopyridone

1-Amino-2-oxopyrrolidine (0.184 g, 2 mmol) and 4-thiopyranone (0.224 g, 2 mmol) were heated at reflux in ethanol (25 ml) and under argon for 24h. The volatiles were removed under reduced pressure and the residue purified on silica gel 60 eluting with dichloromethane then mixtures of ethyl acetate and hexane, to give the title compound (0.227 g, 58%); $\nu_{max}$ (CH$_2$Cl$_2$) 1725 and 1612 cm$^{-1}$; $\delta_H$ (CDCl$_3$) 2.16–2.70 (4H, m), 3.87 (2H, t, J 7 Hz), 7.10–7.50 (4H, m); (Found: M$^+$, 194.0512. C$_9$H$_{10}$N$_2$OS requires M, 194.0514).

PREPARATION 33

1-(2-Oxopiperidin-1-yl)-4-thiopyridone

1-Amino-2-oxopiperidine (0.228 g, 2 mmol) and 4-thiopyranone (0.23 g, 2 mmol) in ethanol (25 ml) were heated at reflux for 3.5h. The volatiles were removed under reduced pressure and the residue purified on silica gel 60, eluting with dichloromethane then ethyl acetate, to give the title compound (0.264 g, 68%); $\nu_{max}$ (CH$_2$Cl$_2$) 1690, 1610 and 1115 cm$^{-1}$; $\delta_H$ (CDCl$_3$) 1.80–2.30 (4H, m), 2.59 (2H, t, J 7 Hz), 3.8 (2H, t, J 7 Hz), and 7.15–7.40 (4H, m); (Found: M$^+$, 208.0669. C$_{10}$H$_{12}$N$_2$OS requires M, 208.0670).

PREPARATION 34

1-[N-(4-Diphenylmethoxycarbonylbenzoyl)-N-methylamino]- 4-thiopyridone 4-(Diphenylmethoxycarbonyl)benzoic acid (0.161 g, 0.5 mmol) was dissolved in dry dichloromethane (20 ml) and treated with oxalyl chloride (0.1 ml, 1.15 mmol) and N,N-dimethylformamide (0.01 ml). After 1h, the reaction mixture was evaporated to dryness under reduced pressure. The residue was redissolved in dry dichloromethane (10 ml) and added to a solution of 1-(methylamino)-4-thiopyridone (0.07 g, 0.5 mmol) and triethylamine (0.0505 g, 0.5 mmol) in acetonitrile (10 ml). After 15 minutes at room temperature, the volatiles were removed under reduced pressure and the residue purified on silica gel 60, eluting with dichloromethane then ethyl acetate, to give the title compound (0.185 g, 81%); $\nu_{max}$ (KBr) 1715, 1677 and 1615 cm$^{-1}$; $\delta_H$ [(CD$_3$)$_2$SO] 5.44 (3H, s), 7.05 (1H, s), 7.24–7.59 (16H, m), and 7.96 (2H, d, J 7 Hz); (Found: M$^+$ 454.1358. C$_{27}$H$_{22}$N$_2$O$_3$S requires M, 454.1351).

PREPARATION 35

1-[N-[4-(t-Butoxycarbonylamino)benzoyl]-N-methylamino]- 4-thiopyridone

1-[4-(t-Butyloxycarbonylamino)benzoyl]-1-methylhydrazine (0.205 g, 0.77 mmol) and 4-thiopyranone (0.087 g, 0.78 mmol) were heated at reflux in ethanol (20 ml) for 16h, then the mixture left to stand at room temperature for 90h. The volatiles were removed under reduced pressure and the residue purified on silica gel 60, eluting with dichloromethane then mixtures of ethyl acetate and hexane, to give the title compound (0.09 g, 32%); $\nu_{max}$ (KBr), 1725, 1670 and 1612 cm$^{-1}$; $\delta_H$ (CDCl$_3$+ CD$_3$OD) 1.51 (9H, s), 3.52 (3H, s), 7.35–7.50 (8H, m), and 8.48 (1H, brs, exch.) (Found: M$^+$, 359.1311. C$_{18}$H$_{21}$N$_3$O$_3$S requires M, 359.1304).

PREPARATION 36

4-Methoxybenzyl [6R,7R]-7-amino-3-[1-(methylamino)pyridinium-4-thiomethyl]ceph-3-em-4-carboxylate iodide 4-Methoxybenzyl [6R,7R]-7-amino-3-(chloromethyl)ceph- 3-em-4-carboxylate hydrochloride (2.4 g, 6 mmol) was partitioned between dilute, aqueous sodium hydrogen carbonate and ethyl acetate. The organic phase was washed with brine and evaporated to dryness under reduced pressure. The residue was dissolved in acetonitrile (20 ml) and treated with sodium iodide (0.75 g, 5 mmol). After 5 minutes 1-(methylamino)- 4-thiopyridone (0.7 g, 5 mmol) was added and the mixture stirred for 1.5h. The mixture was filtered into vigorously stirred diethylether (500 ml) and the product collected by filtration (2.2 g, 72%); $\nu_{max}$ (KBr) 1772, 1718, 1618, and 1513 cm$^{-1}$; $\delta_H$ (CDCl$_3$) 3.07 (3H, d, J 6 Hz), 3.49 and 3.73 (2H, ABq, J 18 Hz), 3.81 (3H, s), 4.29 and 4.45 (2H, ABq, J 13 Hz), 4.79 (1H, d, J 5 Hz), 4.97 (1H, d, J 5 Hz), 5.20 and 5.28 (2H, ABq, J 12 Hz), 6.87 (2H, d, J 8.5 Hz), 7.36 (2H, d, J 8.5 Hz), 7.73 (2H, d, J 7 Hz), 8.51 (1H, q, J 6 Hz, exch.), and 8.89 (2H, d, J 7 Hz); m/z (F.A.B., thioglycerol) M$^+$ 473.

PREPARATION 37

2-(Z)-[3,4-(Methylenedioxy)benzyloxyimino]-2-(2-tritylamino- 4-thiazolyl)acetic acid 2-(2-Tritylamino-4-thiazolyl)glyoxylic acid (1.61 g, 3.89 mmol) was suspended in methanol (50 ml) and treated with 3,4-(methylenedioxy)benzyloxyamine (0.65 g, 3.89 mmol). After 2h, the volatiles were removed under reduced pressure and the residue partitioned between ethyl acetate (50 ml) and saturated, aqueous sodium hydrogen carbonate solution (50 ml). The phases were separated, the aqueous phase was washed with ethyl acetate (50 ml) and acidified with 5M hydrochloric acid in the presence of ethyl acetate (50 ml). The phases were separated and the organic phase washed with water (20 ml), saturated brine (20 ml), dried over anhydrous magnesium sulphate and evaporated to dryness under reduced pressure to give the title compound (2.01 g, 92%); $v_{max}$ (KBr) 1731 cm$^{-1}$; $\delta_H$ [(CD$_3$)$_2$CO] 5.04 (2H, brs), 6.94 (2H, s), 6.79–6.95 (4H, m), and 7.18–7.50 (15H, m); m/z (F.A.B., 3-nitrobenzyl alcohol/sodium acetate) MNa$^+$ 586.

PREPARATION 38

1-(t-Butyloxycarbonylamino)-5-methoxy-2-(methoxymethyl)- 4-thiopyridone a) 5-Methoxy-2-(methoxymethyl)-4-thiopyranone 5-Methoxy-2-(methoxymethyl)-4-pyranone (3.24 g, 19 mmol) (K. Heyns and G. vogelsang, *Chem. Ber.* 1954, 87, 1377) in toluene (60 ml) was heated at 80° C. with Lawessons reagent (4.23 g, 10 mmol) for 2h. After cooling the reaction mixture was chromatographed on silica gel 60 eluting with toluene/ethyl acetate mixtures to give the title compound (3.54 g, 100%); $v_{max}$ (CH$_2$Cl$_2$) 3050, 2950, 2830, 1625, and 1560 cm$^{-1}$; $\delta_H$ (CDCl$_3$) 3.4 (3H, s), 3.8 (3H, s), 4.2 (2H, s), 7.3 (1H, s), 7.4 (1H, s); M$^+$186.

b) 1-(t-Butyloxycarbonylamino)-5-methoxy- 2-(methoxymethyl)-4-thiopyridone

A solution of the product from Preparation 38(a) (500 mg, 0.27 mmol) and t-butylcarbazate (350 mg, 0.27 mmol) in ethanol (10 ml) was heated at reflux for 18h. The solvent was evaporated under reduced pressure and the residue chromatographed on silica gel 60 eluting with 5% ethanol in dichloromethane to give the title compound (400 mg, 50%) as a brown foam; $v_{max}$ (CH$_2$Cl$_2$) 3350, 3050, 2970, 1745, and 1605 cm$^{-1}$; $\delta_H$ (CDCl$_3$) 1.45 (9H, s), 3.35 (3H, s), 3.75 (3H, s), 4.25 (2H, s), 6.8 (1H, s), 7.4 (1H, s); M$^+$ 300.

PREPARATION 39

1-(t-Butyloxycarbonylamino)-3-methoxy-2-methyl-4-thiopyridone a) 3-Methoxy-2-methyl-4-pyranone Dimethylsulphate (3.8 ml, 5.05 g, 0.04 mmol) was added to a solution of maltol (5.0 g, 0.04 mmol) in 10% aqueous potassium hydroxide (22.5 ml). After stirring for 5h the reaction mixture was extracted into CH$_2$Cl$_2$ (x3). The organic extract was dried (MgSO$_4$) and concentrated under reduced pressure. The residue was chromatographed on silica gel 60 eluting with 60% ethyl acetate in hexane to give the title compound (2.06 g, 37%) as a pale yellow oil; $v_{max}$ (film) 3080, 1620, and 1580 cm$^{-1}$; $\delta_H$ (CDCl$_3$) 2.3 (3H, s), 3.8 (3H, s), 6.3 (1H, d, J 6 Hz), 7.6 (1H, d, J 6 Hz).

b) 3-Methoxy-2-methyl-4-thiopyranone

The product from Preparation 39(a) (2.05 g, 14.6 mmol) in toluene (30 ml) was heated at 80° C. with Lawessons reagent (3.25 g, 8.0 mmol) for 1.5h. After cooling the reaction mixture was chromatographed on silica gel 60 eluting with toluene/ether mixtures to give the title compound (2.07 g, 91%) as a brown foam; $v_{max}$ (CH$_2$Cl$_2$) 3030, 1750, 1620, and 1550 cm$^{-1}$; $\delta_H$ (CDCl$_3$) 2.3 (3H, s), 3.8 (3H, s), 7.1 (1H, d, J 5 Hz), 7.35 (1H, d, J 5 Hz); M$^+$ 156.

c) 1-(t-Butyloxycarbonylamino)-3-methoxy-2-methyl-4-thiopyridone

A solution of the product from Preparation 39(b) (2.03 g, 13 mmol) and t-butylcarbazate (1.72 g, 13 mmol) in ethanol (30 ml) was heated at reflux for 64h. Further t-butylcarbazate was then added to the reaction mixture and reflux continued for a further 36h before allowing the reaction to stand at room temperature for 40h. The solvent was evaporated under reduced pressure and the residue chromatographed on silica gel 60 eluting with dichloromethane/ethanol mixtures to give the title compound (2.65 g) as a yellow foam; $v_{max}$ (CH$_2$Cl$_2$) 1740, and 1605 cm$^{-1}$.

PREPARATION 40

1-[N-(t-Butyloxycarbonyl)-N-(2-methoxyethyl)amino]-4-thiopyridone 1-(t-Butyloxycarbonylamino)-4-thiopyridone (0.24 g, 1.06 mmol) in N,N-dimethylformamide (5 ml) was treated with potassium carbonate (0.15 g, 1.0 mmol) and bromoethyl methyl ether (0.2 ml, 2.1 mmol). The mixture was stirred for 2h, then evaporated under reduced pressure. Purification on silica gel 60 eluting with ethanol, dichloromethane mixtures gave the title compound (0.028 g, 9%); $\delta_H$ (CDCl$_3$) 1.45 (9H, s), 3.35 (3H, s), 3.52 (2H, t, J 5 Hz), 3.87 (2H, t, J 5 Hz), 7.17 (2H, d, J 7 Hz), and 7.40 (2H, d, J 7 Hz).

PREPARATION 41

1-(1,2,4-Triazol-4-yl)-4-thiopyridone 1-(1,2,4-Triazol-4-yl)-4-pyridone (A. Sultan Afridi, A. R. Katritsky, and C. A. Ramsden, *J. Chem. Soc., Perkin Trans.*1, 1977, 1429) (0.12 g, 0.74 mmol) in toluene (4 ml) was treated with Lawesson's reagent (0.27 g, 0.67 mmol) and heated at 80° C. for 5h. The solvent was then evaporated under reduced pressure and the residue diluted with 1,2-dimethoxyethane. After being stirred at room temperature for 2h an orange precipitate had formed in the reaction mixture. This was removed by filtration and dried to give the title compound (0.052 g, 39%); $\delta_H$ (CF$_3$CO$_2$D) 8.17 (2H, d, J 6.5 Hz), 8.87 (2H, d, J 6.5 Hz), and 9.71 (2H, s); M$^+$ 178.

PREPARATION 42

1-[(6-Chloropyridin-2-yl)amino]-4-thiopyridone

6-Chloro-2-hydrazinopyridine (0.143 g, 1.0 mmol) and 4-thiopyranone (0.112 g, 1.0 mmol) were heated together at reflux in ethanol (15 ml). After 18h the solution was allowed to cool and evaporated to dryness under reduced pressure. Purification of the residue on silica gel 60 eluting with ethanol, dichloromethane mixtures gave the title compound (0.031 g, 13%); $\delta_H$ (CDCl$_3$+CD$_3$OD) 6.48 (1H, d, J 8 Hz), 6.97 (1H, d, J 8 Hz), 7.44 (2H, d, J 7 Hz), 7.53 (2H, d, J 7 Hz), and 7.60 (1H, t, J 8 Hz); M$^+$ 237.

PREPARATION 43

1-(Pyrazineamino)-4-thiopyridone a) Hydrazinopyrazine

A mixture of chloropyrazine (1.0 g, 11.56 mmol) and hydrazinehydrate (3.0 g, 93.7 mmol) was refluxed for 1h to obtain a bright yellow solution. The solution was then cooled and maintained at 4° C. for 18h. The precipitate was filtered, washed with hexane (20 ml) and dried in vacuo to give the title compound (0.24 g, 16%); $\delta_H$ (CDCl$_3$) 3.85 (2H,s), 6.01 (1H, s), 7.91–7.93 (1H, m), 8.02–8.04 (1H, m), and 8.21 (1H, s); M$^+$ 110.

b) 1-(Pyrazineamino)-4-thiopyridone

Hydrazino pyrazine (0.24 g, 2.26 mmol) in ethanol (10 ml) was treated with 4-thiopyranone (0.2 g, 1.78 mmol). The mixture was refluxed for 6h, cooled and evaporated under reduced pressure. Purification on silica gel 60 eluting with dichloromethane ethanol (9:1) gave the title compound (0.024 g, 5%); M$^+$ 204.

PREPARATION 44

1-[N-(t-Butyloxycarbonyl)-N-(2-methyl-4-thiazolyl)-methylamino]-4-thiopyridone a) 1-[N-(t-Butyloxycarbonyl)-N-(2-methyl-4-thiazolyl)-methylamino]-4-pyridone 1-(t-Butyloxycarbonylamino)-4-pyridone (0.1 g, 0.47 mmol) in N,N-dimethylformamide (2 ml) was treated successively with 4-(chloromethyl)-2-methylthiazole hydrochloride (0.07 g, 0.47 mmol) and potassium carbonate (0.131 g, 0.95 mmol). The mixture was stirred at room temperature for 18h, followed by evaporation to dryness under reduced pressure. Purification on silica gel 60 eluting with dichloromethane and ethanol (9:1) gave the title compound (0.064 g, 42%); $\delta_H$ (CDCl$_3$) 1.45 (9H, s), 2.71 (3H, s), 4.86 (2H, s), 6.26 (2H, d, J 8 Hz), 7.00 (1H, s), and 7.20 (2H, d, J8 Hz); MH$^+$ 322.

b) 1-[N-(t-butyloxycarbonyl)-N-(2-methyl-4-thiazolyl)methylamino]-4-thiopyridone The product of Preparation 44(a) (0.064 g, 0.2 mmol) in toluene (5 ml) was treated with Lawesson's reagent and the mixture was stirred at 80° C. for 40 minutes. The mixture was then cooled and purified on silica gel 60 eluting with dichloromethane and ethanol (9:1) to give the title compound (0.041 g, 61%); M$^+$337.

PREPARATION 45

1-(2-Imidazolin-2-yl)amino]-4-thiopyridone

2-Hydrazino-2-imidazoline hydrobromide (0.181 g, 1.0 mmol) in ethanol (10 ml) was treated with triethylamine (0.1 g, 1.0 mmol) and 4-thiopyranone (0.112 g, 1.0 mmol). The reaction mixture was heated at reflux for 7h and stirred at room temperature for 18h. The mixture was then evaporated to dryness under reduced pressure. Purification on silica gel 60 eluting with dichloromethane and ethanol mixtures gave the title compound (0.03 g, 15%); $\delta_H$ [(CD$_3$)$_2$CO], 3.59 (4H, s), 6.02 (1H, br s), 6.33 (1H, br s), 7.17 (2H, d, J 7 Hz), and 7.26 (2H, d, J 7 Hz); M$^+$ 194.

PREPARATION 46

1-(Phthalazin-1-ylamino)-4-thiopyridone

Hydralazine hydrochloride (0.196 g, 1.0 mmol) in ethanol (10 ml) was treated with triethylamine (0.1 ml, 1.0 mmol) and 4-thiopyranone (0.112 g, 1.0 mmol). The reaction mixture was refluxed for 5h, followed by stirring at room temperature for a further 72h. The mixture was evaporated to dryness under reduced pressure. Purification on silica gel 60 eluting with dichloromethane and ethanol mixtures gave the title compound (0.055 g, 22%); $\delta_H$ 7.32 (2H, d, J 7 Hz), 7.64 (2H, d, J 7 Hz), 7.77–7.90 (3H, m), 8.25 (1H, s), and 8.42 (1H, d, J 8 Hz); M$^+$ 254.

PREPARATION 47

1-[N-(t-Butyloxycarbonyl)-N-(cyanomethyl)amino]-4-thiopyridone a) 1-[N-(t-Butyloxycarbonyl)-N-(cyanomethyl)amino]-4-pyridone a) 1-(t-Butyloxycarbonylamino)-4-pyridone (0.1 g, 0.47 mmol) in N,N-dimethylformamide (2 ml) was treated successively with potassium carbonate (0.064 g, 0.47 mmol) and bromoacetonitrile (0.056 g, 0.47 mmol). The reaction mixture was stirred at room temperature for 2h, filtered and evaporated under reduced pressure. Purification on silica gel 60 eluting with ethanol, dichloromethane (1:9) gave the title compound (0.106 g, 90%); $\delta_H$ (CDCl$_3$) 1.49 (9H, s), 4.59 (2H, s), 6.37 (2H, d, J 8 Hz), and 7.32 (2H, d, J 8 Hz); M$^+$ 249.

b) 1-[N-(t-Butyloxycarbonyl)-N-(cyanomethyl)amino]-4-thiopyridone

The product of Preparation 47(a) (0.1 g, 0.4 mmol) in toluene (10 ml) was treated with Lawesson's reagent (0.15 g, 0.37 mmol) and treated at 80° C. for 40 minutes. The mixture was allowed to cool and was purified on silica gel 60 eluting with ethanol dichloromethane mixtures to give the title compound (0.053 g, 50%); $\delta_H$ (CDCl$_3$) 1.50 (9H, s), 4.6 (2H, s), 7.1 (2H, d, J 7.5 Hz), and 7.30 (2H, d, J 7.5 Hz); M$^+$ 265.

PREPARATION 48 a) 1-[N-(t-Butyloxycarbonyl)-N-(prop-2-yn-1-yl)-amino-4-pyridone 1-(t-Butyloxycarbonylamino)-4-pyridone (0.1 g, 0.47 mmol) in N,N-dimethylformamide (2 ml) was treated successively with potassium carbonate (0.064 g, 0.47 mmol) and propargyl bromide (0.056 g, 0.47 mmol). The reaction mixture was stirred at room temperature for 2h and evaporated under reduced pressure. Purification on silica gel 60 eluting with dichloromethane gave the title compound (0.093 g, 79%); $\delta_H$ (CDCl$_3$) 1.47 (9H, s), 2.43 (1H, t, J 2 Hz), 4.45 (2H, d, J 2 Hz), 6.35 (2H, d, J 8 Hz), and 7.35 (2H, d, J 8 Hz); M$^+$ 248.

b) 1-[N-(t-Butyloxycarbonyl)-N-(prop-2-yn-1-yl)-amino]-4-thiopyridone

The product of Preparation 48(a) (0.082 g, 0.33 mol) in toluene (10 ml) was treated with Lawesson's reagent (0.133 g, 0.33 mmol) and heated at 80° C. for 0.5h. The mixture was allowed to cool and chromatographed on silica gel 60 eluting with dichloromethane to give the title compound (0.048 g, 55%); $\delta_H$ (CDCl$_3$), 1.48 (9H, s), 2.46 (1H, t, J 2.4 Hz), 4.47 (2H, d, J 2.4 Hz), 7.15 (2H, d, J 7.5 Hz), and 7.39 (2H, d, J 7.5 Hz ); M$^{H+}$ 265.

PREPARATION 49

1-(t-Butyloxycarbonylamino)-2,6-dimethyl-4-thiopyridone a) 2,6-Dimethyl-4-thiopyranone 2,6-Dimethyl-4-pyranone (0.25 g, 2.0 mmol) in toluene (10 ml) was treated with Lawesson's reagent (0.22 g, 1.1 mmol) and heated at 100° C. for 3h. A further quantity of Lawesson's reagent (0.22 g, 1.1 mmol) was added and the mixture heated at 100° C. for 0.75h. The mixture was allowed to cool, then purified on silica gel 60 eluting with ethanol and dichloromethane (1:9) to give the title compound (0.28 g, 98%).

b) 1-(t-Butyloxycarbonylamino)-2,6-dimethyl- 4-thiopyridone 2,6-Dimethyl-4-thiopyranone (0.14 g, 1.0 mmol) and t-butylcarbazate (0.26 g, 2.0 mmol) were heated together at reflux in ethanol for 48h. A little acetone was added to the mixture which was then evaporated to dryness under reduced pressure. Purification of the residue on silica gel 60 eluting with ethanol and dichloromethane (1:50) gave the title compound (0.089 g, 35%); $v_{max}$ (CH$_2$Cl$_2$) 1735 and 1615 cm$^{-1}$; $\delta_H$ (CDCl$_3$) 1.50 (9H, s), 2.24 (6H, s), and 7.01 (2H, s); M$^+$ 254.

EXAMPLE 1

[6R, 7R ]-7-[2-(2-Amino-4-thiazolyl )- 2-(Z)-(methoxyimino)acetamido]-3-[1-(dimethylamino)pyridinium- 4-thiomethyl]-ceph-3-em-4-carboxylate.

a) 4-Methoxybenzyl [6R, 7R ]-3-[1-(dimethylamino)pyridinium- 4-thiomethyl]-7-[2-(Z)-(methoxyimino)-2-( 2-tritylamino-4-thiazolyl)acetamido]ceph-3-em-4-carboxylate iodide.

4-Methoxybenzyl [6R,7R]-3-(iodomethyl)-7-[ 2-(Z)-(methoxyimino)-2-(2-tritylamino-4-thiazolyl)acetamido]-ceph- 3-em-4-carboxylate (0.13 g, 0.15 mmol) in dichloromethane (5 ml) was treated with 1-(dimethylamino)-4-thiopyridone (30 mg, 0.19 mmol) in dichloromethane (2 ml). After 30 mins the solvent was removed by evaporation and the product purified by chromatography on silica gel eluting with mixtures of dichloromethane and ethanol giving the title compound in 75% yield: $v_{max.}$ (dichloromethane) 1780, 1720, 1680, 1605, 1505 cm$^{-1}$; m/z (FAB thioglycerol) M+912.

b) [6R, 7R ]-7-[2-(2-Amino-4-thiazolyl)- 2-(Z)-(methoxyimino)acetamido]-3-[1-(dimethylamino)pyridinium- 4-thiomethyl]ceph-3-em-4-carboxylate.

4-Methoxybenzyl [6R,7R]-3-[1-(dimethylamino)pyridinium 4-thiomethyl]-7-[2-(Z)-(methoxyimino)-2-(2-tritylamino- 4-thiazolyl)-acetamido]ceph-3-em-4-carboxylate iodide (100 mg, 0.10 mmol) in dichloromethane (5 ml) was treated with trifluoroacetic acid (0.53 ml) for 30 mins and then diluted with toluene. The solvent was evaporated and the residue taken up in water with sodium bicarbonate to pH 7. Purification on HP20SS followed by lyophilisation gave the desired compound in (34 mg: 57%): $v_{max.}$ (KBr) 1760, 1670, 1610 cm$^{-1}$; $\delta$[D$_2$O] 2.97 (6H, s), 3.41 and 3.70 (2H, ABq, J 17.6 Hz), 3.92 (3H, s), 4.10 and 4.39 (2H, ABq, J 13.7 Hz), 5.13 (1H, d, J 4.6 Hz), 5.72 (1H, d, J 4.6 Hz), 6.95 (1H, s), 7.80 and 8.65 (4H, ABq, J 7.2 Hz]; m/z (FAB Thioglycerol/Thiodiethylene glycol) MH$^+$ 550.

EXAMPLE 2

[6R, 7R ]-7-[2-(2-Amino-4-thiazolyl)- 2-(Z)-(methoxyimino)acetamido]-3-[1-(methylamino) pyridinium-4-thiomethyl]ceph-3-em-4-carboxylate (i)

a) 4-Methoxybenzyl [6R,7R]-3-[ 1-(N-t-butyoxycarbonyl-N-methylamino)pyridinium- 4-thiomethyl]-7-[2-(Z)-(methoxyimino)- 2-(2-tritylamino-4-thiazolyl)acetamido]-ceph- 3-em-4-carboxylate iodide 4-Methoxybenzyl [6R, 7R]-3-[chloromethyl]-7-[ 2-(Z)-(methoxyimino)-2-(2-tritylamino-4-thiazolyl)acetamido]-ceph- 3-em-4-carboxylate (0.16 g 0.2 mmol) in dichloromethane (10 ml) was treated with 1-[(N-t-butyloxycarbonyl)-N-methylamino]- 4-thiopyridone (0.05 g 0.2 mmol) for 24 hours and then treated with sodium iodide (0.075 g 0.5 mmol) in acetone (minimum volume). After a further 1 hour the product was purified by chromatography on silica gel eluting with mixtures of ethanol and dichloromethane giving the title compound (0.18 g 0.16 mmol) in 78% yield.

b) [6R,7R]-7-[2-(2-Amino-4-thiazolyl)- 2-(Z)-(methoxyimino)acetamido]-3-[1-(methylamino)pyridinium- 4-thiomethyl]ceph-3-em-4-carboxylate 4-Methoxybenzyl [6R,7R]-3-[1-[(N-t-butyloxycarbonyl)-N-methylamino]pyridinium- 4-thiomethyl]-7-[2-(Z)-(methoxyimino)- 2-(2-tritylamino-4-thiazolyl)-acetamido] ceph-3-em-4-carboxylate iodide (0.10 g 0.088 mmol) was treated with trifluoroacetic acid (1 ml) for 10 minutes. The mixture was evaporated to dryness and the residue was triturated with ether (3×30 ml). The product was dissolved in water with sodium bicarbonate to pH 7.0. The product was purified by chromatography on Diaion HP20SS eluting with mixtures of tetrahydrofuran and water. Fractions containing product were combined and freeze-dried to give the title compound (0.024 g 0.045 mmol) in 50% yield; $v_{max}$ (KBr) 1763, 1665, 1616, and 1532 cm$^{-1}$; $\delta$(D$_2$O) 3.01 (3H, s), 3.43 and 3.71 (2H, ABq, J 18 Hz), 3.95 (3H, s), 4.11 and 4.40 (2H, ABq, J 14 Hz), 5.14 (1H, d, J 4.5 Hz), 5.74 (1H, d, J 4.5 Hz), 6.96 (1H, s), 7.78 and 8.50 (4H, ABq, J 7.5 Hz); m/z (FAB thioglycerol) MH+ 536.

ii)

(a) 4-Methoxybenzyl [6R,7R]-7-[ 2-(Z)-(methoxyimino)-2-(2-tritylamino-4-thiazolyl)acetamido]- 3-[1-(methylamino)pyridinium-4-thiomethyl]ceph-3-em- 4-carboxylate iodide 4-Methoxybenzyl [6R, 7R]-3-[chloromethyl]-7-[ 2-(Z)-(methoxyimino)-2-(2-tritylamino-4-thiazolyl)acetamido]-ceph- 3-em-4-carboxylate (0.795 g 1 mmol) in dichloromethane (20 ml) was treated with 1-(methylamino)-4-thiopyridone (0.14 g 1 mmol) and then sodium iodide (0.3 g 2 mmol) in acetone (minimum volume). The reaction was complete after 5 hours. The product was purified by chromatography on silica gel eluting with mixtures of dichloromethane and methanol to give the title compound (0.52 g 0.46 mmol) in 46% yield. $\delta$(CDCl$_3$) 3.0 (3H, s), 3.5–3.7 (2H, m), 3.73 (3H, s), 3.98 (3H, s), 4.2–4.5 (2H, m), 5.02 (1H, d, J 5 Hz), 5.17 (2H, s), 5.82 (1H, dd, J 5 and 9 Hz), 6.52 (1H, s), 6.8 (2H, ABq, J 8 Hz), 7.2–7.6 (18H, m), and 7.7 and 8.74 (4H, ABq, J 7 Hz).

(b) [6R,7R]-7-[2-(2-Amino-4-thiazolyl)- 2-(Z)-(methoxyimino)acetamido]-3-[1-(methylamino)pyridinium- 4-thiomethyl]ceph-3-em-4-carboxylate 4-Methoxybenzyl [6R, 7R]-7-[2-(Z)-(methoxyimino)-2-( 2-tritylamino-4-thiazolyl)acetamido]-3-[1-(methylamino) pyridinium-4-thiomethyl]ceph-3-em-4-carboxylate iodide (0.5 g 0.44 mmol) in dichloromethane (20 ml) was treated with trifluoroacetic acid (1.5 ml). The mixture was evaporated to dryness and the residue triturated with ether (3×30 ml). The product was dissolved in water with sodium bicarbonate to pH 7. The product was purified by chromatography on Diaion HP20SS eluting with mixtures of tetrahydrofuran and water. Fractions containing product were combined and freeze-dried to give the title compound (92 mg 0.17 mmol) in 39% yield. The material was identical to that prepared in Example 2(i) above.

EXAMPLE 3

Sodium [6R,7R]-7-[2-(2-amino- 4-thiazolyl)-2-(Z)-(1-carboxy-1-methylethoxyimino)acetamido]- 3-[1-(methylamino)pyridinium-4-thiomethyl]ceph- 3-em-4-carboxylate a) 4-Methoxybenzyl [6R,7R]-7-[2-(Z)-( 1-t-butyloxycarbonyl-1-methylethoxyimino)-2-(2-tritylamino- 4-thiazolyl)acetamido]-3-[1-(methylamino)pyridinium- 4-thiomethyl] ceph-3-em-4-carboxylate iodide 4-Methoxybenzyl [6R, 7R]-7-[2-(Z)-(1-t-butyloxycarbonyl- 1-methylethoxyimino)-2-(2-tritylamino-4-thiazolyl)acetamido]-3-chloromethylceph-3-em- 4-carboxylate (0.092 g 0.1 mmol) in dichloromethane (4 ml) was treated with 1-(methylamino)-4-thiopyridone (0.014 g 0.1 mmol) and sodium iodide (20 mg) in acetone (min.vol.) for 5h. The mixture was washed with water and evaporated to dryness to give the title compound (120 mg) which was used without further purification.

b) Sodium [6R,7R]-7-[2-(2-amino-4-thiazolyl)- 2-(Z)-(1-carboxy-1-methylethoxyimino)acetamido]-3-[ 1-(methylamino)pyridinium-4-thiomethyl]ceph-3-em-4-carboxylate 4-Methoxybenzyl [6R, 7R]-7-[2-(Z)-(1-t-butyloxy carbonyl-1-methylethoxyimino)-2-(2-tritylamino- 4-thiazolyl)acetamido]-3-[1-(methylamino)pyridinium- 4-thiomethyl] ceph-3-em-4-carboxylate iodide (0.12 g) was treated with trifluoroacetic acid (1 ml) for 2 hours, a further 2 ml were added and the mixture stirred for 30 minutes more. The mixture was evaporated to dryness and triturated with ether (2×20 ml). The solid product was dissolved in water with sodium bicarbonate to pH 7, filtered and purified by chromatography on Diaion HP20SS eluting with mixtures of tetrahydrofuran and water. The title compound (0.013 g) was obtained in 21% yield overall; $v_{max}$ (KBr) 1763, 1660, 1600, and 1530 cm$^{-1}$; δ(D$_2$O) 1.44 (3H, s), 1.46 (3H, s) 3.00 (3H, s), 3.45 and 3.69 (2H, ABq, J 17.5 Hz), 4.15 and 4.38 (2H, ABq, J 14 Hz), 5.16 (1H, d, J 4.5 Hz), 5.75 (1H, d, J 4.5 Hz), 6.94 (1H, s), 7.81 (2H, d, J 7 Hz), and 8.50 (2H, d, J 7 Hz); m/z (FAB thioglycerol) MH+ 630.

EXAMPLE 4

[6R,7R]-3-(1-Aminopyridinium-4-thiomethyl)-7-[ 2-(2-amino-4-thiazolyl)-2-(Z)-(methoxyimino)acetamido]ceph-3-em-4-carboxylate a) 4-Methoxybenzyl [6R,7R]-3-[1-(t-butyloxycarbonylamino)pyridinium- 4-thiomethyl]-7-[2-(Z)-(methoxyimino)- 2-(2-tritylamino-4-thiazolyl)acetamido]ceph-3-em- 4-carboxylate chloride 4-Methoxybenzyl [6R,7R]-3-(chloromethyl)-7-[ 2-(Z)-(methoxyimino)-2-(2-tritylamino-4-thiazolyl)acetamido] ceph- 3-em-4-carboxylate (0.10 g, 0.12 mmol) in dichloromethane (5 ml) was treated with 1-(t-butyloxycarbonylamino)- 4-thiopyridone (0.058 g, 0.26 mmole) in dichloromethane (3 ml). The reaction mixture was stirred for 3h, evaporated under reduced pressure and chromatographed on silica gel 60 eluting with ethanol, dichloromethane mixtures to give the title compound (0.091 g, 68%); $v_{max}$ (KBr) 1785, 1719, 1675, and 1612 cm$^{-1}$; δ$_H$ (CDCl$_3$) 1.54 (9H, s), 3.48 and 3.60 (2H, ABq, J 18 Hz), 3.82 (3H, s), 4.07 (3H, s), 4.12 and 4.39 (2H, ABq, J 13 Hz), 5.05 (1H, d, J 5 Hz), 5.21 and 5.27 (2H, ABq, J 12 Hz), 5.93 (1H, dd, J 5 Hz), 6.72 (1H, s), 6.83 (1H, d, J 9 Hz), 6.89 (2H, d, J 8.5 Hz), 7.02 (1H, br s), 7.30 (17H, m), 7.42 (2H, d, J 7 Hz), and 8.54 (2H, d, J 7 Hz); m/z (F.A.B., 3-nitrobenzyl alcohol, sodium acetate) M Na$^+$ 1006.

b) [6R,7R]-3-(1-Aminopyridinium-4-thiomethyl)-7-[ 2-(2-amino-4-thiazolyl)-2-(Z)-(methoxyimino)acetamido]-ceph- 3-em-4-carboxylate The product of Example 4 (a) (0.091 g, 0.09 mmol) was treated with trifluoroacetic acid (1 ml) and stirred for 10 mins. The mixture was diluted with toluene and evaporated to dryness. Purification on Diaion HP20SS resin gave the title compound (0.017 g, 37%); $v_{max}$ (KBr) 1763, 1670, and 1611 cm$^{-1}$; δ$_H$ (D$_2$O ) 3.43 and 3.72 (2H, ABq, J 17.5 Hz), 3.94 (3H, s), 4.13 and 4.41 (2H, ABq, J 14 Hz), 5.15 (1H, d, J 4.5 Hz), 5.73 (1H, d, J 4.5 Hz), 6.96 (1H, s), 7.73 (2H, d, J 7 Hz), and 8.38 (2H, d, J 7 Hz); m/z (F.A.B., thioglycerol) MH$^+$ 522.

EXAMPLE 5

[6R,7R]-7-[2-(2-Amino-4-thiazolyl)- 2-(Z)-(methoxyimino)acetamido]-3-[1-(carboxymethylamino)pyridinium-4-thiomethyl]ceph-3-em-4-carboxylate a) 4-Methoxybenzyl [6R,7R]-3-[1-[ N-(t-butyloxycarbonyl)-N-carbonyl)-N-(t-butyloxycarbonylmethyl)amino]pyridinium- 4-thiomethyl]-7-[2-(Z)-(methoxyimino)-2-( 2-tritylamino-4-thiazolyl)acetamido]ceph-3-em-4-carboxylate iodide 4-Methoxybenzyl [6R,7R]-3-(chloromethyl)-7-[ 2-(Z)-(methoxyimino)-2-(2-tritylamino-4-thiazolyl)acetamido]-ceph- 3-em-4-carboxylate (0.10 g, 0.12 mmol) in acetonitrile (5 ml) was treated with 1-[N-(t-butyloxycarbonyl)-N-(t-butyloxycarbonylmethyl)amino]- 4-thiopyridone (0.60 g, 0.18 mmol) in acetonitrile (2 ml). The reaction mixture was stirred for 2h, sodium iodide (0.15 g, 0.10 mmol) was added and the mixture stirred for a further 1h. After evaporation of the solvent under reduced pressure the mixture was chromatographed on silica gel 60 eluting with 5% ethanol in dichloromethane to give the title compound (0.096 g, 73%); $v_{max}$ (KBr) 1785, 1735, 1681, and 1615 cm$^{-1}$; δ$_H$ (CDCl$_3$) 1.52 (18H, m), 3.56 and 3.79 (2H, ABq, J 19 Hz), 3.81(3H, s), 4.06 (3H, s), 4.25–4.60 (2H, m), 4.77 (2H, s), 5.09 (1H, d, J 5 Hz), 5.23 (2H, s), 5.92 (1H, d, J 5 Hz), 6.72 (1H, s), 6.89 (2H, d, J 9 Hz), 7.31 (19H, m), 7.87 (2H, m), 8.78 (2H, d, J 7 Hz); m/z (F.A.B., thioglycerol) M$^+$ 1098.

b) [6R,7R]-7-[2-(2-Amino-4-thiazolyl)- 2-(Z)-(methoxyimino)acetamido]-3-[1-(carboxymethylamino)pyridinium-4-thiomethyl]ceph-3-em-4-carboxylate The product of Example 5(a) (0.09 g, 0.08 mmol) was treated with trifluoroacetic acid (1 ml) and stirred for 0.5h. The mixture was evaporated under reduced pressure, diluted with toluene and evaporated to dryness. Purification on Diaion HP20SS resin eluting with water, acetone mixtures gave the title compound (0.014 g, 32%); $v_{max}$ (KBr) 1769, 1669, and 1618 cm$^{-1}$; δ$_H$ (D$_2$O) 3.44 and 3.72 (2H, ABq, J 17.5 Hz), 3.99 (3H, s), 4.02 (2H, s), 4.12 and 4.40 (2H, ABq, J 13.5 Hz), 5.16 (1H, d, J 5 Hz), 5.76 (1H, d, J 5 Hz), 7.04 (1H, s), 7.77 (2H, d, J 7 Hz), and 8.57 (2H, d, J 7 Hz); m/z (F.A.B., thioglycerol) MH$^+$ 580.

EXAMPLE 6

[6R,7R]-7-[2-(2-Amino-4-thiazolyl)-2-(Z)-(methoxyimino) acetamido]-3-[1-(ethylamino)pyridinium-4-thiomethyl]-ceph- 3-em-4-carboxylate a) 4-Methoxybenzyl [6R,7R]-3-[1-[(N-t-butyloxycarbonyl)-N-ethylamino] pyridinium-4-thiomethyl]-7-[2-(Z)-

(methoxyimino)- 2-(2-tritylamino-4-thiazolyl)acetamido] ceph- 3-em-4-carboxylate iodide 4-Methoxybenzyl [6R,7R]-3-(chloromethyl)-7-[2-(Z)-(methoxyimino)- 2-(2-tritylamino-4-thiazolyl) acetamido] ceph-3-em-4-carboxylate (0.10 g, 0.12 mmol) in acetonitrile (5 ml) was treated with sodium iodide (0.02 g, 0.13 mmol) followed by 1-[(N-t-butyloxycarbonyl)-N-ethylamino]-4-thiopyridone (0.06 g, 0.24 mmol). The reaction mixture was stirred for 0.5h, then evaporated to dryness under reduced pressure. The residue was chromatographed on silica gel 60 eluting with 5% ethanol in dichloromethane to give the title compound (0.119 g, 86%); $v_{max}$ (KBr) 1784, 1726, 1678, and 1613 cm$^{-1}$; $\delta_H$ (CDCl$_3$ +CD$_3$OD) 1.27 (3H, t, J 7 Hz), 1.52 (9H, s), 3.58 and 3.85 (2H, ABq, J 18.5 Hz), 3.81 (3H, s), 4.07 (5H, m), 4.50 and 4.60 (2H, ABq, J 12 Hz), 5.09 (1H, d, J 5 Hz), 5.20 and 5.26 (2H, ABq, J 12 Hz), 5.90 (1H, d, J 5 Hz), 6.73 (1H, s), 6.88 (2H, d, J 8.5 Hz), 7.31 (17H, m), 8.06 (2H, d, J 7 Hz), and 8.48 (2H, d, J 7 Hz); m/z (F.A.B., thioglycerol) M$^+$ 1012.

b) [6R,7R]-7-[2-(2-Amino-4-thiazolyl)- 2-(Z)-(methoxyimino)acetamido]-3-[1-(ethylamino)pyridinium- 4-thiomethyl]ceph-3-em-4-carboxylate The product of Example 6(a) (0.11 g, 0.1 mmol) was treated with trifluoroacetic acid (1 ml) and stirred for 7 mins. The reaction mixture was evaporated under reduced pressure, diluted with toluene and evaporated. Purification on Diaion HP20SS eluting with water, acetone mixtures gave the title compound (0.033 g, 60%); $v_{max}$ (KBr) 1766, 1670, and 1618 cm$^{-1}$; $\delta_H$ (D$_2$O) 1.13 (3H, t, J 7 Hz), 3.33 (2H, q, J 7 Hz), 3.45 and 3.73 (2H, ABq, J 17.5 Hz), 3.99 (3H, s), 4.16 and 4.44 (2H, ABq, J 13.5 Hz), 5.16 (1H, d, J 4.5 Hz), 5.77 (1H, d, J 4.5 Hz), 6.98 (1H, s), 7.84 (2H, d, J 7 Hz), and 8.53 (2H, d, J 7 Hz); m/z (F.A.B., thioglycerol) MH$^+$ 550.

EXAMPLE 7

[6R,7R]-7-[2-(2-Amino-4-thiazolyl)- 2-(Z)-(methoxyimino)acetamido]-3-[1-[4-(2-hydroxyethyl)piperazin-1-yl]pyridinium- 4-thiomethyl]ceph-3-em-4-carboxylate a) 4-Methoxybenzyl [6R,7R]-3-[1-[4-(2-hydroxyethyl)piperazin- 1-yl]pyridinium-4-thiomethyl]-7-[ 2-(Z)-(methoxyimino)-2-(2-tritylamino-4-thiazolyl)acetamido] ceph- 3-em-4-carboxylate iodide 4-Methoxybenzyl [6R,7R]-3-(chloromethyl)-7-[ 2-(Z)-(methoxyimino)-2-(2-tritylamino-4-thiazolyl)acetamido] ceph- 3-em-4-carboxylate (0.245 g, 0.31 mmole) in acetonitrile (6 ml) was treated with 1-[4-(2-hydroxyethyl)piperazin- 1-yl)-4-thiopyridone (0.074, 0.3 mmole). The reaction mixture was stirred for 0.5h, sodium iodide (0.046, 0.3 mmole) was added and the reaction mixture was stirred for a further 1.25h. After evaporation of the solvent under reduced pressure the mixture was chromatographed on silica gel 60 eluting with 20% ethanol in dichloromethane to give the title compound; $v_{max}$ (CHCl$_3$) 1785, 1720, 1680, and 1610 cm$^{-1}$; $\delta_H$ (CD$_3$OD) 2.84 (2H, m), 3.1 (4H, s), 3.5–3.8 (8H, m), 3.8 (3H, s), 4.04 (3H, s), 4.35 and 4.54 (2H, ABq, J 13 Hz), 5.1 (1H, d, J 5 Hz), 5.21 (2H, ABq, J 12 Hz), 5.9 (1H, d, J 5 Hz), 6.7 (1H, s), 6.88 and 7.32 (4H, 2d, J 9 Hz), 7.28 (15H, s), and 7.9 and 8.9 (4H, 2d, J 7 Hz); M$^+$ 997.

b) [6R,7R]-7-[2-(2-Amino-4-thiazolyl)- 2-(Z)-(methoxyimino)acetamido]-3-[1-[4-(2-hydroxyethyl)piperazin- 1-yl] pyridinium-4-thiomethyl]ceph-3-em-4-carboxylate The product of Example 7(a) (0.25 g, 0.25 mmol) in dichloromethane (11 ml) was treated with trifluoroacetic acid (1.17 ml) and stirred at room temperature for 0.5h. The mixture was evaporated under reduced pressure, diluted with toluene and evaporated to dryness. Water (5 ml) was added and the pH adjusted to 7 using aqueous sodium bicarbonate, purification carried out using Diaion HP20SS resin eluting with water, acetone mixtures gave the title compound (0.084 g, 53%); $v_{max}$ (KBr) 1764, 1669, 1611, and 1533 cm$^{-1}$; $\delta_H$ (D$_2$O) 2.68 (2H, m), 2.66 (4H, m), 3.31 (4H, m), 3.44 and 3.7 (2H, ABq, J 17.5 Hz), 3.71 (2H, m), 3.94 (3H, s), 4.13 and 4.4 (2H, ABq, J 14 Hz), 5.14 (1H, d, J 5 Hz), 5.73 (1H, d, J 5 Hz), 6.97 (1H, s), 7.83 and 8.69 (4H, 2d, J 7 Hz); m/z (F.A.B., thioglycerol) MH$^+$ 635.

EXAMPLE 8

[6R,7R]-7-[2-(2-Amino-4-thiazolyl)- 2-(Z)-(cyclopentyloxyimino)acetamido]-3-[1-(methylamino)pyridinium-4-thiomethyl]ceph-3-em-4-carboxylate.

a) 4-Methoxybenzyl [6R,7R]-7-[2-(2-amino-4-thiazolyl)-2-(Z)-(cyclopentyloximino)acetamido]-3-(chloromethyl)ceph- 3-em-4-carboxylate.

2-(2-Amino-4-thiazolyl)-2-(Z)-(cyclopentyloxyimino) acetic acid (2.57 g, 10 mmol) was dissolved in N,N dimethylformamide (20 ml) with N,N-diisopropylethylamine (1.74 ml, 10 mmol) and cooled to –30° C. The mixture was treated with methanesulphonyl chloride (0.78 ml, 10 mmol) and allowed to warm to 0° C. for 10 minutes and recooled to –30° C. 4-Methoxybenzyl [6R,7R]- 7-amino-3-(chloromethyl)ceph-3-em-4-carboxylate hydrochloride (4.05 g, 10 mmol) was dissolved in N,N dimethylformamide with N,N diisopropylethylamine (3.50 ml, 20 mmol) and added to the cooled solution of activated acid. The mixture was allowed to warm to room temperature and stirred for 2h. The mixture was partitioned between ethyl acetate (250 ml) and water. The aqueous layer was back extracted with a further portion of ethyl acetate and then these two organic phases were sequentially washed with water (200 ml×2), dilute citric acid (100 ml×2), water, dilute sodium hydrogen bicarbonate and brine. The organic phases where then combined, dried over MgSO$_4$ and evaporated to give the title compound (4.2 g 69%); $v_{max}$ (KBr) 1785, 1723, 1675, 1612 and 1513 cm$^{-1}$; $\delta_H$ (CDCl$_3$) 1.5–2.0 (8H,m), 3.50 and 3.70 (2H, ABq J 18 Hz), 3.82 (3H,s), 4.40 and 4.60 (2H, ABq, J 12 Hz), 4.98 (1H,m), 5.05 (1H,d, J 5 Hz) 5.23 and 5.27 (2H, ABq, J 12 Hz), 5.96 (1H,dd, J 9 and 5 Hz) 6.1–6.4 (2H,broad), 6.91 and 7.35 (4H, 2d, J 8 Hz), 7.07 (1H,s), and 7.39 (1H,d, J 9 Hz); m/z (FAB, thioglycerol) MH$^+$ 606.

b) 4-Methoxybenzyl [6R,7R]-7-[2-(2-amino-4-thiazoyl)-2-(cyclopentyloxyimino)acetamido]-3-[1-(methylamino)pyridinium- 4-thio methyl]ceph-3-em-4-carboxylate iodide 4-Methoxybenzyl [6R,7R]-7-[2-(2-amino-4-thiazolyl)-2-(Z)-(cyclopentyloxyimino)acetamido]-3-(chloromethyl)ceph- 3-em-4-carboxylate (0.15 g, 0.25 mmol) was dissolved in acetonitrile (5 ml) and treated with sodium iodide (0.045 g, 0.3 mmol) and then after 10 minutes with 1-(methylamino)-4-thiopyridone (0.04 g, 0.29 mmol). A gum precipitated gradually from the solution so a further volume of acetonitrile (5 ml) was added. After 70 minutes the mixture was evaporated to dryness and the product purified by chromatography on silica eluting with methanol, dichloromethane mixtures. Fractions containing product were combined and evaporated to give the title compound (0.13 g, 62%); $\delta_H$ (CDCl$_3$+CD$_3$OD) 1.5–2.0 (8H,m), 3.07 (3H,s), 3.83 (3H,s), 4.22 and 4.50 (2H, ABq, J 11 Hz), 4.8–4.9 (1H,m) 5.11 (1H, d, J 5 Hz), 5.20 and 5.30 (2H, ABq, J 12 Hz), 5.90 (1H,d,J 5 Hz), 6.82 (1H,s), 6.9 (2H,ABq, J 8 Hz), 7.75 and 8.65 (4H, 2d, J 7 Hz).

c) [6R,7R]-7-[2-(2-Amino-4-thiazolyl)- 2-(Z)-(cyclopentyloxyimino)acetamido]-3-[ 1-(methylamino)pyridinium-4-thiomethyl]ceph-3-em-4-carboxylate 4-Methoxybenzyl [6R,7R]-7-[2-(2-amino-4-thiazolyl)-2-(Z)-(cyclopentyloxyimino)acetamido]-3-[1-(methylamino)pyridinium- 4-thiomethyl]ceph-3-em-4-carboxylate iodide (0.13 g, 0.16 mmol) was dissolved in dichloromethane (10 ml) with trifluoroacetic acid (0.36 ml). The mixture was stirred until the reaction was complete at 50 minutes. The mixture was evaporated twice from dichloromethane and then the residue was titurated with ether. The product was dissolved in water at $pH_8$ and then purified by chromatography on HP20SS. Fractions containing product were combined, evaporated to low volume and freeze dried to give the title compound (0.011 g 12%); $v_{max}$ (KBr) 1762, 1670, 1617, and 1533 cm$^{-1}$; $\delta_H$ (D$_2$O) 1.5–2.1 (8H,m), 3.00 (3H,s), 3.45 and 3.70 (2H, ABq, J 18 Hz) 4.10 and 4.41 (2H, ABq, J 13 Hz), 4.7 (1H,m), 5.14 (1H,d, J 5 Hz), 5.72 (1H,d, J 5 Hz), 6.94 (1H,s), 7.79 (2H,d, J 7 Hz), and 8.50 (2H,d, J 7 Hz); m/z (F.A.B., thioglycerol/acetic acid) MH$^+$ 590.

EXAMPLE 9

[6R,7R]-7-[2-(2-Amino-4-thiazolyl)- 2-(Z)-(hydroxyimino)acetamido]-3-[1-(methylamino)pyridinium- 4-thiomethyl]ceph-3-em-4-carboxylate a) 4-Methoxybenzyl [6R,7R]-3-(chloromethyl)-7-[ 2-(2-tritylamino-4-thiazolyl)-2-(Z)-(trityloxyimino)acetamido] ceph- 3-em-4-carboxylate 2-(2-Tritylamino-4-thiazolyl)-2-(Z)-(trityloxyimino) acetic acid (0.067 g, 0.1 mmol) was dissolved in dichloromethane (6.7 ml) and treated with N,N diisopropylethylamine (0.017 ml), 0.1 mmol) and methane-sulphonyl chloride (0.008 ml, 0.1 mmol). After 10 minutes at room temperature infra red showed only partial activation so further amounts of N,N diisopropylethylamine (0.0174 ml) and methane-sulphonyl chloride (0.0077 ml) were added. After a further 10 minutes infra red showed reaction was complete. 4-Methoxybenzyl [6R,7R]-7-amino- 3-(chloromethyl)ceph-3-em-4-carboxylate hydrochloride (0.081 g, 0.2 mmol) was dissolved in dichloromethane (5 ml) containing N,N diisopropylethylamine (0.07 ml, 0.4 mmol), added to the activated acid solution and stirred for 1.5h. The solution was diluted with ethyl acetate and then washed with water, dilute citric acid, water, and brine. The solution was dried over MgSO$_4$ and evaporated. The product was purified by chromatography on silica gel eluting with hexane, ethyl acetate mixtures to give the title compound (0.055 g, 55%); $\delta_H$ (CDCl$_3$) 3.22 and 3.56 (2H,ABq, J 18 Hz), 3.78 (3H,s), 4.35 and 4.53 (2H,ABq, J 12 Hz), 5.00 (1H,d, J 5 Hz), 5.22 (2H,s), 6.00(1H,dd, J 9 and 5 Hz), 6.40 (1H,s), 6.87 (2H,d, J 8 Hz), and 7.0–7.6 (32H,m).

b) 4-Methoxybenzyl [6R,7R]-3-[1-(methylamino)pyridinium- 4-thiomethyl]-7-[2-(2-tritylamino-4-thiazolyl)-2-(Z)-(trityloxyimino)acetamido]ceph-3-em-4-carboxylate iodide 4-Methoxybenzyl [6R,7R]-3-(chloromethyl)-7-[2-( 2-tritylamino-4-thiazolyl)-2-(Z)-(trityloxyimino) acetamido] ceph-3-em-4-carboxylate (0.055 g, 0.054 mmol) was dissolved in acetonitrile (3 ml) and treated with sodium iodide (0.01 g, 0.06 mmol) and then 1-(methylamino)- 4-thiopyridone (0.008 g, 0.06 mmol). After stirring for 1.5h the solution was added dropwise to ether (40 ml). The product was filtered off and washed with ether, then water, and dried in vacuo (0.046 g, 68%); $\delta_H$ (CDCl$_3$) 3.04 (3H,d, J 6 Hz), 3.34 and 3.57 (2H,ABq, J 18 Hz), 3.82 (3H,s), 4.20 and 4.44 (2H,ABq, J 13 Hz), 5.07 (1H,d, J 5 Hz), 5.22 and 5.30 (2H,ABq, J 11.5 Hz), 6.04 (1H,dd, J 9 and 5 Hz), 6.43 (1H,s), 6.72 (1H,s,exch), 6.91 and 7.38 (4H,2d, J 8.5 Hz), 7.06 (1H,d, J 9 Hz,exch), 7.2–7.38 (30H ,m), 7.61 (2H,d, J 7 Hz), 8.65 (1H,q, J 6 Hz), and 8.75 (2H,d, J 7 Hz); m/z (F.A.B., 3 nitrobenzylalcohol/sodium acetate) M$^+$ 1126.

c) [6R,7R]-7-[2-(2-Amino-4-thiazolyl)- 2-(Z)-(hydroxyimino)acetamido]-3-[1-(methylamino)pyridinium- 4-thiomethyl]ceph-3-em-4-carboxylate The material from Example 9(b) (0.044 g, 0.035 mmol) was dissolved in trifluoroacetic acid (1 ml) with sonication for 3 minutes and then filtered through kieselguhr into ether (40 ml). The kieselguhr pad was washed with dichloromethane (3×1 ml). The precipitated product was filtered and then purified by chromatography on HP20SS eluting with water, tetrahydrofuran mixtures. Fractions containing product were combined, evaporated to low volume and freeze dried to give the title compound (0.009 g, 50%); $v_{max}$ (KBr), 1764, 1660 (sh), 1617 and 1528 cm$^1$; $\delta_H$ (D$_2$O) 3.00 (3H,s), 3.43 and 3.71 (2H,ABq, J 17.5 Hz), 4.11 and 4.41 (2H,ABq, J 13.5 Hz), 5.15 (1H,d, J 5 Hz), 5.77 (1H,d, 5 Hz), 6.92 (1H,s), 7.78(2H,d, J 7 Hz), and 8.50 (2H,d, 7 Hz); m/z (F.A.B., thioglycerol) MH$^+$ 522.

EXAMPLE 10

[6R,7R]-7-[2-(2-Amino-4-thiazolyl)- 2-(Z)-(methoxyimino)acetamido]-3-[1-(4-carboxybutan-1-yl)aminopyridinium- 4-thiomethyl]ceph-3-em-4-carboxylate sodium salt a) 4-Methoxybenzyl [6R,7R]-7-[2-(Z)-(methoxyimino)-2-(2-tritylamino-4-thiazolyl)acetamido]-3-[ 1-(2-oxopiperidin-1-yl)pyridinium-4-thiomethyl]ceph-3-em- 4-carboxylate iodide 4-Methoxybenzyl [6R,7R]-3-(chloromethyl)-7-[ 2-(Z)-(methoxyimino)-2-(2-tritylamino-4-thiazolyl)acetamido]-ceph-3-em-4-carboxylate (0.1 g, 0.13 mmol) was reacted with 1-(2-oxopiperidin-1-yl)-4-thiopyridone (0.0244 g, 0.13 mmol) and sodium iodide (0.127 g, 0.1 mmol) in acetonitrile (5 ml) as described in Example 14(a). The product was obtained after chromatography on silica gel 60, eluting with dichloromethane, ethyl acetate and finally mixtures of methanol in dichloromethane, as a yellow foam (0.078 g, 56%); $v_{max}$ (CH$_2$Cl$_2$) 1780, 1680, and 1610 cm$^{-1}$; $\delta_H$ (CDCl$_3$) 1.80–2.20 (4H, m), 2.35–2.75 (2H, m), 2.90–3.30 (2H, m), 3.50–4.20 (5H, m), 4.30–4.65 (2H, m), 4.90–5.30 (3H, m), 6.43 (1H, s), 6.70–7.40 (19H,m), 7.80–8.10 (2H, m), and 8.70–9.15 (2H, m); m/z (F.A.B., thioglycerol) MH$^+$ 966.

b) [6R,7R]-7-[2-(2-Amino-4-thiazolyl)- 2-(Z)-(methoxyimino)acetamido]-3-[1-(4-carboxybutan- 1-yl)aminopyridinium-4-thiomethyl]ceph-3-em-4-carboxylate sodium salt The product of Example 10(a) (0.078 g, 0.07 mmol) was deprotected with trifluoroacetic acid (0.0488 g, 4.3 mmol) in dichloromethane (5 ml) at room temperature as described in Example 8(c). Chromatography of the crude product on Diaion HP20SS resin, eluting with mixtures of tetrahydrofuran in water, gave the title product (0.0079 g, 17%); $v_{max}$ (KBr) 1762, 1664 and 1617 cm$^{-1}$; $\delta_H$ [D$_2$O+(CD$_3$)$_2$CO] 1.39–1.66 (4H, m), 2.08–2.19 (2H, m), 3.25 (2H, t, J 7 Hz), 3.40 and 3.67 (2H, ABq, J 18 Hz), 3.92 (3H, s), 4.11 and 4.36 (2H, ABq, J 14 Hz), 5.12 (1H, d, J 5 Hz), 5.71 (1H, d, J 5 Hz), 6.93 (1H, s), 7.76 (2H, d, J 7 Hz), 8.48 (2H, d, J 7 Hz); m/z (F.A.B., thioglycerol) MH$^+$ 644.

EXAMPLE 11

[6R,7R]-7-[2-(2-Amino-4-thiazolyl)- 2-(Z)-(ethoxyimino)-acetamido]-3-[1-(methylamino)pyridinium- 4-thiomethyl]-ceph-3-em-4-carboxylate a) 4-Methoxybenzyl[6R,7R]-7-amino-3-[ 1-(N-t-butyloxycarbonyl-N-methylamino)pyridinium-4-thiomethyl] ceph-3-em-4-carboxylate iodide 4-Methoxybenzyl [6R,7R]-7-amino- 3-(chloromethyl)ceph-3-em-4-carboxylate hydrochloride (0.405 g, 1 mmol) was partitioned between ethyl acetate (50 ml) and saturated, aqueous sodium hydrogen carbonate (25 ml).

The phases were separated and the organic phase washed with water, saturated brine, dried (MgSO$_4$) and evaporated to dryness under reduced pressure. The residue was redissolved in acetonitrile (10 ml) and treated with 1-[N-(t-butyloxycarbonyl)-N-methylamino]- 4-thiopyridone (0.24 g, 1 mmol) and sodium iodide (0.15 g, 1 mmol). After 1h the volatiles were removed under reduced pressure and the residue chromatographed on silica gel 60, eluting with dichloromethane, ethyl acetate then mixtures of methanol in dichloromethane, to give the title compound (0.617 g, 90%); $v_{max}$ (KBr) 1772, 1718 and 1614 cm$^{-1}$; $\delta_H$ (CDCl$_3$) 1.54 (9H, s), 1.72 (2H, brs, exch), 3.49 and 3.87 (2H, m), 3.69 (3H, s), 3.81 (3H, s), 4.46 and 4.53 (2H, ABq, J 13 Hz), 4.79 (1H, d, J 5 Hz), 5.01 (1H, d, J 5 Hz), 5.20 and 5.29 (2H, ABq, J 12 Hz), 6.88 (2H, d, J 9 Hz), 7.37 (2H, d, J 9 Hz), 8.11 (2H, d, J 7 Hz), and 8.61 (2H, d, J 7 Hz); m/z (F.A.B., 3-nitrobenzyl alcohol) M$^+$ 573.

b) 4-Methoxybenzyl [6R,7R]-3-[1-[ N-(t-butyloxycarbonyl)-N-methylamino]pyridinium-4-thiomethyl]- 7-[2-(Z)-(ethoxyimino)-2-(2-tritylamino- 4-thiazolyl)acetamido] ceph-3-em-4-carboxylate iodide 2-(Z)-(Ethoxyimino)-2-(2-tritylamino-4-thiazolyl)acetic acid (0.431 g, 0.94 mmol) was dissolved in dry N,N-dimethylformamide (5 ml) under argon and the solution cooled to −40° C. N,N-Diisopropylethylamine (0.122 g, 0.94 mmol) then methanesulphonyl chloride (0.108 g, 0.94 mmol) were added and the mixture stirred at −20° C. for 0.5h. The mixture was cooled to −40° C. and treated with a solution of 4-methoxybenzyl [6R,7R]- 7-amino-3-[1-[N-(t-butyloxycarbonyl)-N-methylamino]pyridinium- 4-thiomethyl]ceph-3-em-4-carboxylate iodide (0.6 g, 0.86 mmol) and pyridine (0.074 g, 0.94 mmol) in dry dichloromethane (10 ml). The resulting mixture was allowed to regain room temperature then stirred for 1h before being diluted with dichloromethane (50 ml). This mixture was washed with water (5×), saturated brine, dried (MgSO$_4$) and evaporated to dryness under reduced pressure. Chromatography on silica gel 60, eluting with dichloromethane, ethyl acetate then mixtures of methanol in dichloromethane, gave the title compound (0.526 g, 54%); $v_{max}$ (CH$_2$Cl$_2$) 1785, 1725 br, 1670 and 1615 cm$^{-1}$; $\delta_H$ (CDCl$_3$) 1.34 (3H, t, J 7 Hz), 1.52 (9H, s), 3.55 and 3.87 (2H, ABq, J 19 Hz), 3.69 (3H, s), 3.81 (3H, s), 4.36 (2H, q, J 7 Hz), 4.52 and 4.58 (2H, ABq, J 13 Hz), 5.12 (1H, d, J 5 Hz), 5.23 and 5.27 (2H, ABq, J 12 Hz), 5.98 (1H, dd, J 5 and 9 Hz), 6.72 (1H, s), 6.81 (1H, d, J 9 Hz, exch.), 6.88 (2H, d, J 9 Hz), 6.99 (1H, brs, exch.), 7.21–7.40 (17H, m), 8.09 (2H, d, J 7 Hz), and 8.56 (2H, d, J 7 Hz); m/z (F.A.B., thioglycerol) M$^+$ 1012.

c) [6R,7R]-7-[2-(2-Amino-4-thiazolyl)- 2-(Z)-(ethoxyimino]acetamido]-3-[1-(methylamino)pyridinium- 4-thiomethyl)ceph-3-em-4-carboxylate The product of Example 11(b) (0.52 g, 0.46 mmol) was deprotected as in Example 2(i,b) to give the title compound (0.081 g, 32%); $v_{max}$ (KBr) 1762, 1670, and 1618 cm$^{-1}$; $\delta_H$ [D$_2$O+(CD$_3$)$_2$CO] 1.27 (3H, t, J 7 Hz), 3.02 (3H, s), 3.45 and 3.71 (2H, ABq, J 18 Hz), 4.13 and 4.42 (2H, ABq, J 14 Hz), 4.23 (2H, q, J 7 Hz), 5.16 (1H, d, J 5 Hz), 5.77 (1H, d, J 5 Hz), 6.94 (1H, s), 7.81 (2H, d, J 7 Hz), and 8.53 (2H, d, J 7 Hz); m/z (F.A.B., thioglycerol) MH$^+$ 550.

EXAMPLE 12

[6R,7R]-3-[1-[(2S)-2-Amino-2-(methoxycarbonyl)ethylamino] pyridinium-4-thiomethyl]-7-[2-(2-amino- 4-thiazolyl)-2-(Z)-(methoxyimino)acetamido]ceph-3-em- 4-carboxylate a) 4-Methoxybenzyl [6R,7R]-3-[1-[(2S)- 2-(t-butyloxycarbonylamino)-2-(methoxycarbonyl)ethylamino] pyridinium-4-thiomethyl]-7-[2-(Z)-(methoxyimino)-2-( 2-tritylamino-4-thiazolyl)acetamido]ceph-3-em- 4-carboxylate iodide 1-[(3S)-3-(t-Butyloxycarbonylamino)-2-oxoazetidin-1-yl]-4-thiopyridone (0.075 g, 0.26 mmol) was dissolved in a mixture of tetrahydrofuran (2 ml), N,N-dimethylformamide (2 ml) and acetone (2 ml) with warming and the solution treated with a solution of 4-methoxybenzyl [6R, 7R]- 3-(chloromethyl)-7-[2-(Z)-(methoxyimino)-2-( 2-tritylamino-4-thiazolyl)acetamido]ceph-3-em-4-carboxylate (0.207 g, 0.26 mmol) and sodium iodide (0.039 g, 0.26 mmol) in acetone (5 ml). After 1.5h, the volatiles were removed under reduced pressure and diethyl ether (50 ml) added to the residue. The precipitate was collected by filtration, washed with diethyl ether and dried in air. The dried solid was redissolved in dry dichloromethane and the title compound obtained by chromatography on silica gel 60, eluting with dichloromethane, ethyl acetate then mixtures of methanol in dichloromethane (0.0514 g, 16%); $v_{max}$ (CH$_2$Cl$_2$) 1775, 1690 br, and 1610 cm$^{-1}$, $\delta_H$ (CDCl$_3$) 1.44 (9H, s), 3.45–3.87 (10H, m), 4.07 (3H, s), 4.42–4.49 (1H, m), 4.27 and 4.49 (2H, ABq, J 13 Hz), 5.09 (1H, d, J 5 Hz), 5.23 and 5.27 (2H, ABq, J 12 Hz), 5.60 (1H, d, J 8 Hz, exch.), 5.94 (1H, dd, J 5 and 8 Hz), 6.81 (1H, s), 6.81 (1H, d, J 8 Hz, exch.), 6.90 (2H, d, J 8 Hz), 7.00 (1H, s), 7.21–7.40 (17H, m), 7.69 (2H, d, J 7 Hz), 8.78 (1H, brm, exch.), and 8.90 (2H, d, J 7 Hz); m/z (F.A.B., thioglycerol) MH$^+$ 1086.

b) [6R,7R]-3-[1-[(2S)-2-Amino- 2-(methoxycarbonyl)ethylamino]pyridinium-4-thiomethyl]-7-[2-( 2-amino-4-thiazolyl)-2-(Z)-(methoxyimino)acetamido]ceph-3-em-4-carboxylate The product of Example 12(a) (0.05 g, 0.04 mmol) was deprotected as in Example 2(i,b) to give the title compound (0.0128 g, 49%); $v_{max}$ (KBr) 1758 br, 1669, and 1617 cm$^{-1}$; $\delta_H$ [D$_2$O+(CD$_3$)$_2$CO] 3.39–3.84 (5H, m), 3.69 (3H, s), 3.94 (3H, s), 5.14 (1H, d, J 5 Hz), 5.74 (1H, d, J 5 Hz), 6.96 (1H, s), 7.80 (2H, d, J 6 Hz), and 8.52 (2H, d, J 6 Hz); m/z (F.A.B.,thioglycerol), MH$^+$ 623.

EXAMPLE 13

[6R,7R]-7-[2-(2-Amino-4-thiazolyl )- 2-(Z)-(methoxyimino)acetamido]-3-[1-(cyclopropylmethylamino)pyridinium-4-thiomethyl]ceph-3-em-4-carboxylate a) 4-Methoxybenzyl [6R,7R]-3-[ 1-[N-(t-butyloxycarbonyl-N-(cyclopropylmethyl)amino]pyridinium- 4-thiomethyl]-7-[2-(Z)-(methoxyimino)-2-( 2-tritylamino-4-thiazolyl)acetamido]ceph-3-em-4-carboxylate iodide 4-Methoxybenzyl [6R,7R]-3-(chloromethyl)-7-[ 2-(Z)-(methoxyimino)-2-(2-tritylamino-4-thiazolyl)acetamido] ceph-3-em-4-carboxylate (0.10 g, 0.12 mmol) in dichloromethane (5 ml) was treated with 1-[ N-(t-butyloxycarbonyl)-N-(cyclopropylmethyl)amino]-4-thiopyridone (0.07 g, 0.25 mmol) and sodium iodide (0.02 g, 0.13 mmol), the mixture was stirred for 3h, then evaporated under reduced pressure. Purification on silica gel 60 eluting with ethanol, dichloromethane mixtures gave the title compound (0.098 g, 68%); $v_{max}$ (KBr) 1782, 1726, 1677, and 1613 cm$^{-1}$; $\delta_H$ (CDCl$_3$) 0.21 (2H, q, J 5 Hz), 0.62 (2H, q, J 7.5 Hz), 0.83–1.15 (1H, m), 1.52 (9H, s), 3.57 (1H, d, J 19 Hz), 3.75–3.97 (6H, m), 4.07 (3H, s), 4.56 and 4.65 (2H, ABq, J 12 Hz), 5.09 (1H, d, J 5 Hz), 5.19 and 5.25 (2H, ABq, J 12 Hz), 5.95 (1H, 2d, J 9 and J 12 Hz), 6.71 (1H, s), 6.89 (2H, d), 6.90–7.50 (17H, m), 8.21 (2H, d, J 7 Hz), and 8.55 (2H, d, J 7 Hz); m/z (F.A.B., 3-nitrobenzylalcohol) M$^+$ 1038.

b) [6R,7R]-7-[2-(2-Amino-4-thiazolyl)- 2-(Z)-(methoxyimino)acetamido]-3-[1-(cyclopropylmethylamino)pyridinium- 4-thiomethyl]ceph-3-em-4-carboxylate The product of Example 13(a) (0.09 g, 0.077 mmol) was treated with trifluoroacetic acid (1.0 ml, 13 mmol). The reaction mixture was stirred for 10 minutes then diluted with toluene (2 ml) and evaporated under reduced pressure. Purification on Diaion HP20SS resin eluting with acetone, water mixtures gave the title compound (0.026 g, 58%); $v_{max}$ (KBr) 1765, 1670, and 1619 cm$^{-1}$; $\delta_H$ (D$_2$O) 0.37 (2H, m), 0.44 (2H, m), 0.77–0.98 (1H, m), 3.10 (2H, d, J 7 Hz), 3.42 and 3.70 (2H, ABq, J 17.5 Hz), 3.94 (3H, s), 4.11 and 4.40 (2H, ABq, J 14 Hz), 5.13 (1H, d, J 5 Hz), 5.72 (1H, d, J 5 Hz), 6.97 (1H, s), 7.78 (2H, d), and 8.50 (2H, d, J 7 Hz); m/z (F.A.B., thioglycerol) MH$^+$ 576.

EXAMPLE 14

[6R,7R]-3-(1-Aminopyridinium-4-thiomethyl)-7-[ 2-amino-4-thiazolyl)-2-(Z)-(methoxyimino)acetamido]ceph- 3-em-4-carboxylate a) 4-Methoxybenzyl [6R,7R]-3-(1-aminopyridinium-4-thiomethyl)-7-[2-(Z)-(methoxyimino)-2-(2-tritylamino-4-thiazolyl)acetamido]ceph-3-em-4-carboxylate iodide 4-Methoxybenzyl [6R,7R]-3-(chloromethyl)-7-[ 2-(Z)-(methoxyimino)-2-(2-tritylamino-4-thiazolyl)acetamido] ceph-3-em-4-carboxylate (0.20 g, 0.25 mmol) in acetonitrile (10 ml) was treated with 1-amino-4-thiopyridone (0.16 g, 1.27 mmol) and sodium iodide (0.038 g, 0.25 mmol). The mixture was stirred for 2.5h, filtered through celite and evaporated to dryness under reduced pressure. Purification on silica gel 60 eluting with ethanol, dichloromethane (1:9) gave the title compound (0.178 g, 64%); $v_{max}$ (KBr) 1781, 1719, 1676, 1630, and 1611 cm$^1$; $\delta_H$ (CDCl$_3$), 3.53 and 3.72 (2H, ABq, J 18 Hz), 3.77 (3H, s), 4.02 (3H, s), 4.20 and 4.45 (2H, ABq, J 12.5 Hz), 5.08 (1H, d, J 5 Hz), 5.18 and 5.24 (2H, ABq, J 12 Hz), 5.85 (1H, dd, J 5 and 9 Hz) 6.60 (1H, s), 6.85 (2H, d, J 8.5 Hz), 7.00–7.45 (18H, m), 7.53 (2H, s), 7.61 (2H, d, J 7 Hz), and 8.63 (2H, d, J 7 Hz); m/z (F.A.B., thioglycerol) M$^+$ 884.

b) [6R,7R]-3-(1-Aminopyridinium-4-thiomethyl)- 7-[2-(amino-4-thiazoyl)-2-(Z)-(methoxyimino)acetamido]ceph-3-em-4-carboxylate The product from Example 14(a) (0.238 g, 0.24 mmol) in dichloromethane (10 ml) was treated with trifluoroacetic acid (0.55 ml, 7.0 mmol). The mixture was stirred for 1h, diluted with toluene (2 ml) and evaporated to dryness under reduced pressure. The residue was dissolved in the minimum volume of acetonitrile and added dropwise to vigorously stirred diethyl ether (30 ml). The precipitate was filtered, dried, and purified on HP20SS resin eluting with water, tetrahydrofuran mixtures to give the title compound (0.045 g, 37%). The product obtained was identical to that described in Example 4(b).

EXAMPLE 15

[6R,7R]-7-[2-Amino-4-thiazolyl)-2-(Z)-(methoxyimino)acetamido]- 3-[1-(isopropylidineamino)pyridinium-4-thiomethyl] ceph-3-em-4-carboxylate

[6R,7R]-3-(1-Aminopyridinium-4-thiomethyl)-7-[2-( 2-amino-4-thiazolyl)-2-(Z)-(methoxyimino)acetamido] ceph- 3-em-4-carboxylate (0.02 g, 0.038 mmol) in acetone, (0.5 ml), and water (0.5 ml) was stirred for 24h, evaporated under reduced pressure to remove acetone and then freeze dried to give the title compound (0.019 g, 88%); $v_{max}$ (KBr) 1769, 1670, and 1612 cm$^{-1}$; $\delta_H$ (D$_2$O) 1.93 (3H, s), 2.31 (3H, s), 3.45 and 3.73 (2H, ABq, J 17.5 Hz), 3.96 (3H, s), 4.13 and 4.43 (2H, ABq, J 13.5 Hz), 5.16 (1H, d, J 5 Hz), 5.75 (1H, d, J 5 Hz), 7.00 (1H, s), 7.86 (2H, d, J 7 Hz), and 8.26 (2H, d, J 7 Hz); m/z (F.A.B., thioglycerol) MH$^+$ 562.

EXAMPLE 16

[6R,7R]-7-[2-(2-Amino-4-thiazoyl)-2-(Z)-(methoxyimino)acetamido]-3-[1-(propylamino)pyridinium-4-thiomethyl] ceph- 3-em-4-carboxylate a) 4-Methoxybenzyl [6R,7R]-7-[2-(Z)-(methoxyimino)-2-( 2-tritylamino-4-thiazolyl]acetamido]-3-[1-(propylamino)pyridinium- 4-thiomethyl]ceph-3-em-4-carboxylate iodide 4-Methoxybenzyl [6R,7R]-3-(chloromethyl)-7-[ 2-(Z)-(methoxyimino)-2-(2-tritylamino-4-thiazolyl)acetamido] ceph- 3-em-4-carboxylate (0.34 g, 0.43 mmol) in acetonitrile (15 ml) was treated with 1-(propylamino)-4-thiopyridone (0.074 g, 0.044 mmol) and sodium iodide (0.064 g, 0.43 mmol). The mixture was stirred for 35 minutes, filtered and then evaporated under reduced pressure. Purification on silica gel 60 eluting with ethanol, dichloromethane mixtures gave the title compound (0.389, 97%); $\delta_H$ (CDCl$_3$) 1.02 (3H, t, J 7 Hz), 1.68–1.75 (2H, m), 3.25 (2H, q, J 7 Hz), 3.52 and 3.82 (2H, ABq, J 18 Hz), 3.80 (3H, s), 4.08 (3H, s), 4.29 and 4.53 (2H, ABq, J 13 Hz), 5.09 (1H, d, J 5 Hz), 5.23 (2H, ABq, J 12 Hz), 5.94 (1H, 2d, J 5 Hz and 9 Hz), 6.71 (1H, s), 6.80 (1H, d, J 9 Hz), 7.02 (1H, s), 6.90 and 7.35 (4H, 2d, J 8 Hz), 7.25–7.40 (15H, m), 7.72 (2H, d, J 7 Hz), 8.32–8.38 (1H, m), and 8.80 (2H, d, J 7 Hz); m/z (F.A.B., thioglycerol) MH$^+$ 926.

b) [6R,7R]-7-2-(2-Amino-4-thiazolyl)- 2-(Z)-(methoxyimino)acetamido]-3-[1-(propylamino)pyridinium- 4-thiomethyl]ceph-3-em-4-carboxylate The product of Example 16(a) (0.38 g, 0.41 mmol) was dissolved in dichloromethane (20 ml), treated with trifluoroacetic acid and stirred at room temperature for 0.5h. Dilution with toluene (5 ml), evaporation under reduced pressure and purification on Diaion HP20SS resin gave the title compound (0.078 g, 34% ); $v_{max}$ (KBr) 1768, 1671, and 1617 cm$^{-1}$; $\delta_H$(D$_2$O) 0.9 (3H, t, J 7 Hz), 1.5 (2H, q, J 7 Hz), 3.2 (2H, t, J 7 Hz), 3.42 and 3.71 (2H, ABq, J 17.5 Hz) J 3.96 (3H, s), 4.1 and 4.4 (2H, ABq, J 14 Hz), 5.13 (1H, d, J 5 Hz), 5.72 (1H, d, J 5 Hz), 7.0 (1H, S), 7.78 (2H, d, J 7 Hz), and 8.48 (2H, d, J 7 Hz); m/z (F.A.B., thioglycerol) MH$^+$ 564.

EXAMPLE 17

[6R,7R]-7-[2-(2-Amino-4-thiazolyl )- 2-(Z)-(methoxyimino)acetamido]-3-[1-(cyclopentylamino)pyridinium- 4-thiomethyl]ceph-3-em-4-carboxylate a) 4-Methoxybenzyl [6R,7R]-3-[1-[ N-(t-butyloxycarbonyl)-N-(cyclopentyl)amino]pyridinium- 4-thiomethyl]-7-[2-(Z)-(methoxyimino)-2-(2-tritylamino-4-thiazolyl)acetamido] ceph-3-em-4-carboxylate iodide 4-Methoxybenzyl [6R,7R]-3-(chloromethyl)-7-[ 2-(Z)-(methoxyimino)-2-(2-tritylamino-4-thiazolyl)acetamido] ceph- 3-em-4-carboxylate (0.1 g, 0.126 mmol) in acetonitrile (5 ml) was treated with 1-[ N-(t-butyloxycarbonyl)-N-(cyclopentyl)amino]-4-thiopyridone (0.038 g, 0.126 mmol) and sodium iodide (0.018 g, 0.126 mmol). The mixture was stirred for 0.5h., filtered and then evaporated under reduced pressure. Purification on silica gel 60 eluting with ethanol, dichloromethane (1:9) gave the title compound (0.126 g, 95%); ν$_{max}$ (CH$_2$Cl$_2$) 1780, 1720, and 1605 cm$^{-1}$; δ$_H$ (CDCl$_3$) 1.52 (9H, s), 1.58–1.80 (2H, m), 1.62 (4H, s), 2.05–2.20 (2H, m), 3.57 and 3.95 (2H, ABq, J 19 Hz), 3.81 (3H, s), 4.07 (3H, s), 4.05–4.72 (1H, m), 5.08 (1H, d, J 5 Hz), 5.13–5.30 (2H, m), 5.96 (1H, 2d, J 5 and 9 Hz), 6.72 (1H, s), 6.90 and 7.36 (4H, 2d, J 9 Hz), 7.01 (1H, s), 7.24–7.36 (17H, m), and 8.31 (2H, d, J 8 Hz); m/z (F.A.B., thioglycerol) MH$^+$ 1052.

b) [6R,7R]-7-[2-(2-Amino-4-thiazolyl)- 2-(Z)-(methoxyimino)acetamido]-3-[1-cyclopentylamino)pyridinium-4-thiomethyl]ceph-3-em-4-carboxylate The product of Example 17(a) (0.12 g, 0.114 mmol) was treated with trifluoroacetic acid (1 ml) and stirred for 2 minutes, toluene (5 ml) was added and the mixture evaporated under reduced pressure. Purification on Diaion HP20SS resin gave the title compound (0.013 g, 19%); ν$_{max}$ (KBr) 1761, 1726, 1675, and 1613 cm$^{-1}$; δ$_H$ (D$_2$O) 1.35–1.86 (8H, m), 3.42 and 3.71 (2H, ABq, J 17.5 Hz), 3.94 (3H, s), 4.11 and 4.40 (2H, ABq, J 14 Hz), 4.70–4.98 (1H, m), 5.15 (1H, d, J 5 Hz), 5.73 (1H, d, J 5 Hz), 6.97 (1H, s), 7.78 (2H, d, J 7 Hz), and 8.48 (2H, d, J 7 Hz); m/z (F.A.B., thioglycerol) MH$^+$ 590.

EXAMPLE 18

[6R,7R]-7-[2-(2-Amino-4-thiazolyl)- 2-(Z)-(methoxyiminoacetamido]-3-[1-(prop-2-en-1-yl)aminopyridinium-4-thiomethyl]ceph-3em-4-carboxylate a) 4-Methoxybenzyl [6R,7R]-3-[1-[ N-(t-butyloxycarbonyl)-N-(prop-2-en-1-yl)amino]-7-[ 2-(Z)-(methoxyimino)-2-(2-tritylamino-4-thiazolyl)acetamido]ceph- 3-em-4-carboxylate 4-Methoxybenzyl [6R,7R]-3-(chloromethyl)-7-[ 2-(Z)-(methoxyimino)-2-(2-tritylamino-4-thiazolyl)acetamido]-ceph- 3-em-4-carboxylate (0.12 g, 0.15 mmol) in acetonitrile (5 ml) was treated with 1-[N-(t-butyloxycarbonyl)-N-(prop- 2-en-1-yl)amino]thiopyridone (0.045 g, 0.17 mmol) and sodium iodide (0.022 g, 0.148 mmol). The mixture was stirred for 0.5h. and then evaporated under reduced pressure. Purification on silica gel 60 eluting with ethanol, dichloromethane mixtures (1:19) gave the title compound (0.13 g, 84%); δ$_H$ (CDCl$_3$) 1.53 and 1.62 (9H, 2s), 3.55 and 3.90 (2H, ABq, J 18 Hz), 3.81 (3H, s), 4.07 (3H, s), 4.40–4.68 (2H, m), 5.00–5.48 (4H, m), 5.32–6.00 (2H, m), 6.70–6.80 (2H, m), 6.87 (2H, d, J 8 Hz), 7.20 (1H, s), 7.25–7.43 (17H, m), 8.14 (2H, d, J 7 Hz), and 8.49 (2H, d, J 7 Hz); m/z (F.A.B., thioglycerol) M$^+$ 1024.

b) [6R,7R]-7-[2-(2-Amino-4-thiazolyl)- 2-(Z)-(methoxyimino)acetamido]-3-[1-(prop-2-en- 1-yl)aminopyridinium-4-thiomethyl]ceph-3-em-4-carboxylate The product of Example 18(a) (0.13 g, 0.127 mmol) was treated with trifluoroacetic acid (2 ml). The reaction mixture was stirred for 3 minutes, toluene (5 ml) was added and then the mixture evaporated under reduced pressure. Purification on Diaion HP20SS resin gave the title compound (0.046 g, 65%); ν$_{max}$ (KBr) 1764, 1670, and 1617 cm$^{-1}$; δ$_H$ (D$_2$O) 3.44 and 3.72 (2H, ABq, J 17.5 Hz), 3.87 (2H, d), 3.96 (3H, s), 4.12 and 4.41 (2H, ABq, J 14 Hz), 5.00–5.29 (3H, m), 5.76 (1H, d, J 5 Hz), 5.80–6.00 (1H, m), 6.99 (1H, s), 7.78 (2H, d, J 7 Hz), and 8.46 (2H, d, J 7 Hz); m/z (F.A.B., thioglycerol) MH$^+$ 562.

EXAMPLE 19

[6R,7R]-7-[2-(2-Amino-4-thiazolyl )- 2-(Z)-(methoxyimino)acetamido]-3-[1-butylaminopyridinium- 4-thiomethyl] ceph-3-em-4-carboxylate a) 4-Methoxybenzyl [6R,7R]-3-[1-([ N-butyl-N-(t-butyloxycarbonyl)amino]pyridinium-4-thiomethyl]-7-[ 2-(Z)-(methoxyimino)-2-(tritylamino-4-thiazolyl)acetamido] ceph-3-em-4-carboxylate iodide 4-Methoxybenzyl [6R,7R]-3-(chloromethyl)-7-[ 2-(Z)-(methoxyimino)-2-(2-tritylamino-4-thiazolyl)acetamido] ceph- 3-em-4-carboxylate (0.1 g, 0.126 mmol) in acetonitrile (10 ml) was treated with 1-[N-butyl-N-(t-butyloxycarbonyl)amino]- 4-thiopyridone (0.04 g, 0.14 mmol) and sodium iodide (0.018 g, 0.12 mmol). The mixture was stirred for 0.5h and then evaporated under reduced pressure. Purification on silica gel 60 eluting with ethanol, dichloromethane (1:9) gave the title compound (0.11 g, 84%); δ$_H$ (CDCl$_3$) 0.91–1.10 (3H, m), 1.23–1.67 (4H, m), 1.45 and 1.50 (9H, 2s), 3.55 and 3.92 (2H, ABq, J 19 Hz), 3.81 (3H, s), 3.99 (2H, t J 7.5 Hz), 4.07 (3H, s), 4.56 and 4.64 (2H, ABq, J 12.5 Hz), 5.09 (1H, d, J 5 Hz), 5.23 (2H, d, J 2.5 Hz), 5.96 (1H, q, J 5 Hz), 6.72 (1H, S), 6.75 (1H, d, J 9 Hz), 6.89 (2H, d, J 9 Hz), 7.02 (1H, s), 7.24–7.43 (17H, m), 8.22 and 8.45 (4H, 2d, J 7 Hz), m/z (F.A.B., thioglycerol) M$^+$ 1040.

b) [6R,7R]-7-[2-(2-Amino-4-thiazolyl)- 2-(Z)-(methoxyimino)acetamido]-3-[1-(butylamino)pyridinium- 4-thiomethyl]ceph-3-em-4-carboxylate The product of Example 19(a) (0.105 g, 0.1 mmol) was treated with trifluoroacetic acid (2 ml). The reaction mixture was stirred for 3 minutes, toluene (5 ml) was added and the mixture evaporated under reduced pressure. Purification on Diaion HP20SS resin gave the title compound (0.017 g, 29%); ν$_{max}$ (KBr), 1761, 1670 and 1618 cm$^{-1}$; δ$_H$ (D$_2$O) 0.84 (3H, t, J 7 Hz), 1.21–1.53 (4H, m), 3.24 (2H, t, J 7 Hz), 3.41 and 3.70 (2H, ABq, J 18 Hz), 3.93 (3H, s), 4.09 and 4.39 (2H, ABq, J 14 Hz), 5.23 (1H, d, J 5 Hz), 5.72 (1H, d, J 5 Hz), 6.95 (1H, s), 7.76 (2H, d, J 7 Hz), and 8.47 (2H, d, J 7 Hz); m/z (F.A.B., thioglycerol) MH$^+$ 578.

EXAMPLE 20

[6R, 7R]-7-[2-(2-Amino-4-thiazolyl)- 2-(Z)(methoxyimino)acetamido]-3-[1-(hexylamino)pyridinium- 4-thiomethyl] -ceph-3-em-4-carboxylate a) 4-Methoxybenzyl [6R,7R]-3-[ 1-[N-(t-butyloxycarbonyl)-N-hexylamino]pyridinium-4-thiomethyl]-7-[ 2-(Z)-(methoxyimino)-2-(2-tritylamino-4-thiazolyl)acetamido] ceph- 3-em-4-carboxylate iodide 4-Methoxybenzyl [6R,7R]-3-(chloromethyl)-7-[ 2-(Z)-(methoxyimino)-2-(2-tritylamino-4-thiazolyl)acetamido] ceph- 3-em-4-carboxylate (0.1 g, 0.126 mmol) in acetonitrile (10 ml) was treated with 1-[ N-(t-butyloxycarbonyl)-N-hexylamino]-4-thiopyridone (0.05 g, 0.16 mmol) and sodium iodide (0.1 g, 0.12 mmol). The mixture was stirred for 35 minutes and evaporated to a small volume. This was then added to diethyl ether (30 ml) while stirring vigorously. The precipitate was filtered off and dried in vacuo (0.09 g, 90%) ν$_{max}$ (CH$_2$Cl$_2$) 1780, 1720, and 1605; δ$_H$ (CDCl$_3$) 0.83–0.96 (3H, m), 1.25–1.74 (17H, m), 3.56 and 3.83 (2H, ABq, J 19 Hz), 3.81 (3H, s), 3.98 (2H, t, J 7 Hz), 4.08 (3H, s), 4.55 and 4.64 (2H, ABq, J 12 Hz), 5.10 (1H, d, J 5 Hz), 5.23 (2H, d, J 1.5 Hz), 5.96 (1H, 2d, J 5 and 9 Hz), 6.73 (1H, br.s), 6.90 (1H, br.s), 6.89 (2H, d, J 8 Hz), 7.23–7.40 (17H, m), 8.18 (2H, d, J 7 Hz), and 8.41 (2H, d, J 7 Hz); m/z (F.A.B., thioglycerol) MH$^+$ 1068.

b) [6R,7R]-7-[2-(2-Amino-4-thiazolyl)- 2-(Z)-(methoxyimino)acetamido]-3-[1-(hexylamino)pyridinium- 4-thiomethyl]ceph-3-em-4-carboxylate The product of Example 20(a) (0.90 g, 0.84 mmol) was treated with trifluoroacetic acid (2 ml). The reaction mixture was stirred for 10 minutes, toluene (10 ml) was then added and the mixture evaporated under reduced pressure. Purification on Diaion HP20SS resin gave the title compound (0.023 g, 45%); $v_{max}$ (KBr) 1764, 1674, and 1619 cm$^{-1}$; $\delta_H$ (D$_2$O) 0.80 (3H, t, J 7 Hz), 1.16–1.57 (SH, m), 3.25 (2H, t, J 7 Hz), 3.41 and 3.69 (2H, ABq, J 18 Hz), 3.93 (3H, s), 4.12 and 4.40 (2H, ABq, J 14 Hz), 5.12 (1H, d, J 5 Hz), 5.71 (1H, d, J 5 Hz), 6.94 (1H, s), 7.79 (2H, d, J 7 Hz), and 8.49 (2H, d, J 7 Hz); m/z (F.A.B., thioglycerol) MH$^+$ 606.

EXAMPLE 21

[6R,7R]-7-[2-(2-Amino-4-thiazoyl)- 2-(Z)-(methoxyimino)acetamido]-3-[1-(1-isopropyl)aminopyridinium- 4-thiomethyl]ceph-3-em-4-carboxylate a) 4-Methoxybenzyl [6R,7R]-3-[1-[ N-(t-butyloxycarbonyl)-N-hexylamino]pyridinium-4-thiomethyl]-7-[ 2-(Z)-(methoxyimino)-2-(2-tritylamino-4-thiazolyl)acetamido] ceph- 3-em-4-carboxylate iodide 4-Methoxybenzyl [6R,7R]-3-(chloromethyl)-7-[ 2-(Z)-(methoxyimino)-2-(2-tritylamino-4-thiazolyl)acetamido] ceph- 3-em-4-carboxylate (0.14 g, 0.176 mmol) in acetonitrile (10 ml) was treated with 1-[N-(t-butyloxycarbonyl)-N-(1-isopropyl)amino]-4-thiopyridone (0.05 g, 0.186 mmol) and sodium iodide (0.026 g, 0.17 mmol). The mixture was stirred for 35 minutes, filtered and evaporated to a smaller volume under reduced pressure. This was then added dropwise to a stirred solution of diethylether (40 ml) and the precipitate was filtered off. $\delta_H$ (CDCl$_3$) interalia 1.32 (6H, d, J 7 Hz), 1.51 (9H, s), 3.59 and 3.87 (2H, ABq, J 19 Hz), 3.80 (3H, s), 3.75–3.86 (1H, m), 4.06 (3H, s), 4.58–4.82 (3H, m), 5.08 (1H, d, J 5 Hz), 5.21 (2H, d, J 3 Hz), 5.95 (1H, 2d, J 5 and 9 Hz), 6.69 (1H, s), 6.88 (2H, d, J 8 Hz), 7.20–7.45 (19H, m), and 8.30 (2H, d, J 7 Hz).

b) [6R,7R]-7-[2-(2-Amino-4-thiazolyl)- 2-(Z)-(methoxyimino)acetamido]-3-[1-(1-isopropyl)aminopyridinium-4-thiomethyl]ceph-3-em-4-carboxylate The product of Example 21(a) was treated with trifluoroacetic acid (2 ml). The reaction mixture was stirred for 10 minutes, toluene (2 ml) was added and the mixture was slowly filtered through Celite into a stirred solution of diethylether (40 ml). The precipitated product was filtered and dried in vacuo (0.078 g, 79%); $v_{max}$ (KBr) 1782, 1675, and 1623 cm$^{-1}$; $\delta_H$(D$_2$O) 1.08 (6H, d, J 6 Hz), 3.45 and 3.74 (2H, ABq, J 18 Hz), 3.54 (1H, t, J 6 Hz), 4.01 (3H, s), 4.30–4.50 (3H, m), 5.16 (1H, d, J 5 Hz), 5.73 (1H, d, J 5 Hz), 7.09 (1H, s), 7.79 (2H, d, J 7 Hz), and 8.47 (2H, d, J 7 Hz), m/z (F.A.B., thioglycerol ) MH$^+$ 564.

EXAMPLE 22

[6R,7R]-7-[2-(2-Amino-4-thiazolyl)- 2-(Z)-(methoxyimino)acetamido]-2-[1-[(2-hydroxyethyl)amino]pyridinium-4-thiomethyl]ceph-3-em-4-carboxylate a) 4-Methoxybenzyl [6R,7R]-3-[1-[ N-(t-butyloxycarbonyl)-N-(2-hydroxyethyl) amino]pyridinium- 4-thiomethyl]-7-[2-(Z)-(methoxyimino)-2-(2-tritylamino- 4-thiazolyl)acetamido]ceph-3-em-4-carboxylate iodide 4-Methoxybenzyl [6R,7R]-3-(chloromethyl)-7-[ 2-(Z)-(methoxyimino)-2-(2-tritylamino-4-thiazolyl)acetamido] ceph- 3-em-4-carboxylate (0.14 g, 0,176 mmol) in acetonitrile (10 ml) was treated with 1-[ N-(t-butyloxycarbonyl)-N-(2-hydroxyethyl)amino]-4-thiopyridone (0.05 g, 0.185 mmol) and sodium iodide (0.026 g, 0.17 mmol). The mixture was stirred for 35 minutes, filtered and evaporated to a smaller volume under reduced pressure. The solution was added dropwise to diethyl ether (40 ml), and the precipitate filtered off to give the title compound (0.156 g, 86%); $\delta_H$ (CDCl$_3$) 1.45–1.60 (9H, m), 3.55–3.65 (1H, m), 3.75–3.95 (7H, m), 4.08 (3H, s), 4.41 and 4.51 (2H, ABq, J 12 Hz), 5.15 (1H, d, J 5 Hz), 5.20 and 5.28 (2H, ABq, J 12 Hz), 5.93 (1H, q, J 5 Hz), 6.74 (1H, s), 6.89 and 7.36 (4H, 2d J 8 Hz), 7.25–7.35 (15H, m), 7.80 and 8.52 (4H, 2d, J 7 Hz); m/z (F.A.B., thioglycerol) M$^+$ 1028.

b) [6R,7R]-7-[2-(2-Amino-4-thiazolyl)- 2-(Z)-(methoxyimino)acetamido]-3-[1-(2-hydroxyethyl)aminopyridinium-4-thiomethyl]ceph-3 -em-4-carboxylate The product of Example 22(a) (0.151 g, 1.47 mmol) was treated with trifluoroacetic acid (2 ml). The reaction mixture was stirred for 10 minutes, toluene (10 ml) was added and the mixture evaporated under reduced pressure. Purification on Diaion HP20SS resin gave the title compound (0.022 g, 27%); $v_{max}$ (KBr) 1771, 1670, and 1619 cm$^{-1}$; $\delta_H$ (D$_2$O) 3.35–3.50 (3H, m), 3.60–3.78 (3H, m), 3.95 (3H, s), 4.12 and 4.41 (2H, ABq, J 14 Hz), 5.12 (1H, d, J 5 Hz), 5.72 (1H, d, J 5 Hz), 7.00 (1H, s), 7.78 and 8.53 (4H, 2d, J 7 Hz); m/z (F.A.B., thioglycerol) MH$^+$ 566.

EXAMPLE 23

Sodium [6R,7R]-7-[2-(2-amino-4-thiazolyl)- 2-(Z)-[[R,S]-carboxy(3,4-dihydroxyphenyl)methyloxyimino]acetamido]- 3-[1-(methylamino)pyridinium-4-thiomethyl]ceph-3 -em-4-carboxylate a) 4-Methoxybenzyl [6R,7R]3-(chloromethyl)-7-[ 2-(Z)-[R, S]-(3,4-diacetoxyphenyl)(diphenylmethyloxycarbonyl)-methyloxyimino]- 2-(2-tritylamino-4-thiazolyl)acetamido] ceph-3 -em-4-carboxylate 2-[(Z)-[R,S](3,4-Diacetoxyphenyl)(diphenylmethyloxycarbonyl)-methyloxyimino]- 2-(2-tritylamino-4-thiazolyl)acetic acid (0.8 g, 0.95 mmol) was dissolved in dichloromethane (16 ml) and treated with N,N-diisopropylethylamine (0.25 ml, 1.43 mmol). Methanesulphonyl chloride (0.11 ml, 1.40 mmol) was added dropwise to the stirred solution. After 1h, the mixture was treated dropwise with a solution of 4-methoxybenzyl [6R,7R]-7-amino- 3-(chloromethyl)ceph-3-em-4-carboxylate hydrochloride (0.85 g, 2.1 mmol) and N,N-diisopropylethylamine (0.72 ml, 4.2 mmol) in dichloromethane (20 ml). The mixture was stirred for 1.5h and evaporated to dryness. The residue was partitioned between ethyl acetate and water and the organic phase washed with dilute citric acid and brine, then dried and evaporated under reduced pressure. The residue was purified on silica gel 60, eluting with hexane, ethyl acetate mixtures, to give the title compound (0.85 g, 72%); $\delta_H$ (CDCl$_3$ +D$_2$O) 2.23, 2.26, 2.29 and 2.30 (each 3H, 4s), 3.15 and 3.33 (2H, ABq, J 18 Hz), 3.33 and 3.47 (2H, ABq, J 18 Hz), 3.81 (6H, s), 4.00 and 4.55 (2H, ABq, J 12 Hz), 4.00 and 4.62 (2H, ABq, J 12 Hz), 4.90 (1H, d, J 5 Hz), 4.97 (1H, d, J 5 Hz), 5.20 and 5.26 (each 2H, 2 ABq, J 12 Hz), 5.8–5.9 (2H, m), 6.01 (1H, s), 6.10 (1H, s), 6.76 (2H, s), 6.8–7.4 (approx66H, m), 8.18 (1H, brs), and 8.24 (1H, brs); m/z (F.A.B., 3-nitrobenzyl alcohol, sodium acetate) MNa$^+$ 1218.

b) 4-Methoxybenzyl [6R,7R]-7-[2-(Z)[[R,S]-( 3,4-diacetoxyphenyl)(diphenylmethyloxycarbonyl)methyloxyimino]- 2-(2-tritylamino-4-thiazolyl)acetamido]-3-[ 1-(methylamino)pyridinium-4-thiomethyl] ceph-3-em- 4-carboxylate iodide 4-Methoxybenzyl [6R,7R]-3-(chloromethyl)-7-[ 2-(Z)-[ [R,S]-(3,4-diacetoxyphenyl)(diphenylmethyloxycarbonyl)methyloxyimino]- 2-(2-tritylamino-4-thiazolyl)acetamido] ceph-3-em-4-carboxylate (0.2 g, 0.17 mmol) was dissolved in acetonitrile (10 ml) and treated with sodium iodide (0.025 g, 0.17 mmol). After 5 minutes 1-(methylamino)-4-thiopyridone (0.025 g, 0.18 mmol) was added and the mixture stirred for 3h. The mixture was added dropwise to stirred diethyl ether (70 ml). The solid was collected by filtration, washed with dry ether and water and dried at reduced pressure over KOH overnight (0.15 g, 65%); $v_{max}$ (KBr) 1775, 1724, 1684, 1617, and 1513 cm$^{-1}$; $\delta_H$ (CDCl$_3$ +D$_2$O) 2.21, 2.26, 2.29 and 2.31 (each 3H, 4s), 3.00 and 3.02 (each 3H, 2s), 3.16 and 3.25 (2H, ABq, J 16 Hz), 3.25 (2H, s), 3.81 (6H, s), 4.22 and 4.38 (2H, ABq, J 13 Hz), 4.25 and 4.38 (2H, ABq, J 13 Hz), 4.93 (1H, d, J 5 Hz), 5.00 (1H, d, J 5 Hz), 5.16 and 5.27 (2H, ABq, J 12 Hz), 5.18 and 5.28 (2H, ABq, J 12 Hz), 5.76 (1H, d, J 5 Hz), 5.81 (1H, d, J 5 Hz), 6.01 (1H, s), 6.10 (1H, s), 6.76 (2H, s), 6.8–7.4 (66H, m), 7.52 (2H, d, J 8 Hz), 7.57 (2H, d, J 8 Hz), and 8.72 (4H, d, J 8 Hz); m/z (F.A.B., thioglycerol) MH$^+$ 1300.

c) Sodium [6R,7R]-7-[2-(2-amino-4-thiazolyl)- 2-(Z)-[[R,S]-carboxy(3,4-diacetoxyphenyl)methyloxyimino]-acetamido]- 3-[1-(methylamino)pyridinium-4-thiomethyl]ceph-3-em-4-carboxylate 4-Methoxybenzyl [6R,7R]-7-[2-(Z)[[R,S]-( 3,4-diacetoxyphenyl)(diphenylmethyloxycarbonyl)methyloxyimino]-2-(2-tritylamino-4-thiazolyl)acetamido]-3-[ 1-(methylamino)pyridinium-4-thiomethyl]ceph-3-em-4-carboxylate iodide (0.15 g, 0.105 mmol) was dissolved in dichloromethane (10 ml) and treated with trifluoroacetic acid (0.5 ml, 6.5 mmol). The mixture was stirred for 1h. and evaporated to dryness under reduced pressure. The residue was triturated with diethyl ether (3×20 ml) and then dissolved in water with dilute aqueous sodium hydrogen carbonate to pH 7. The product was purified on Diaion HP20SS resin, eluting with water and mixtures of water and tetrahydrofuran. Fractions containing the product were combined and freeze dried to give the title compound (0.03 g, 36%); $v_{max}$ (KBr) 1764, 1670, 1617, 1529, and 1501 cm$^{-1}$; $\delta_H$ (D$_2$O) 2.29 (6H, s), 2.31 (6H, s), 2.99 (6H, s), 3.24 and 3.51 (2H, ABq, J 19 Hz), 3.24 and 3.53 (2H, ABq, J 19 Hz), 4.14 and 4.35 (2H, ABq, J 14 Hz), 4.14 and 4.37 (2H, ABq, J 14 Hz), 5.02 (1H, d, J 5 Hz), 5.03 (1H, d, J 5 Hz), 5.54 (2H, s), 5.64 (1H, d, J 5 Hz), 5.68 (1H, d, J 5 Hz), 6.98 (2H, s), 7.2–7.5 (6H, m), 7.79 (4H, d, J 7 Hz), and 8.48 (4H, broad); m/z (F.A.B., thioglycerol) J (H-Na)$^+$ 772.

d) Sodium [6R,7R]-7-[2-(2-amino-4-thiazolyl)- 2-(Z)-[ [R, S]carboxy(3,4-dihydroxyphenyl)methyloxyimino]-acetamido]- 3-[1-(methylamino)pyridinium-4-thiomethyl] ceph- 3-em-4-carboxylate Sodium [6R,7R]-7-[2-(2-amino-4-thiazolyl)- 2-(Z)-[[R,S]-carboxy(3,4-diacetoxyphenyl)methyloxyimino]acetamido]- 3-[1-(methylamino)pyridinium-4-thiomethyl]ceph-3-em-4-carboxylate (0.023 g, 0.03 mmol) was dissolved in water (5 ml) and methanol (5 ml) and treated with dilute sodium hydroxide to pH 9.4. After 5 minutes the mixture was neutralised with 0.1M hydrochloric acid and the solvent removed under reduced pressure. The product was purified on Diaion HP20SS resin, eluting with mixtures of water and tetrahydrofuran. Fractions containing product were combined and freeze dried to give the title compound (0.016 g, 75%); $v_{max}$ (KBr) 1762, 1660, 1617, and 1527 cm$^{-1}$; $\delta_H$ (D$_2$O) 3.00 (6H, s), 3.12 and 3.46 (2H, ABq, J 18 Hz), 3.15 and 3.46 (2H, ABq, J 18 Hz), 4.13 and 4.30 (2H, ABq, J 14 Hz), 4.13 and 4.36 (2H, ABq, J 14 Hz), 4.97 (1H, d, J 5 Hz), 4.99 (1H, d, J 5 Hz), 5.37 (2H, s), 5.58 (1H, d, J 5 Hz), 5.61 (1H, d, J 5 Hz), 6.75–6.92 (4H, m), 6.96 (4H, s), 7.79 (4H, d, J 7 Hz), and 8.47 (4H, d, J 7 Hz); m/z (F.A.B., thioglycerol) M(H-Na)$^+$ 688.

EXAMPLE 24

Sodium [6R,7R]-7-[2-(2-amino-4-thiazolyl)-2-(Z)-[ (S)-carboxy (3,4-dihydroxyphenyl)methyloxyimino]acetamido]- 3-[1-(methylamino)pyridinium-4-thiomethyl]ceph- 3-em-4-carboxylate The title compound was prepared from 2-[(Z)-(S)-( 3,4-diacetoxyphenyl)(diphenylmethyloxycarbonyl)-methyloxyimino]- 2-(2-tritylamino-4-thiazolyl)acetic acid using the method described in Example 23; $v_{max}$ (KBr) 1762, 1660 sh, 1617, 1528 and 1387 cm$^{-1}$; $\delta_H$(250 MHz D$_2$O) 3.01 (3H,s), 3.16 and 3.49 (2H, ABq, J=18 Hz), 4.16 and 4.30 (2H, ABq, J=14 Hz), 5.01 (1H, d, J=5 Hz), 5.38 (1H, s), 5.62 (1H, d, J=5 Hz), 6.80–6.97 (4H, m), 7.80 (2H, d, J=7 Hz), 8.48 (2H, d, J=7 Hz); m/z (F.A.B., thioglycerol) MH$^+$ 710.

EXAMPLE 25

Sodium [6R,7R]-7-[2-(2-amino-4-thiazolyl)-2-(Z)-[ (R)-carboxy (3,4-dihydroxyphenyl]methoxyimino]-acetamido]- 3-[1-(methylamino)pyridinium-4-thiomethyl]ceph-3-em-4-carboxylate The title compound was prepared from 2-[(Z)-(R)-(3,4-diacetoxyphenyl)(diphenylmethyloxycarbonyl)-methyloxyimino]- 2-(2-tritylamino-4-thiazolyl)acetic acid using the method described in Example 23, (0.037 g, 18%); $v_{max}$ (KBr) 1762, 1650 (sh), 1617, and 1527 cm$^{-1}$; $\delta_H$ (D$_2$O) 2.99 (3H, s), 3.13 and 3.45 (2H, ABq, J 17.5 Hz), 4.11 and 4.35 (2H, ABq, J 14 Hz), 4.96 (1H, d, J 5 Hz), 5.36 (1H, s), 5.59 (1H, d, J 5 Hz), 6.79 (1H, d, J 8 Hz), 6.86 (1H, dd, J 8 and 1.5 Hz), 6.95 (1H, s), 6.97 (1H, d, J 1.5 Hz), 7.77 (2H, d, J 7 Hz), and 8.46 (2H, d, J 7 Hz); m/z (F.A.B., thioglycerol) MH$^+$ 710.

EXAMPLE 26

Sodium [6R,7R]-3-[1-aminopyridinium-4-thiomethyl]-7-[ 2-(2-amino-4-thiazolyl)-2-(Z)-[(R,S)-carboxy ( 3,4-dihydroxyphenyl)methyloxyimino]acetamido]ceph-3-em- 4-carboxylate The title compound is prepared as described in Example 23 except that 1-amino-4-thiopyridone replaced 1-(methylamino)-4-thiopyridone.

EXAMPLE 27

Sodium [6R,7R]-3-[1-(acetylamino)pyridinium- 4-thiomethyl]-7-[2-(2-amino-4-thiazolyl)-2-(Z)-[(S)-carboxy-( 3,4-dihydroxyphenyl)methyloxyimino]acetamido]ceph- 3-em-4-carboxylate and Sodium [6R,7R]-3-[ 1-aminopyridinium-4-thiomethyl]-7-[2-( 2-amino-4-thiazolyl)-2-(Z)-[(S)-carboxy ( 3,4-dihydroxyphenyl)methyloxyimino]acetamido]ceph-3-em-4-carboxylate Sodium [6R,7R]-3-(1-aminopyridinium-4-thiomethyl)-7-[2-(2-amino-4-thiazolyl)-2-(Z)-[(S)-carboxy( 3,4-dihydroxyphenyl)methyloxyimino]acetamido]ceph-3-em-4-carboxylate was prepared from 2-[(Z)-(S)-( 3,4-diacetoxyphenyl)(diphenylmethyloxycarbonyl)methyloxyimino]- 2-(2-tritylamino-4-thiazolyl)acetic acid and 1-amino-4-thiopyridone using the method described in Example 23, (0.013 g, 7%); $v_{max}$ (KBr) 1762, 1603, and 1528 cm$^{-1}$; $\delta_H$ (D$_2$O) 3.11 and 3.47 (2H, ABq, J 18 Hz), 4.10 and 4.30 (2H, ABq, J 14 Hz), 4.98 (1H, d, J 4.5 Hz), 5.36 (1H, s), 5.62 (1H, d, J 4.5 Hz), 6.82 (1H, d, J 8 Hz), 6.89 (1H, dd, J 8 and 1 Hz), 6.97 (1H, s), 6.98 (1H, d, J 1 Hz), 7.74 (2H, d, J 6 Hz), and 8.37 (2H, d, J 6 Hz); m/z (F.A.B., thioglycerol) MH+ 696.

Also isolated by chromatography was sodium [6R,7R]-3-[1-(acetylamino)pyridinium-4-thiomethyl]-7-[ 2-(2-amino-4-thiazolyl)-2-(Z)-[(S)-carboxy(3,4-dihydroxy phenyl)methyloxyimino]acetamido]ceph-3-em-4-carboxylate (0.0467 g; 26%); $\nu_{max}$ (KBr) 1762 and 1612 cm$^{-1}$; $\delta_H$ (D$_2$O) 1.98 (3H,s), 3.10 and 3.52 (2H, ABq, J 17 Hz), 4.06 and 4.12 (2H, ABq, J 14 Hz), 5.00 (1H, d, J 5 Hz), 5.39 (1H, s), 5.65 (1H, d, J 5 Hz), 6.82–6.95 (3H, m), 7.02 (1H, s ), 7.70 (2H, d, J 7 Hz) and 8.13 (2H, d, J 7 Hz); m/z (F.A.B., thioglycerol) MNa+ 760 and MH+ 738.

EXAMPLE 28

Sodium [6R,7R]-3-[1-aminopyridinium-4-thiomethyl]-7-[2-(2-amino-4-thiazolyl)-2-(Z)-[(R)-carboxy ( 3,4-dihydroxyphenyl)methyloxyimino]acetamido]ceph-3-em- 4-carboxylate The title compound is prepared from 2-(Z)-[(R)-( 3,4-diacetoxyphenyl)(diphenylmethyl-oxycarbonyl)methyloxyimino]- 2-(2-tritylamino-4-thiazolyl)acetic acid and 1-amino-4-thiopyridone using the method described in Example 23.

EXAMPLE 29

[6R,7R]-3-(1-Amino-2,3-cyclopentenopyridinium- 4-thiomethyl)-7-[2-(2-amino-4-thiazolyl)-2-(Z)-(methoxyimino) acetamido]ceph-3-em-4-carboxylate a) 4-Methoxybenzyl [6R,7R]-3-[1-(t-butyloxycarbonylamino)- 2,3-cyclopentenopyridinium-4-thiomethyl]- 7-[2-(Z)-(methoxyimino)-2-(2-tritylamino-4-thiazolyl)acetamido] ceph-3-em-4-carboxylate iodide 4-Methoxybenzyl[6R,7R]-3-(chloromethyl)-7-[ 2-(Z)-(methoxyimino)-2-(2-tritylamino-4-thiazolyl)acetamido] ceph-3-em-4-carboxylate (0.125 g, 0.157 mmol) in acetonitrile (10 ml) was treated with sodium iodide (0.024 g, 0.16 mmol) followed by 1-(t-butyloxycarbonylamino)- 2,3-cyclopenteno-4-thiopyridone (0.083 g, 0.3 mmol). The reaction mixture was stirred for 3h, then evaporated to low volume and added to diethyl ether (40 ml). After being stirred for 20 minutes the precipitate was filtered to give the title compound (0.126 g, 78%); $\delta_H$ (CDCl$_3$) 1.54 (9H, s), 2.35 (2H, t, J 7.5 Hz), 2.96 (2H, t, J 7.35 Hz), 3.36–3.46 (2H, m), 3.46 and 3.70 (2H, ABq, J 18 Hz), 3.82 (3H, s), 4.08 (3H, s), 4.26 and 4.43 (2H, ABq, J 12.5 Hz), 5.09 (1H, d, J 5 Hz), 5.19 and 5.29 (2H, ABq, J 12 Hz), 5.94 (1H, q, J 5 Hz), 6.73 (1H, s), 6.90 and 7.22 (4H, 2d, J 8.5 Hz), 7.30 (15H, s), 7.50 and 8.14 (2H, 2d, J 7 Hz); m/z (F.A.B., thioglycerol/AcOH) M+ 1024.

b) [6R, 7R]-3-[1-Amino-2,3-cyclopentenopyridinium-4-thiomethyl]-7-[2-(2-amino-4-thiazolyl)- 2-(Z)-(methoxyimino)acetamido]ceph-3-em-4-carboxylate The product of example 29(a) (0.12 g, 0.12 mmol) was treated with trifluoroacetic acid (2 ml) and stirred at room temperature for 5 minutes. The mixture was diluted with toluene (5 ml) and evaporated to dryness. The residue was twice diluted with toluene and evaporated to dryness under reduced pressure. Purification on Diaion HP20SS resin eluting with water, tetrahydrofuran mixtures gave the title compound (0.029 g, 45%); $\nu_{max}$ (KBr) 1767, 1670, 1609 , and 1529 cm$^{-1}$; $\delta_H$ (D$_2$O) 2.26 (2H, t, J 7.5 Hz), 2.96 (2H, t, J 7.5 Hz), 3.26 (2H, t, J 7.5 Hz), 3.44 and 3.71 (2H, ABq, J 17.5 Hz), 3.95 (3H, s), 4.15 and 4.39 (2H, ABq, J 14 Hz), 5.13 (1H, d, J 4.5 Hz), 5.72 (1H, d, J 4.5 Hz), 6.96 (1H, s), 7.55 (1H, d, J 7 Hz), and 8.19 (1H, d, J 7 Hz); m/z (F.A.B., thioglycerol) MH+ 562.

EXAMPLE 30

[6R, 7R]-7-[2-(2-Amino-4-thiazolyl)-2-(Z)-(methoxyimino) acetamido]-3-[1-(2-pyridylamino)pyridinium- 4-thiomethyl]ceph-3-em-4-carboxylate a) 4-Methoxybenzyl [6R,7R]-7-[ 2-(Z)-(methoxyimino)-2-(2-tritylamino-4-thiazolyl)acetamido]-3-[ 1-(2-pyridylamino)pyridinium-4-thiomethyl]ceph-3-em- 4-carboxylate iodide 4-Methoxybenzyl [6R,7R]-3-(chloromethyl)-7-[ 2-(Z)-(methoxyimino)-2-(2-tritylamino-4-thiazolyl)acetamido] ceph-3-em-4-carboxylate (0.105 g, 0.13 mmol) was added to a solution of 1-(2-pyridylamino)- 4-thiopyridone (0.027 g, 0.13 mmol) in acetonitrile (4.7 ml) and N,N-dimethylformamide (0.3 ml) followed by sodium iodide (0.02 g, 0.13 mmol) in acetonitrile (0.4 ml). After 4.5h, the reaction mixture was filtered, concentrated to low volume and added to vigorously stirred ether (50 ml). The resulting precipitate was filtered off, washed with ether and dried in vacuo to give the title product (0.087 g, 70%); $\nu_{max}$ (CH$_2$Cl$_2$) 3400, 1784, 1719 and 1677 cm$^{-1}$; $\delta_H$ (CDCl$_3$) inter alia 3.52 and 3.78 (2H, ABq, J 21 Hz), 3.77 (3H, s), 4.08 (3H, s), 4.31 and 4.51 (2H, ABq, J 13 Hz), 5.09 (1H, d, J 4.4 Hz), 5.20 and 5.29 (2H, ABq, J 11.4 Hz), 5.95 (1H, dd, J 4.4 and 8.9 Hz), 6.72 (1H, s), 6.88 (2H, d, J 8.6 Hz), 7.31 (17H, m), 7.71 (3H, m), 8.03 (1H, m), and 8.54 (2H, d, J 6.4 Hz); m/z (F.A.B., thioglycerol-acetic acid) (MH-HI)+ 961.

b) [6R,7R]-7-[2-(2-Amino-4-thiazolyl)- 2-(Z)-(methoxyimino)acetamido]-3-[1-(2-pyridylamino) pyridinium-4-thiomethyl]ceph-3-em-4-carboxylate The product from Example 30(a) (0.087 g, 0.08 mmol) was suspended in dichloromethane (7 ml) and trifluoroacetic acid (0.37 ml, 4.8 mmol) added. After stirring for 2h, the reaction was diluted with toluene (5 ml) and the solution evaporated to dryness. Toluene (5 ml) was added and the mixture reevaporated; this was repeated.

After drying in vacuo for 10 minutes, the residue was triturated with ether, then dissolved in water at pH 7 and purified on Diaion HP20SS resin to afford the title product (0.02 g, 42%); $\nu_{max}$ (KBr) 1768, 1670 and 1617 cm$^{-1}$; $\delta_H$ (D$_2$O) 3.44 and 3.73 (2H, ABq, J 17.7 Hz), 3.93 (3H, s), 4.14 and 4.43 (2H, ABq, J 13.8 Hz), 5.15 (1H, d, J 4.7 Hz), 5.74 (1H, d, J 4.7 Hz), 6.7 (1H, m), 6.9 (1H, m), 6.96 (1H, s), 7.69 (1H, m), 7.86 (2H, d, J 6.4 Hz overlaps 1H, s), and 8.43 (2H, d, J 6.4 Hz); m/z (F.A.B., Thioglycerol-acetic acid) M+ 599.

EXAMPLE 31

[6R,7R]-7-[2-(2-Amino-4-thiazolyl)., 2-(Z)-(methoxyimino)acetamido]-3-[1-(3,5-dimethylisoxazol-4-yl) methylaminopyridinium-4-thiomethyl]ceph-3-em- 4-carboxylate a) 4-Methoxybenzyl [6R,7R]-3-[1-(3,5-dimethyl isoxazol-4-yl)methylaminopyridinium-4-thiomethyl]- 7-[2-(Z)-(methoxyimino)-2-(2-tritylamino-4-thiazolyl) acetamido] ceph-3-em-4-carboxylate iodide 4-Methoxybenzyl[6R,7R]-3-(chloromethyl)-7-[ 2-(Z)-(methoxyimino)-2-(2-tritylamino-4-thiazolyl)acetamido] ceph-3-em-4-carboxylate (0.09 g, 0.11 mmol) was reacted with 1-(3,5-dimethylisoxazol-4-yl)methylamino- 4-thiopyridone (0.029 g, 0.11 mmol) and sodium iodide (0.02 g, 0.11 mmol) for 3.5h as described in Example 30(a), to give the title product (0.122 g, 88%); $\nu_{max}$ (KBr) 1783, 1718, 1662, and 1617 cm$^{-1}$; $\delta_H$ [CDCl$_3$+ (CD$_3$)$_2$SO] 2.16 (3H, s), 2.28 (3H, s), 3.63 (2H, AA'), 3.81 (3H, s), 3.99 (3H, s), 4.12 and 4.69 (2H, ABq, 13.2 Hz), 4.24 (2H, d, J 4 Hz), 5.09 (1H, d, J 4.9 Hz), 5.19 and 5.26 (2H, ABq, J 11.8 Hz), 5.87 (1H, dd, J 4.9 and 8.4 Hz), 6.76 (1H, s), 6.89 (2H, d, J 8.6 Hz), 7.2–7.4 (17H, m), 7.55 (1H, br s, exch.) 7.84 (2H, d, J 7 Hz), 8.30 (1H, d, J 8.6 Hz), 8.70 (1H, t, J 4 Hz, exch.), and 8.76 (2H, d, J 7 Hz, exch.); m/z (F.A.B., Thioglycerol) MH⁺ 993.

b) [6R,7R]-7-[2-(2-Amino-4-thiazolyl)- 2-(Z)-(methoxyimino)acetamido]-3-[1-(3,5-dimethylisoxazol- 4-yl)methylaminopyridinium-4-thiomethyl]ceph-3 -em- 4-carboxylate The product from Example 31(a) (0.11 g, 0.098 mmol) was deprotected using trifluoroacetic acid as described in Example 30(b) to provide the title product (0.014 g, 23%); $v_{max}$ (KBr) 3391, 1768, 1669, 1619 and 1532 cm⁻¹; $\delta_H$ (D₂O) 2.07 (3H, s), 2.08 (3H, s), 3.46 and 3.66 (2H, ABq, J 17.7 Hz), 3.93 (3H, s), 4.21 (2H, s), 4.27 (2H, AA'), 5.14 (1H, d, J 4.7 Hz), 5.73 (1H, d, J 4.7 Hz), 6.96 (1H, s), 7.83 (2H, d, J 7.1 Hz), and 8.34 (2H, d, J 7.1 Hz); m/z (F.A.B., thioglycerol) MH⁺ 631.

EXAMPLE 32

[6R,7R]-7-[2-(2-Amino-4-thiazolyl)- 2-(Z)-(methoxyimino)acetamido]-3-[1-[N-(3,4-dihydroxybenzoyl)-N-methyl amino]pyridinium-4-thiomethyl]ceph-3-em-4-carboxylate a) 4-Methoxybenzyl [6R,7R]-3-[1-[N-[ 3,4-bis(4-methoxybenzyloxy)benzoyl]-N-methylamino]pyridinium- 4-thiomethyl]-7-[2-(Z)-(methoxyimino)-2-( 2-tritylamino-4-thiazolyl) acetamido]ceph-3-em-4-carboxylate iodide 4-Methoxybenzyl [6R,7R]-3-(iodomethyl)-7-[ 2-(Z)-(methoxyimino)-2-(2-tritylamino-4-thiazolyl)acetamido] ceph-3-em-4-carboxylate (0.089 g, 0.1 mmol) was dissolved in dichloromethane (10 ml) and treated with 1-[N-[ 3,4-bis-(4-methoxybenzoyloxy)benzoyl]-N-methylamino]- 4-thiopyridone (0.05 g, 0.1 mmol). When reaction was complete the mixture was evaporated to dryness under reduced pressure to give the title compound; $\delta_H$ (CDCl₃+D₂O) 3.47 and 3.75 (2H, ABq, J 18.5 Hz), 3.75 (3H, s), 3.76 (3H, s), 3.77 (3H, s), 3.80 (3H, s), 4.04 (3H, s), 4.35 and 4.50 (2H, ABq, J 13 Hz), 5.07 (1H, d, J 5 Hz), 5.12 (2H, s), 5.18 (2H, s), 5.18 and 5.27 (2H, ABq, J 12 Hz), 5.89 (1H, d, J 5 Hz), 6.70 (1H, s), 6.80–7.50 (30H, m), 7.85 (2H, d, J 6.5 Hz), and 8.77 (2H, d, J 6.5 Hz).

b) [6R, 7R]-7-[2-(2-Amino-4-thiazolyl)- 2-(Z)-(methoxyimino)acetamido]-3-[1-[N-( 3,4-dihydroxybenzoyl)-N-methylamino]pyridinium-4-thiomethyl] ceph-3-em-4-carboxylate 4-Methoxybenzyl [6R, 7R]-3-[N-[3,4-bis( 4-methoxybenzyloxy)benzoyl]-N-methylamino]-7-[ 2-(Z)-(methoxyimino)-2-(2-tritylamino-4-thiazolyl) acetamido]ceph-3-em-4-carboxylate iodide (0.12 g, 1.0 mmol) in dichloromethane (10 ml) was treated with trifluoroacetic acid (0.8 ml, 10.3 mmol) and stirred for 1.5h. Purification on Diaion HP20SS resin eluting with water, tetrahydrofuran mixtures gave the title compound (0.033 g, 49%); $v_{max}$ (KBr) 1767, 1669, 1616, and 1528 cm⁻¹; $\delta_H$ (D₂O) 3.35 and 3.59 (2H, ABq, J 17.5 Hz), 3.64 (3H, s), 3.84 (3H, s), 4.20 and 4.38 (2H, ABq, J 14 Hz), 5.05 (1H, d, J 4.5 Hz), 5.66 (1H, d, J 4.5 Hz), 6.81 (1H, d, J 7 Hz), 6.82 (1H, s), 7.01 (1H, s), 7.02 (1H, d, J 7 Hz), 7.94 (2H, d, J 7 Hz), and 8.67 (2H, d, J 7 Hz); m/z (F.A.B., thioglycerol) MH⁺ 672.

EXAMPLE 33

[6R,7R]-7-[2-(2-Amino-4-thiazolyl)- 2-(Z)-(hydroxyimino)acetamido]-3-[1-[N-(3,4-dihydroxybenzoyl)-N-methylamino] pyridinium-4-thiomethyl]ceph-3-em-4-carboxylate a) 4-Methoxybenzyl [6R,7R]-3-[1-[N-[3,4-bis-( 4-methoxybenzyloxy)benzoyl-N-methylamino]pyridinium- 4-thiomethyl]-7-[2-(tritylamino-4-thiazolyl)- 2-(Z)-(trityloxyimino)acetamido]ceph-3-em-4-carboxylate iodide 4-Methoxybenzyl [6R,7R]-3-(iodomethyl)-7-[2-( 2-tritylamino-4-thiazolyl)-2-(Z)-(trityloxyimino)acetamido]ceph- 3-em-4-carboxylate (0.10 g, 0.1 mmol) was reacted with 1-[N-[3,4-bis-(4-methoxybenzyloxy)benzoyl]-N-methylamino]- 4-thiopyridone (0.05 g, 0.1 mmol) by the method described in Example 32(a). Purification on silica gel eluting with mixtures of ethyl acetate and ethanol gave the title compound (0.056 g, 34%); $v_{max}$ (CH₂Cl₂) 1795, 1720, 1685, 1615, and 1515 cm⁻¹.

b) [6R, 7R]-7-[2-(2-Amino-4-thiazolyl)- 2-(Z)-(hydroxyimino)acetamido]-3-[1-[N-( 3,4-dihydroxybenzoyl)-N-methylamino]pyridinium-4-thiomethyl]ceph- 3-em-4-carboxylate 4-Methoxybenzyl [6R,7R]-3-[1-[N-[3,4-bis( 4-methoxybenzyloxy)benzoyl]-N-methylamino]pyridinium-4-thiomethyl]- 7-[2-(2-tritylamino-4-thiazolyl)-2-(Z)-(trityloxyimino)acetamido] ceph-3-em-4-carboxylate iodide (0.056 g, 0.035 mmol) was treated with trifluoroacetic acid (0.5 ml, 19 mmol) for 1h. The reaction mixture was evaporated to dryness under reduced pressure. The residue was triturated with diethyl ether (3×20 ml) before being dissolved in water maintained at pH₇ by addition of sodium hydrogen carbonate. Purification on Diaion HP20SS resin eluting with water, tetrahydrofuran mixtures gave the title compound (0.0066 g, 28%); $v_{max}$ (KBr), 1765, 1665, 1616, and 1530 cm⁻¹; $\delta_H$ [D₂O+ (CD₃)₂CO] 3.44 and 3.70 (2H, ABq, J 17 Hz), 3.74 (3H, s), 4.27 and 4.46 (2H, ABq, J 14 Hz), 5.17 (1H, d, J 4.5 Hz), 5.80 (1H, d, J 4.5 Hz), 6.80 (1H, d, J 8 Hz), 6.92 (1H, s), 7.06 (1H, s), 7.08 (1H, d, J 8 Hz), 8.00 (2H, d, J 7 Hz), and 8.74 (2H, d, J 7 Hz), m/z (F.A.B., thioglycerol, acetic acid) MH⁺ 658.

EXAMPLE 34

Sodium [6R,7R]-7-[2-(2-Amino-4-thiazolyl)-2-(Z)-( 1-carboxy-1-methylethoxyimino)acetamido]-3-[1-[N-( 3,4-dihydroxybenzoyl)-N-methylamino]pyridinium-4-thiomethyl] ceph- 3-em-4-carboxylate 4-Methoxybenzyl [6R,7R]-7-[2-(Z)-[ 1-(t-butyloxycarbonyl)-1-methylethoxyimino]-2-(2-tritylamino- 4-thiazolyl)acetamido]-3-[1-[N-[3,4-bis(4-methoxybenzyloxy)benzoyl]-N-methylamino] pyridinium-4-thiomethyl]ceph-3-em-4-carboxylate iodide 4-Methoxybenzyl [6R,7R]-7-[2-(Z)[1-(t-butyloxycarbonyl)- 1-methylethoxyimino]-2-(2-tritylamino-4-thiazolyl)acetamido]- 3-(chloromethyl)ceph-3-em-4-carboxylate (0.092 g, 0.1 mmol) in dichloromethane (5 ml) was treated with 1-[N-[3,4-bis(4-methoxybenzyloxy)benzoyl]-N-methylamino]- 4-thiopyridone (0.052 g, 0.1 mmol). After 1h sodium iodide (0.03 g, 0.2 mmol) was added and the reaction mixture was stirred overnight. Purification on silica gel, eluting with mixtures of ethyl acetate and ethanol gave the title compound (0.113 g, 74%); $\delta_H$ (CDCl₃) 1.42 (9H, s), 1.59 (3H, s), 1.63 (3H, s), 3.41 and 3.71 (2H, ABq, J 18 Hz), 3.76 (3H, s), 3.77 (3H, s), 3.78 (3H, s), 3.81 (3H, s), 4.41 (2H, s), 5.06 (1H, d, J 5 Hz), 5.14 (2H, s), 5.21 (2H, s), 5.16 and 5.30 (2H, ABq, J 11.5 Hz), 5.98 (1H, dd, J 9 and 5 Hz), 6.72 (1H, s), 6.80–7.50 (30H, m), 7.94 (2H, d, J 7 Hz), 8.20 (1H, d, J 9 Hz), and 8.86 (2H, d, J 7 Hz); m/z (F.A.B., 3-nitrobenzylalcohol, sodium acetate) MH⁺ 1403.

b) Sodium [6R,7R]-7-[2-(2-amino-4-thiazolyl)- 2-(Z)-(1-carboxy-1-methylethoxyimino)acetamido]-3-[1-1-[ N-(3,4-dihydroxybenzoyl)-N-methylamino]pyridinium- 4-thiomethyl]ceph-3 -em-4-carboxylate.

4-Methoxybenzyl [6R, 7R]-7-[2-(Z)-[ 1-(t-butyloxycarbonyl)-1-methylethoxyimino]-2-( 2-tritylamino-4-thiazolyl)acetamido]-3- [1-[N-[3,4-bis( 4-methoxybenzyl-oxy)benzoyl]-N-methylamino]pyridinium-4-thiomethyl]ceph-3-em-4-carboxylate iodide (0.113 g, 0.08 mmol) was treated with trifluoroacetic acid (6 ml) for 40 minutes, toluene was added, and the mixture evaporated to dryness. The residue was triturated with diethyl ether (2×30 ml) and then dissolved in water and sodium hydrogen carbonate at pH 7.0. The title compound was obtained after purification on Diaion HP20SS resin eluting with mixtures of water and tetrahydrofuran (0.03 g, 49%); $v_{max}$ (KBr) 1764, 1660sh, 1616, and 1532 cm$^{-1}$; $\delta_H$ (D$_2$O) 1.43 (3H, s), 1.45 (3H, s), 3.43 and 3.65 (2H, ABq, J 18 Hz), 3.69 (3H, s), 4.22 and 4.41 (2H, ABq, J 13 Hz), 5.15 (1H, d, J 4.5 Hz), 5.76 (1H, d, J 4.5 Hz), 6.78 (1H, d, J 8 Hz), 6.92 (1H, s), 7.03 (1H, s), 7.05 (1H, d, J 8 Hz), 7.92 (2H, br s), and 8.67 (2H, br s); m/z (F.A.B., thioglycerol, acetic acid) MH$^+$ 765.

EXAMPLE 35

Sodium [6R,7R]-7-[2-(2-amino-4-thiazolyl)-2-(Z)-( 1-carboxy-1-methylethoxyimino) acetamido]-3-[1-(N-benzoyl-N-methylamino)pyridinium- 4-thiomethyl]ceph-3-em-4-carboxylate a) 4-Methoxybenzyl[6R,7R]-3-[1-(N-benzoyl-N-methylamino)pyridinium- 4-thiomethyl]-7-[2-(Z)-[1-(t-butyloxycarbonyl)- 1-methylethoxyimino]-2-(2-tritylamino-4-thiazolyl) acetamido]ceph-3-em-4-carboxylate iodide 4-Methoxybenzyl [6R,7R]-7-[2-(Z)-[ 1-(t-butyloxycarbonyl)-1-methylethoxyimino]-2-(2-tritylamino- 4-thiazolyl)acetamido]-3-(iodomethyl)ceph-3-em-4-carboxylate (0.11 g, 0.12 mmol) in dichloromethane (10 ml) was treated with 1-(N-benzoyl-N-methylamino)-4-thiopyridone (0.03 g, 0.14 mmol) for 1h. The solvent was evaporated under reduced pressure. Purification on silica gel 60 eluting with mixtures of ethyl acetate and ethanol gave the title compound (0.033 g, 25%).

b) Sodium [6R,7R]-7-[2-amino-4-thiazolyl]- 2-(Z)-(1-carboxy-1-methylethoxyimino) acetamido]-3-[ 1-(N-benzoyl-N-methylamino)pyridinium-4-thiomethyl]ceph- 3-em-4-carboxylate 4-Methoxybenzyl [6R,7R]-7-[2-(Z)-[ 1-(t-butyloxycarbonyl)-1-methylethoxyimino]-2-( 2-tritylamino-4-thiazolyl)acetamido]-3-[1-(N-benzoyl N-methylamino)pyridinium-4-thiomethyl]ceph-3-em-4-carboxylate iodide (0.033 g, 0.03 mmol) was treated with trifluoroacetic acid (2 ml) for 0.5h. The mixture was diluted with toluene and the mixture evaporated to dryness. The residue was triturated with diethyl ether (3×15 ml) and then dissolved in water maintained at pH 7 by addition of sodium hydrogen carbonate. Purification on Diaion HP20SS resin eluting with mixtures of water and tetrahydrofuran gave the title compound (0.01 g, 48%); $v_{max}$ (KBr), 1765, 1671, 1617, and 1532 cm$^{-1}$; $\delta_H$ [D$_2$O+ (CD$_3$)$_2$CO] 1.50 (3H, s), 1.52 (3H, s), 3.50 and 3.75 (2H, ABq, J 17.5 Hz), 3.77 (3H, s), 4.36 and 4.50 (2H, ABq, J 14 Hz), 5.21 (1H, d, J 5 Hz), 5.82 (1H, d, J 5 Hz), 6.96 (1H, s), 7.50–7.80 (5H, m), 8.09 (2H, d, J 7 Hz), and 8.84 (2H, d, J 7 Hz).

EXAMPLE 36

[6R, 7R]-7-[2-(2-Amino-4-thiazolyl)-2-(Z)-(methoxyimino) acetamido]-3-[1-(N-benzoyl-N-methylamino)pyridinium-4-thiomethyl]ceph-3-em-4-carboxylate a) 4-Methoxybenzyl [6R,7R]-3-[ 1-(N-benzoyl-N-methylamino)pyridinium-4-thiomethyl]-7-[ 2-(Z)-(methoxyimino)-2-(2-tritylamino-4-thiazolyl)acetamido]ceph- 3-em-4-carboxylate iodide 4-Methoxybenzyl [6R,7R]-3-(iodomethyl)-7-[ 2-(Z)-(methoxyimino)-2-(2-tritylamino-4-thiazolyl)acetamido] ceph- 3-em-4-carboxylate (0.21 g, 0.24 mmol) was dissolved in dichloromethane (15 ml) and treated with 1-(N-benzoyl-N-methyl)- 4-thiopyridone (0.06 g, 0.24 mmol) and stirred for 1.5h. Purification on silica gel 60 eluting with ethyl acetate, ethanol mixtures gave the title compound (0.105 g, 38%).

b) [6R,7R]-7-[2-(2-Amino-4-thiazolyl)- 2-(Z)-(methoxyimino)acetamido]-3-[1-(N-benzoyl-N-methylamino)pyridinium- 4-thiomethyl]ceph-3-em-4-carboxylate 4-Methoxybenzyl [6R,7R]-3-[ 1-(N-benzoyl-N-methylamino)pyridinium-4-thiomethyl]-7-[2-(Z)-(methoxyimino)-2-( 2-tritylamino-4-thiazolyl)acetamido]ceph-3-em-4-carboxylate iodide (0.105 g, 0.09 mmol) in dichloromethane (10 ml) was treated with trifluoroacetic acid (1 ml, 13 mmol) for 1h. The mixture was diluted with toluene and evaporated under reduced pressure. The residue was triturated with diethyl ether (3×20 ml) and dissolved in water maintained at pH 7 by addition of sodium hydrogen carbonate. Purification on Diaion HP20SS resin gave the title compound (0.034 g, 59%); $v_{max}$ (KBr) 1769, 1671, 1616, and 1534 cm$^{-1}$; $\delta_H$ [D20 +(CD$_3$)$_2$CO] 3.43 and 3.68 (2H, ABq, J 17.5 Hz), 3.69 (3H, s), 3.93 (3H, s), 4.24 and 4.43 (2H, ABq, J 14 Hz), 5.14 (1H, d, J 4.5 Hz), 5.74 (1H, d, J 4.5 Hz), 6.95 (1H, s), 7.45–7.70 (5H, m), 7.97 (2H, d, J 7 Hz), and 8.75 (2H, d, J 7 Hz), m/z (F.A.B., thioglycerol) MH$^+$ 640.

EXAMPLE 37

[6R,7R]-7-[2-(2-Amino-4-thiazolyl)- 2-(Z)-(methoxyimino)acetamido]-3-[1-[ N-(3,4-dihydroxycinnamoyl)-N-methylamino]pyridinium-4-thiomethyl]ceph-3-em-4-carboxylate a) 4 -Methoxybenzyl [6R,7R]-3-[1-[N-[ 3,4 -bis(4-methoxybenzyloxy)cinnamoyl]-N-methylamino] pyridinium-4-thiomethyl]-7-[2-(Z)-(methoxyimino)- 2-(2-tritylamino-4-thiazolyl)acetamido]ceph-3-em-4-carboxylate iodide 4-Methoxybenzyl [6R,7R]-3-(iodomethyl)-7-[ 2-(Z)-(methoxyimino)-2-(2-tritylamino-4-thiazolyl)acetamido] ceph- 3-em-4-carboxylate (0.058 g, 0.065 mmol) in dichloromethane (5 ml) was treated with 1-[N-[3,4-bis( 4-methoxybenzyloxy)cinnamoyl]-N-methylamino]-4-thiopyridone (0.035 g, 0.067 mmol) and stirred for 0.5h. Purification on silica gel 60 eluting with ethyl acetate, ethanol mixtures gave the title compound (0.04 g, 44%).

b) [6R,7R]-7-[2-(2-Amino-4-thiazolyl)- 2-(Z)-(methoxyimino)acetamido]-3-[1-N-methylamino] pyridinium-4-thiomethyl]ceph-3-em-4-carboxylate 4-Methoxybenzyl [6R,7R]-3-[1-[N-[3,4-bis( 4-methoxybenzyloxy)cinnamoyl]-N-methylamino]pyridinium- 4-thiomethyl]-7-[2-(Z)-(methoxyimino)-2-(2-tritylamino-4-thiazolyl)acetamido]ceph-3-em-4-carboxylate iodide (0.04 g, 0.03 mmol) in dichloromethane (5 ml) was treated with trifluoroacetic acid (0.3 ml, 3.9 mmol) and stirred for 1h. Toluene was added and the mixture evaporated under reduced pressure. The residue was triturated with diethyl ether (2×20 ml) and dissolved in water maintained at pH 7 by addition of sodium hydrogen carbonate. Purification on Diaion HP20SS resin eluting with water, tetrahydrofuran mixtures gave the title compound (0.002 g, 10%); $\delta_H$ (D$_2$O) 3.45 and 3.73 (2H, ABq, J 18 Hz), 3.74 (3H, s), 3.93 (3H, s), 4.23 and 4.44 (2H, ABq, J 14 Hz), 5.15 (1H, d, J 5 Hz), 5.73 (1H, d, J 5 Hz), 6.70 (1H, d, J 15 Hz), 6.70–7.10 (3H, m), 6.97 (1H, s), 7.65 (1H, d, J 15 Hz), 7.97 (2H, d, J 7 Hz), and 8.60 (2H, d, J 7 Hz).

EXAMPLE 38

[6R,7R]-3-[1-(N-Acetyl-N-methylamino)pyridinium- 4-thiomethyl]-7-[2-(2-amino-4-thiazolyl)- 2-(Z)-(methoxyimino)acetamido]ceph-3-em-4-carboxylate a) 4-Methoxybenzyl [6R,7R]-3-[1-(N-acetyl-N-methylamino)pyridinium- 4-thiomethyl]-7-[2-(Z)-(methoxyimino)- 2-(2-tritylamino-4-thiazolyl)acetamido]ceph-3-em-4-carboxylate iodide 4-Methoxybenzyl [6R,7R]-3-(chloromethyl)-7-[2-(Z)-(methoxyimino)- 2-(2-tritylamino-4-thiazolyl)acetamido] ceph-3-em-4-carboxylate (0.22 g, 0.27 mmol) in dichloromethane (20 ml) was treated with 1-(N-acetyl-N-methylamino)- 4-thiopyridone (0.05 g, 0.27 mmol) and sodium iodide (0.09 g, 0.6 mmol) in acetone (min.vol.) for 6 h. Purification on silica gel 60 eluting with ethyl acetate, ethanol mixtures gave the title compound (0.22 g, 75%).

b) [6R, 7R]-3-[1-(N-Acetyl-N-methylamino)pyridinium- 4-thiomethyl]-7-[2-(2-amino-4-thiazolyl)-2-(Z)-(methoxyimino)acetamido] ceph-3-em-4-carboxylate 4-Methoxybenzyl [6R,7R]-3-[1-(N-acetyl-N-methylamino)pyridinium- 4-thiomethyl]-7-[2-(Z)-(methoxyimino)-2-(2 -tritylamino-4-thiazolyl)acetamido]ceph-3-em-4-carboxylate iodide (0.1 g, 0.09 mmol) in dichloromethane (10 ml) was treated with trifluoroacetic acid (0.5 ml, 6.5 mmol) and stirred for 1 h. The mixture was evaporated to dryness under reduced pressure and the residue triturated with diethyl ether (2×20 ml). The product was dissolved in water maintained at pH 7 by addition of sodium hydrogen carbonate and purified on Diaion HP20SS resin eluting with water, tetrahydrofuran mixtures to give the title compound (0.036 g, 66%); $\upsilon_{max}$ (KBr) 1758, 1671, 1617 and 1533 cm$^{-1}$; δ(D$_2$O) 2.35 (3H, s), 3.45 and 3.73 (2H, ABq, J 18Hz), 3.70 (3H, s), 3.95 (3H, s), 4.21 and 4.44 (2H, ABq, J 14Hz), 5.17 (1H, d, J 4.5Hz), 5.75 (1H, d, J 4.5Hz), 6.98 (1H, s), 7.94 (2H, d, a 7Hz), and 8.52 (2H, d, J 7Hz); m/z (F.A.B., thioglycerol) MH$^+$ 578.

EXAMPLE 39

[6R, 7R]-7-[(2-Amino-4-thiazolyl)-2-(Z)-(methoxyimino)acetamido] -3-[1-[N-methyl-N-(4-nitrobenzoyl)amino] pyridinium-4-thiomethyl]ceph-3-em-4-carboxylate a) 4-Methoxybenzyl [6R, 7R]-7-[2(Z)-(methoxyimino)- 2-(2-tritylamino-4-thiazolyl)acetamido]-3-[1-[N-methyl-N-( 4-nitrobenzoyl)amino]pyridinium-4-thiomethyl] ceph-3-em-4-carboxylate iodide A mixture of 4-methoxybenzyl [6R,7R]-3-(chloromethyl)- 7-[2-(Z)-(methoxyimino)-2-(2-tritylamino-4-thiazolyl)acetamido] ceph-3-em-4-carboxylate (0.20 g, 0.25 mmol) and 1-[N-methyl-N-(4-nitrobenzoyl)amino]-4-thiopyridone (0.073 g, 0.25 mmol) in dichloromethane (10 ml) was treated with sodium iodide (0.076 g, 0.5 mmol) in a little acetone. After 0.25 h diethyl ether (50 ml) was added and the precipitate was then filtered off and washed, first with ether, then with water. The residue was dried in vacuum to give off the title compound (0.26 g, 86%); δH (CDCl$_3$+D$_2$O) 3.53 and 3.90 (2H, ABq, J 16Hz), overlaying 3.75 (3H, s) and 3.00 (3H, s), 4.01 (3H, s), 4.39 and 4.55 (2H, ABq, J 12Hz), 5.12 (1H, d, J 4Hz) overlaying 5.15 and 5.25 (2H, ABq, J 12Hz), 5.87 (1H, d, J 4Hz), 6.55 (1H, s), 6.87 (2H, d, J 9Hz), 7.1– 7.4 (17H, m), 7.9 (2H, d, J 7Hz), 8.13 (2H, d, J 8Hz), 8.30 (2H, d, J 8 Hz), and 9.07 (2H, d, J 7 Hz).

b) [6R, 7R]-7-[(2-Amino-4-thiazolyl)-2-(Z)-(methoxyimino)acetamido] -3-[1-[N-methyl-N-(4-nitrobenzoyl)amino] pyridinium-4-thiomethyl]ceph-3-em-4-carboxylate The product of Example 39(a) (0.20 g, 0.16 mmol) was dissolved in 5% trifluoroacetic acid in dichloromethane (10 ml) for 0.75 h. The mixture was evaporated under reduced pressure and the residue was extracted with water neutralising to pH 7 with sodium hydrogen carbonate. The aqueous extracts were purified on Dialon HP20SS resin, eluting with mixtures of water and tetrahydrofuran. Fractions containing product were combined and freeze-dried to give the title compound (0.053 g, 46%); $\upsilon_{max}$ (KBr) 1769, 1676, and 1617 cm$^{-1}$; δH [D$_2$O+(CD$_3$)$_2$CO] 3.63 (3H, s), 4.04 (3H, s), 4.46 and 4.47 (2H, ABq, J 14Hz), 5.25 (1H, d, J 5Hz), 5.86 (1H, d, J 5Hz), 6.97 (1H, s), 8.05 (2H, d, J 7Hz), 8.24 (2H, d, J 7Hz), 8.46 (2H, d, J 8Hz), and 8.96 (2H, d, J 7Hz); m/z (F.A.B., thioglycerol) MH$^+$ 685.

EXAMPLE 40

[6R, 7R]-7-[(2-Amino-4-thiazolyl)-2-(Z)-(methoxyimino)acetamido] -3-[1-(N-(4-methoxybenzoyl)-N-methylamino]-pyridinium- 4-thiomethyl] ceph-3-em-4-carboxylate a) 4-Methoxybenzyl [6R, 7R]-3-[1-[N-(4-methoxybenzoyl)-N-methylamino] pyridinium-4-thiomethyl]-7-[2 -(Z)-(methoxyimino)-2-(2-tritylamino-4-thiazolyl)- acetamido] ceph-3-em-4-carboxylate iodide A mixture of 4-methoxybenzyl [6R,7R]-3-(chloromethyl)- 7-[2-(Z)-(methoxyimino)-2-(2-tritylamino-4-thiazolyl)acetamido] ceph-3-em-4-carboxylate (0.107 g, 0.13 mmol) and 1-[N-(4-methoxybenzoyl)-N-methylamino]-4-thiopyridone (0.074 g, 0.26 mmol) in acetonitrile (15 ml) was treated with sodium iodide (0.02 g, 0.13 mmol) in a little acetone. The mixture was stirred for 1 h, then purified on silica gel 60 eluting with mixtures of dichloromethane and methanol to give the title compound (0.121 g, 84%); δH (CDCl$_3$) 3.53 and 3.81 (2H, ABq, J 8Hz), 3.73 (3H, s), 3.86 (3H, s), 3.90 (3H, s), 4.06 (3H, s), 4.45 and 4.55 (2H, ABq, J 12Hz), 5.11 (1H, d, J 4Hz), 5.18 and 5.28 (2H, ABq, J 12Hz), 5.91 (1H, dd, J 4 and 9Hz), 6.70 (1H, s), 6.88 (2H, d, J 9Hz), 7.00 (2H, d, J 9Hz), 7.26–7.33 (15H, m), 7.35 (2H, d, J 9Hz) 7.79 (2H, d, J 9Hz), 7.95 (2H, d, J 7Hz), and 7.79 (2H, d, J 7Hz); m/z (F.A.B., thioglycerol) MH$^+$ 1032.

b) [6R,7R]-7-[2-(2-Amino-4-thiazolyl)-2-(Z)-(methoxyimino)acetamido] -3-[1-[N-(4-methoxybenzoyl)-N-methylamino]D pyridinium-4-thiomethyl]ceph-3-em-4 -carboxylate The product of Example 40(a) (0.11 g, 0.095 mmol) was dissolved in 5% trifluoroacetic acid in dichloromethane (10 ml) for 1 h and was then evaporated under reduced pressure. The residue was extracted with water neutralising to pH 7.0 with sodium hydrogen carbonate and the extracts were purified on Diaion HP20SS resin, eluting with mixtures of water and tetrahydrofuran. Fractions containing product were combined and freeze-dried to give the title compound (0.044 g, 62%); $\upsilon_{max}$ (KBr) 1762, 1672, and 1616 cm$^{-1}$; $\delta[D_2O+(CD_3)_2CO]$ 3.52 and 3.76 (2H, ABq, J 18Hz), 3.84 (3H, s), 3.93 (3H, s), 3.99 (3H, s), 4.54 and 4.60 (2H, ABq, J 14Hz), 5.22 (1H, d, J 4Hz), 5.84 (1H, d, J 4Hz), 6.9 (1H, s), 7.12 (2H, d, J 9Hz), 7.77 (2H, d, J 9Hz), 8.25 (2H, d, J 7Hz), and 8.94 (2H, d, J 7Hz); m/z (F.A.B., thioglycerol) MH$^+$ 670.

EXAMPLE 41

[6R, 7R]-7-[2-(2-Amino-4-thiazolyl)-2-(Z)-(methoxyimino)acetamido]
-3-[1-[N-(2-furoyl)-N-methylamino]
pyridinium-4-thiomethyl]ceph-3-em-4-carboxylate a) 4-Methoxybenzyl [6R,
7R]-3-[1-[N-(2-furoyl)-N-methylamino]
pyridinium-4-thiomethyl]-7-[2-(Z)-(methoxyimino)-
2-(2-tritylamino-4-thiazolyl)acetamido]ceph-3
-em-4-carboxylate iodide A mixture of 4-methoxybenzyl [6R,7R]-3-(chloromethyl)- 7-[2-(Z)-(methoxyimino)-2-(2-tritylamino-4-thiazolyl)acetamido] ceph-3-em-4-carboxylate (0.185 g, 0.23 mmol) and 1-[N-(2-furoyl)-N-methylamino]-4-thiopyridone (0.055 g, 0.23 mmol) in acetonitrile (10 ml) was treated with sodium iodide (0.035 g, 0.23 mmol) dissolved in a little acetone. The mixture was then purified on silica gel 60 eluting with mixtures of dichloromethane and methanol to give the title compound (0.113 g, 61%) $\upsilon_{max}$ (KBr) 1777, 1719, 1671, and 1612 cm$^{-1}$; $\delta$H (CDCl$_3$+ D$_2$O) 3.60 and 3.89 (2H, ABq, J 21Hz), 3.78 (3H, s), 4.04 (3H, s), 4.06 (3H, s), 4.58 (2H, br s), 5.14 (1H, d, J 5Hz), 5.19 and 5.28 (2H, ABq, J 12Hz), 6.93 (1H, d, J 5Hz), 6.59 (1H, dd, J 1.5 and 3.5Hz), 6.7 (1H, s), 6.87 (2H, d, J 9Hz), 7.25–7.4 (15H, m) overlaying 7.36 (2H, d, J 9Hz), 7.39 (1H, d, J 3.5Hz), 7.60 (1H, d, J 3.5Hz), 8.04 (2H, d, J 7Hz), and 8.57 (2H, d, J 7Hz); m/z (F.A.B. thioglycerol) M$^+$ 992.

b) [6R, 7R]-7-[2-(2-Amino-4-thiazolyl)-2-(Z)-
(methoxyimino)acetamido]
-3-[1-[N-(2-furoyl)-N-methylamino]
pyridinium-4-thiomethyl]ceph-3-em-4-carboxylate The product of Example 41(a) (0.105 g, 0.13 mmol) was dissolved in 5% trifluoroacetic acid in dichloromethane (20 ml) for 0.75 h. The mixture was evaporated and the residue was washed with diethyl ether and then extracted with water, neutralising to pH 7 with sodium hydrogen carbonate. The aqueous extracts were purified on Diaion HP20SS resin eluting with water, tetrahydrofuran mixtures. Fractions containing the product were combined and freeze-dried to give the title compound (0.067 g, 100%); $\upsilon_{max}$ (KBr) 1777, 1719, 1671, and 1612 cm$^{-1}$; $\delta_H$ [D$_2$O+(CD$_3$)$_2$CO] 3.67 and 3.91 (2H, ABq, J 17 Hz), 4.07 (3H, s), 4.13 (3H, s), 4.56 and 4.67 (2H, d, J 12 Hz), 5.36 (1H, d, J 5 Hz), 5.95 (1H, d, J 5 Hz), 6.84 (1H, dd, J 1.5 and 3.5 Hz), 7.05 (1H, s), and 7.45 (1H, d, J 7 Hz).

EXAMPLE 42

[6R,
7R]-7-[2-(2-Amino-4-thiazolyl)-2-(Z)-(methoxyimino)
acetamido]-3-(1-ureidopyridinium-4-thiomethyl)ceph-3
-em-4-carboxylate a) 4-Methoxybenzyl [6R,
7R]-7-[2-(Z)-(methoxyimino)-
2-(2-tritylamino-4-thiazolyl)acetamido]-3-[1-
ureidopyridinium-
4-thiomethyl]ceph-3-em-4-carboxylate iodide 4-Methoxybenzyl [6R, 7R]-3-(chloromethyl)-7-[2-(Z)-(methoxyimino)- 2-(2-tritylamino-4-thiazolyl)acetamido] -ceph-3-em-4-carboxylate (0.505 g, 0.63 mmol) in acetonitrile (5 ml) was treated with 1-ureido-4-thiopyridone (0.10 g, 0.63 mmol) and sodium iodide (0.10 g, 0.67 mmol) in N,N-dimethylformamide (2 ml) for 2 h. The mixture was added to diethyl ether (50 ml) then the precipitate was filtered off, washed with ether then water and finally dried in vacuo to give the title compound (0.51 g, $\upsilon_{max}$ (KBr) 1780, 1720, 1660, and 1620 cm$^{-1}$; $\delta_H$ [(CD$_3$)$_2$SO] 3.72 (3H, s), 3.80 (3H, s), 4.36 (2H, brs), 5.21 (3H, m), 5.66 (1H, dd, J 8 Hz and 2 Hz), 6.71 (1H, s), 6.87 (2H, d, J 8 Hz), 7.04 (2H, s), 7.34 (17H, m), 7.94 (2H, d, J 7 Hz), 8.77 (2H, d, J 7 Hz), 8.87 (1H, s) and 9.60 (1H, d, J 8 Hz), m/z (F.A.B., 3-nitrobenzyl alcohol, sodium acetate) MHNa$^+$ 950.

b) [6R, 7R]-[2,
(2-Amino-4-thiazolyl)-2-(Z)-(methoxyimino)acetamido]
-3-(1-ureidopyridinium-4-thiomethyl)-ceph-
3-em-4-carboxylate The product of Example 42(a) was treated as in Example 41(b) to give the title compound (43%); $\upsilon_{max}$ (KBr) 1760, 1660, and 1615 cm$^{-1}$; $\delta_H$ (D$_2$O) 3.43 and 3.72 (2H, ABq, J 17.5 Hz), 3.95 (3H, s), 4.04 and 4.39 (2H, ABq, J 13.5 Hz), 5.14 (1H, d, J 4.5 Hz), 5.74 (1H, d, J 4.5 Hz), 7.00 (1H, s), 7.64 (2H, d, J 7 Hz), and 8.14 (2H, d, J 7 Hz); m/z (F.A.B., thioglycerol) MH$^+$ 579.

EXAMPLE 43

[6R, 7R]-7-[2-(2-Amino-4-thiazolyl]-2-(Z)-
(methoxyimino)acetamido]
-3-1-(1,3-dimethylureido)pyridinium-4-thiomethyl]
ceph-3-em-4-carboxylate a) 4-Methoxybenzyl
[6R,7R]-3-[1-(1,3-dimethylureido)pyridinium-
4-thiomethyl]-7-[2-(Z)-(methoxyimino)-
2-(2-tritylamino-4-thiazoyl)acetamido]ceph-3
-em-4-carboxylate iodide To a solution of 4-methoxybenzyl [6R,7R]-3-(chloromethyl)- 7-[2-(Z)-(methoxyimino)-2-(2-tritylamino-4 -thiazolyl)acetamido]ceph-3-em-4-carboxylate (0.20 g, 0.25 mmol) in acetonitrile (3 ml) was added a solution of 1-(1, 3-dimethylureido)-4-thiopyridone (0.060 g, 0.30 mmol) and sodium iodide (0.038 g, 0.25 mmol) in acetonitrile (2.5 ml) and acetone (2.5 ml). After 2 h the reaction mixture was poured into diethyl ether (50 ml) and the precipitate was filtered off, washed with ether and water and then dried in vacuo. The title compound was obtained as a yellow solid (0.163 g, 58%), $\upsilon_{max}$ (KBr), 1780, 1685(b), and 1615 cm$^{-1}$; $\delta_H$ [(CD$_3$)$_2$SO] 2.68 (3H, d, J 4 Hz), 3.49 (3H, s), 3.73 (3H, s), 3.80 (3H, s), overlaying 3.51 and 3.77 (2H, ABq, J 13

Hz), 4.37 (2H, brs), 5.20 (1H, d, J 5 Hz), 5.21 (2H, s), 5.72 (1H, dd, J 5, 8 Hz), 6.71 (1H, s), 6.88 (2H, d, J 8 Hz), 7.23–7.42 (17H, m), 8.07 (2H, d, J 7 Hz), 8.87 (1H, s), 8.99 (2H, d, J 7 Hz), and 9.59 (1H, d, J 8 Hz); m/z (F.A.B., thioglycerol) M$^+$ 955.

b) [6R, 7R ]-7-[2-(2-Amino-4-thiazolyl)-2-(Z)-(methoxyimino)acetamido] -3-[1-(1,3-dimethylureido)pyridinium-4-thiomethyl]ceph-3-em-4-carboxylate The product of Example 43(a) was treated as in Example 41(b) to give the title compound (55%); $\upsilon_{max}$ (KBr) 1765, 1670, and 1615 cm$^{-1}$; $\delta_H$ (D$_2$O) 2.83 (3H, s), 3.56 and 3.84 (2H, ABq, J 18 Hz), 3.60 (3H, s), 4.06 (3H, s), 4.32 and 4.54 (2H, ABq, J 14 Hz), 5.28 (1H, d, J 5 Hz), 5.86 (1H, d, J 5 Hz), 7.09 (1H, s), 8.03 (2H, d, J 7 Hz), and 8.68 (2H, J 7 Hz); m/z (F.A.B., thioglycerol) MH$^+$ 593.

EXAMPLE 44

[6R, 7R]-7-[2-(2-Amino-4-thiazolyl)-2-(Z)-(methoxyimino)acetamido] -3-[1-(1-methylureido)pyridinium-4 -thiomethyl]ceph-3-em-4-carboxylate a) 4-Methoxybenzyl [6R, 7R]-7-[2-(Z)-(methoxyimino)-2-(2-tritylamino-4-thiazolyl)acetamido]-3-[1 -(1-methylureido)pyridinium-4-thiomethyl]ceph-3-em-4 -carboxylate iodide A mixture of 4-methoxybenzyl [6R,7R]-3-(chloromethyl)- 7-[2-(Z)-(methoxyimino)-2-(2-tritylamino-4-thiazolyl)acetamido] ceph-3-em-4-carboxylate (0.015 g, 0.19 mmol), 1-(methylureido)-4-thiopyridone (0.028 g, 0.15 mmol) and sodium iodide (0.028 g, 0.19 mmol) in acetonitrile (5 ml) was stirred for 2 h then poured into diethyl ether (40 ml). The precipitate was filtered off, washed with ether and water, then dried in vacuo. The title compound was obtained as a pale yellow solid (0.105 g, 64%); $\upsilon_{max}$ (KBr) 1780, 1705, 1695, and 1615 cm$^{-1}$; $\delta_H$ [(CD$_3$)$_2$SO] 3.50 (3H, s), 3.55 (3H, s), 3.51 and 3.56 (2H, ABq, 18 Hz), 3.80 (3H, s), 4.37 (2H, brs), 5.20 (1H, d, J Hz), 5.21 (2H, s), 5.71 (1H, dd, J 5, 8 Hz), 6.65 (1H, s), 6.88 (2H, d, J 8 Hz), 7.14 (2H, s), 7.23–7.36 (15H, m), 8.05 (2H, d, J 7 Hz), 8.80 (1H, s), 8.96 (2H, d, J 7 Hz), and 9.54 (1H, d, J 8 Hz); m/z (F.A.B., thioglycerol) M$^+$ 941.

b) [6R, 7R]-7-[2-(2-Amino-4-thiazolyl)-2-(Z)-(methoxyimino)acetamido] -3-[1-(1-methylureido)pyridinium-4-thiomethyl]ceph-3-em-4-carboxylate The product of Example 44(a) was treated as in Example 41(b) to give the title compound (44%); $\upsilon_{max}$ (KBr) 1765, 1670, and 1615 cm$^{-1}$; $\delta_H$ (D$_2$O) 3.52 (3H, s), 3.44 and 3.72 (2H, ABq, J 17 Hz), 3.94 (3H, s), 4.18 and 4.43 (2H, ABq, J 14 Hz), 5.16 (1H, d, J 5 Hz), 5.75 (1H, d, J 5 Hz), 6.97 (1H, s), 7.90 (2H, d, J 7 Hz), and 8.61 (2H, d, J 7 Hz); m/z (F.A.B., thioglycerol) MH$^+$ 579.

EXAMPLE 45

[6R,7R]-7-[2-(2-Amino-4-thiazolyl)-2-(Z)-(methoxyimino)acetamido] -3-[1-(2-oxopyrrolidin-1-yl)pyridinium-4-thiomethyl]ceph-3-em-4-carboxylate a) 4-Methoxybenzyl [6R, 7R]-7-[2-(Z)-(methoxyimino)-2-(2-tritylamino-4-thiazolyl)acetamido]-3-[1 -(2-oxopyrrolidin-1-yl) pyridinium-4-thiomethyl]ceph-3 -em-4-carboxylate iodide 4-Methoxybenzyl [6R,7R]-3-(chloromethyl)-7-[2-(Z)-(methoxyimino)- 2-(2-tritylamino-4-thiazolyl)acetamido] -ceph-3-em-4-carboxylate (0.1 g, 0.13 mmol) was dissolved in acetonitrile (2 ml) and treated with 1-(2-oxopyrrolidin-1-yl)-4-thiopyridone (0.0244 g, 0.13 mmol) then sodium iodide (0.0189 g, 0.13 mmol). After 1 h, the reaction mixture was purified on silica gel 60, eluting with dichloromethane, ethyl acetate and finally mixtures of methanol in dichloromethane, to give the title compound (0.102 g, 76%); $\upsilon_{max}$ (KBr) 1781, 1725, 1677 and 1616 cm$^{-1}$; $\delta_H$ (CDCl$_3$) 2.39 (2H, t, J 7 Hz), 2.73 (2H, t, J 7 Hz), 2.89 and 3.33 (2H, ABq, J 18 Hz), 3.80 (3H, s), 4.06 (3H, s), 4.32 (2H, t, J 7 Hz), 4.34 and 4.64 (2H, ABq, J 12 Hz), 5.10 (1H, d, J 5 Hz), 5.26 and 5.40 (2H, ABq, J 12 Hz), 5.91 (1H, dd, J 5 and 9 Hz), 6.72 (1H, brs), 6.97 (2H, d, J 9 Hz), 7.22–7.40 (17H, m), 7.94 (2H, d, J 7Hz), and 8.86 (2H, d, J 7 Hz); m/z (F.A.B., thioglycerol), M$^+$ 952.

b) [6R,7R]-7-[2-(2-Amino-4-thiazolyl)-2-(Z)-(methoxyimino)acetamido] -3-[1-(2oxopyrrolidin-1-yl)pyridinium-4-thiomethyl]ceph-3-em-4-carboxylate The product of Example 45(a) (0.1 g, 0.093 mmol) was suspended in dry dichloromethane (5 ml) and treated with trifluoroacetic acid (0.317 g, 2.8 mmol). After 40 minutes, the volatiles were removed under reduced pressure and the residue suspended in water (10 ml) and acetone (5 ml). The pH was adjusted to 7.5 with saturated aqueous sodium hydrogen carbonate and the mixture washed with ethyl acetate and diethyl ether before being concentrated under reduced pressure and freeze-dried. Purification of the freeze-dried material on Diaion HP20SS resin, eluting with mixtures of tetrahydrofuran in water, gave the title compound (0.02 g, 37%); $\upsilon_{max}$ (KBr) 1761, 1670 and 1617 cm$^{-1}$; $\delta_H$ (D$_2$O) 2.21–2.37 (2H, m), 2.64 (2H, t, J 8 Hz), 3.43 and 3.71 (2H, ABq, J 18 Hz), 3.93 (3H, s), 4.04 (2H, t, J 8 Hz), 4.20 and 4.43 (2H, ABq, J 14 Hz), 5.15 (1H, d, J 5 Hz), 5.74 (1H, d, J 5 Hz), 6.95 (1H, s), 7.94 (2H, d, J 7 Hz), and 8.54 (2H, d, J 7 Hz); m/z (F.A.B., thioglycerol). MH$^+$ 590.

EXAMPLE 46

[6R, 7R]-7-[2-Amino-4-thiazolyl)-2-(Z)-(methoxyimino)acetamido] -3-[1-(2-oxopiperidin-1-yl)pyridinium-4-thiomethyl]ceph-3-em-4-carboxylate a) 4-Methoxybenzyl [6R, 7R]-7-[2-(Z)-(methoxyimino)-2-(2-tritylamino-4-thiazolyl)acetamido]-3-[1 -(2-oxopiperidin-1-yl)pyridinium-4-thiomethyl]ceph-3 -em-4-carboxylate iodide 4-Methoxybenzyl [6R,7R]-3-(chloromethyl)-7-[2-(Z)-(methoxyimino)- 2-(2-tritylamino-4-thiazolyl)acetamido] ceph-3-em-4-carboxylate (0.1 g, 0.13 mmol) was reacted with 1-(2-oxopiperidin-1-yl)-4-thiopyridone (0.0244 g, 0.13 mmol) and sodium iodide (0.127 g, 0.1 mmol) in acetonitrile (5 ml) as described in Example 45(a). The product was obtained as a yellow foam after purification on silica gel 60, eluting with dichloromethane, ethyl acetate and finally mixtures of methanol in dichloromethane (0.078 g, 56%); $\upsilon_{max}$ (CH$_2$Cl$_2$) 1780, 1680 and 1610 cm$^{-1}$; $\delta_H$ (CDCl$_3$) 1.80–2.20 (4H, m), 2.35–2.75 (2H, m), 2.90–3.30 (2H, m), 3.50–4.20 (8H, m), 4.30–4.65 (2H, m), 4.90–5.30 (3H, m), 5.70–5.95 (1H, m), 6.43 (1H, s), 6.70–7.40 (19H, m), 7.80–8.10 (2H, m), and 8.70–9.15 (2H, m); m/z (F.A.B., thioglycerol) MH$^+$ 966.

b) [6R,7R]-7-[2-(2-Amino-4-thiazolyl)-2-(Z)-(methoxyimino)-acetamido] -3-[1-(2-oxopiperidin-1-yl)pyridinium-4-thiomethyl]ceph-3-em-4-carboxylate The product of Example 46(a) (0.078 g, 0.07 mmol) was deprotected with trifluoroacetic acid (0.488 g, 4.3 mmol) in dichloromethane (5 ml) as described in Example 45(b). Chromatography of the crude product on Diaion HP20SS resin, eluting with mixtures of tetrahydrofuran and water, gave the title product (0.022 g, 51%); $\upsilon_{max}$ (KBr) 1762, 1670 and 1617 cm$^{-1}$; $\delta_H$ [D$_2$O+(CD$_3$)$_2$CO] 1.81–1.98 (2H, m), 1.98–2.15 (2H, m), 2.61 (2H, t, J 6 Hz), 3.41 and 3.69 (2H, ABq, J 19 Hz), 3.87–4.04 (5H, m), 4.20 and 4.41 (2H, ABq, J 14 Hz), 5.14 (1H, d, J 5 Hz), 5.72 (1H, d, J 5 Hz), 6.93 (1H, s), 7.94 (2H, d, J 7 Hz), and 8.55 (1H, d, J 7 Hz).

EXAMPLE 47

[6R, 7R]-7-[2-(2-Amino-4-thiazolyl)-2-(Z)-(methoxyimino)acetamido] -3-[1-[N-(4-carboxybenzoyl)-N-methylamino] pyridinium-4-thiomethyl]ceph-3-em-4-carboxylate sodium salt a) 4-Methoxybenzyl [6R, 7R]-3-[1-(N-(4 -diphenylmethoxycarbonylbenzoyl)-N-methylamino]-pyridinium-4 -thiomethyl]-7-[2-(Z)-(methoxyimino)-2-(2-tritylamino-4-thiazolyl)acetamido]ceph-3-em-4-carboxylate iodide and chloride 4-Methoxybenzyl [6R, 7R]-3-(chloromethyl)-7-[2-(Z)-(methoxyimino)- 2-(2-tritylamino-4-thiazolyl)acetamido] -ceph-3-em-4-carboxylate (0.158 g, 0.2 mmol), 1-[e,uns N-(4 -diphenylmethoxycarbonylbenzoyl)-N-methylamino]-4-thiopyridone (0.098 g, 0.2 mmol) and sodium iodide (0.03 g, 0.2 mmol) in acetonitrile (5 ml) and N,N-dimethylformamide (5 ml) were stirred for 1 h. The volatiles were removed under reduced pressure and the residue redissolved in dichloromethane (25 ml). This solution was washed (5x) with water, saturated brine, dried and evaporated to dryness under reduced pressure. Purification on silica gel 60, eluting with dichloromethane, ethyl acetate then methanol in dichloromethane (1:19) gave the iodide (0.0922 g, 34%); $\upsilon_{max}$ (KBr) 1781, 1719, 1669 and 1612 cm$^{-1}$; $\delta_H$ (CDCl$_3$) 3.51 (1H, d, J 19 Hz), 3.79 (3H, s), 3.88 (3H, s), 4.06 (3H, s), 4.40 and 4.53 (2H, ABq, J 13 Hz), 5.12 (1H, d, J 5 Hz), 5.20 and 5.28 (2H, ABq, J 12 Hz), 5.93 (1H, dd, J 5 and 9 Hz), 6.70 (1H, s), 6.88 (2H, d, J 8 Hz), 7.03 (1H, brs, exchangeable), 7.13 (1H, s), 7.17–7.50 (27H, m), 7.90 (2H, d, J 7 Hz), 7.98 (2H, d, J 7 Hz), 8.01 (1H, d, J 9 Hz), 8.28 (2H, d, J 7 Hz), and 9.00 (2H, d, J 7 Hz); m/z (F.A.B., thioglycerol) M$^+$ 1212.

Further elution gave the chloride (0.0614 g, 25%); m/z (F.A.B., thioglycerol) M$^+$ 1212. The chloride could be converted to the iodide with sodium iodide in acetone.

b) [6R, 7R]-7-[2-(2-Amino-4-thiazolyl)-2-(Z)-(methoxy-imino)acetamido] -3-[1-[N-(4-carboxybenzoyl)-N-methylamino] pyridinium-4-thiomethyl]ceph-3-em-4 -carboxylate sodium salt The products of Example 47(a), iodide (0.0922 g, 0.069 mmol) and chloride (0.0614 g, 0.049 mmol) were combined and deprotected as described in Example 45(b) and the title compound obtained after purification on Diaion HP20SS resin (0.042 g, 50%); $\upsilon_{max}$ (KBr) 1759, 1670 and 1617 cm$^{-1}$; $\delta_H$ (D$_2$O) 3.42 (1H, d, J 18 Hz), 3.69 (3H, s), 3.94 (3H, s), 4.24 and 4.40 (2H, ABq, J 13 Hz), 5.17 (1H, d, J 5 Hz), 5.75 (1H, d, J 5 Hz), 6.96 (1H, s), 7.68 (2H, d, J 8 Hz), 7.86–8.07 (4H, m), and 8.73 (2H, d, J 7 Hz).

EXAMPLE 48

[6R, 7R], 3-[1-[N-(4-Aminobenzoyl)-N-methylamino]pyridinium- 4-thiomethyl]-7-[2-(2-amino-4-thiazolyl)-2-(Z)-(methoxyimino)acetamido] ceph-3-em-4-carboxylate a) 4-Methoxybenzyl [6R, 7R]-3-[1-[N-[4-(t-butoxycarbonylamino)benzoyl] -N-methylamino]pyridinium-4-thiomethyl] -7-[2-(Z)-(methoxyimino)-2-(2-tritylamino-4 -thiazolyl)acetamido]ceph-3-em-4-carboxylate iodide The title compound was prepared from 4-methoxybenzyl [6R,7R]-3-(chloromethyl)-7-[2-(Z)-(methoxyimino)-2-(2 -tritylamino-4-thiazolyl)acetamido]ceph-3-em-4-carboxylate (0.198 g, 0.25 mmol), 1-[N-(4-(t-butoxycarbonylamino)benzoyl] -N-methylamino]-4-thiopyridone (0.09 g, 0.25 mmol) and sodium iodide (0.038 g, 0.25 mmol) in acetonitrile (10 ml) as described in Example 45 (a) (0.21 g, 67%); $\upsilon_{max}$ (KBr) 1785, 1719, 1677 and 1612 cm$^{-1}$; $\delta_H$ (CD$_3$OD) 1.53 (9H, s), 3.74 (3H, s), 3.76 (3H, s), 3.95 (3H, s), 5.17 (1H, d, J 5 Hz), 5.24 (2H, brs), 5.79 (1H, d, J 5 Hz), 6.77 (1H, s), 6.86 (2H, d, J 9 Hz), 7.23–7.41 (17H, m), 7.60 (2H, d, J 9 Hz), 7.70 (2H, d, J 9 Hz), 8.00 (2H, d, J 7 Hz), and 8.88 (2H, d J 7 Hz); m/z (F.A.B., thioglycerol) M$^+$ 1117.

b) [6R, 7R]-3-[1-[N-(4-Aminobenzoyl)-N-methylamino] pyridinium-4-thiomethyl]-7-[2-(2-amino-4-thiazolyl)-2 -(Z)-(methoxyimino)acetamido]Ceph-3-em-4-carboxylate The product of Example 48(a) (0.2 g, 0.16 mmol) was treated with trifluoroacetic acid (2 ml) for 10 minutes then diluted with toluene and evaporated to dryness under reduced pressure. The residue was triturated with ether and then dissolved in water containing sodium hydrogen carbonate to pH 7.0. Purification on Diaion HP20SS resin eluting with tetrahydrofuran water mixtures gave the title compound (0.037 g, 35%); $\upsilon_{max}$ (KBr) 1761, 1669 and 1605 cm$^{-1}$; $\delta_H$ [D$_2$O+(CD$_3$)$_2$CO] 3.51 and 3.75 (2H, ABq, J 17Hz), 3.81 (3H, s), 4.01 (3H, s), 4.35 and 4.51 (2H, ABq, J 13 Hz), 5.21 (1H, d, J 5 Hz), 5.82 (1H, d, J 5 Hz), 6.83 (2H, d, J 8 Hz), 6.99 (1H, s), 7.54 (2H, d, J 8 Hz), 8.09 (2H, d, J 7 Hz), and 8.81 (2H, d, J 7 Hz).

EXAMPLE 49

Sodium [6R,7R]-7-[2-(2-amino-4-thiazolyl)-2-(Z)-[(S)-carboxy (3,4-dihydroxyphenyl)methyloxyimino] acetamido]-3-[1-(methylamino)pyridinium-4-thiomethyl]-ceph-3-em-4-carboxylate a) 4-Methoxybenzyl [6R,7R]-7-[(Z)-[(S)-(3,4-diacetoxyphenyl)(diphenylmethyloxycarbonyl)-methyloxyimino]-2-(2-tritylamino-4-thiazolyl)acetamido]-3-[1-(methylamino(pyridinium-4-thiomethyl]ceph-3-em-4-carboxylate iodide.

2-[(Z)-[S]-(3,4-Diacetoxyphenyl)(diphenylmethyloxycarbonyl)methyloxyimino] -2-(2-tritylamino-4-thiazolyl)acetic acid (0.845 g, 1 mmol) was dissolved in dry N,N-dimethylformamide (5 ml) under argon and cooled to 0°–5° C. N,N-Diisopropylethylamine (0.129 g, 1 mmol) was added and the mixture cooled to –40° C. Methanesulphonyl chloride (0.114 g, 1 mmol) was added and the mixture allowed to warm to –20° C. and stirred at –20° C. for 0.5 h. The reaction mixture was re-cooled to –40° C. and treated with a solution of 4-methoxybenzyl [6R,7R]-7-amino-3-[1-(methylamino)pyridinium-4-thiomethyl]ceph-3-em-4-carboxylate iodide (0.6 g, 1 mmol) and pyridine (0.079 g, 1 mmol) in dry dichloromethane (10 ml). Cooling was removed and the mixture allowed to regain room temperature. After 1 h, the reaction mixture was diluted with dichloromethane (50 ml) and washed with water (5×20 ml), saturated brine, dried over magnesium sulphate and evaporated to dryness under reduced pressure. The residue was dissolved in acetone (10 ml) and treated with sodium iodide (0.15 g, 1 mmol). After 0.5 h, the reaction mixture was filtered through Celite and evaporated to dryness under reduced pressure. The residue was purified on silica gel 60, eluting with methanol, dichloromethane mixtures, to give the title compound (0.271 g, 19%); $\upsilon_{max}$ (KBr) 1774, 1730, 1670 and 1616 cm$^{-1}$; $\delta_H$ [(CD$_3$)$_2$SO] 2.23–2.28 (6H, br), 3.00 (3H, d, J 6Hz), 3.71 (3H, s), 4.27 (2H, br s), 5.12 (1H, d, J 5Hz), 5.20 (2H, br s), 5.55 (1H, dd, J 8 and 5Hz), 5.87 (1H, s), 6.78–6.89 (4H, m), 7.14–7.48 (30H, m), 7.88 (2H, d, J 7Hz), 8.11–8.20 (1H, q, J 6Hz, exch.), 8.76 (2H, d, J 7Hz), 8.96 (1H, br s, exch.), 9.62 (1H, d, J 8Hz, exch.); m/z (F.A.B., thioglycerol) MH$^+$ 1300.

b) Sodium [6R,7R]-7-[2-(2-amino-4-thiazolyl)-2-(Z)-[(S)-carboxy(3,4-dihydroxyphenyl)methyloxyimino] acetamido]-3-[1-(methyamino)pyridinium-4-thiomethyl]-ceph-3-em-4-carboxylate 4-Methoxybenzyl [6R,7R]-7-[2-(Z)-[(S)-(3,4-diacetoxyphenyl)(diphenylmethyloxycarbonyl)-methyloxyimino]-2-(2-tritylamino-4-thiazolyl)acetamido]-3-[1-(methylamino)pyridinium-4-thiomethyl]ceph-3-em-4-carboxylate iodide (0.25 g, 0.18 mmol) was dissolved in dichloromethane (15 ml) and treated with trifluoroacetic acid (0.906 g, 7.9 mmol). After 1 h, the volatiles were removed under reduced pressure, the residue treated with toluene (2 ml) and re-evaporated to dryness under reduced pressure. The residue was triturated under diethyl ether and the resulting solid collected by filtration and washed with diethyl ether. This solid was dissolved in methanol (5 ml) and the pH adjusted to 10.5 by the addition of saturated aqueous sodium hydrogen carbonate. After 10 minutes, the reaction mixture was concentrated to low volume under reduced pressure and freeze-dried. The product was purified Diaion HP20SS resin, eluting with mixtures of tetrahydrofuran in water, to give, after freeze-drying, the title compound (0.03 g, 24%). This material was identical in all respects with the material obtained in Example 24.

EXAMPLE 50

Sodium [6R, 7R]-7-[2-(5-amino-1,2,4-thiadiazol-3-yl)-2-(Z)-(methoxyimino)acetamido]-3-[1-(methylamino)-pyridinium-4-thiomethyl]ceph-3-em-4-carboxylate a) 4-Methoxybenzyl [6R,7R]-3-[1-[N-(t-butyloxycarbonyl)-N-methylamino] pyridinium-4-thiomethyl]-7-[2-(Z)-(methoxyimino)-2-(5-tritylamino-1,2,4-thiadiazol-3-yl)acetamido]ceph-3-em-4-carboxylate iodide 2-(Z)-(Methoxyimino)-2-(5-tritylamino-1,2,4-thiadiazol-3-yl)acetic acid (0.222 g, 0.5 mmol) was dissolved in N,N-dimethylformamide (5 ml) under argon and treated with N,N-diisopropylethylamine (0.065 g, 0.5 mmol). The mixture was cooled to –40° C. and treated with methanesulphonyl chloride (0.057 g, 0.5 mmol). The temperature was allowed to rise to –20° C. and the mixture stirred at –20° C. for 0.5 h. The reaction mixture was recooled to –40° C. and treated with a solution of 4-methoxybenzyl [6R,7R]-7-amino-3-[1-[N-(t-butyloxycarbonyl)-N-methylamino] pyridinium-4-thiomethyl]ceph-3-em-4-carboxylate (0.35 g, 0.5 mmol) and pyridine (0.04 g, 0.5 mmol) in dry dichloromethane (10 ml). Cooling was removed and the mixture stirred at room temperature for 1 h. Dichloromethane (50 ml) was added and the mixture washed with water (5×20 ml), saturated brine, dried over magnesium sulphate and evaporated to dryness under reduced pressure. The residue was dissolved in acetone (10 ml) and treated with sodium iodide (0.075 g, 0.5 mmol). The mixture was stirred at room temperature for 0.5 h and then evaporated to dryness under reduced pressure. The title compound was obtained by chromatography on silica gel 60 eluting with mixtures of methanol in dichloromethane, (0.333 g, 59%); $\upsilon_{max}$ (KBr) 1781, 1725 and 1663 cm$^{-1}$; $\delta_H$ (CDCl$_3$) 1.52 (9H, s), 3.52–3.88 (2H, m), 3.68 (3H, s), 3.81 (3H, s), 4.13 (3H, s), 4.48 and 4.58 (2H, ABq, J 13Hz), 5.11 (1H, d, J 5Hz), 5.20 and 5.26 (2H, ABq, J 10Hz), 5.97 (1H, dd, J 5 and 10Hz), 6.81–6.92 (3H, m), 7.15–7.51 (17H, m), 8.08 (2H, d, J 7Hz), and 8.68 (2H, d, J 7Hz); m/z (F.A.B., 3-nitrobenzyl alcohol/sodium acetate) MH$^+$ 999.

b) Sodium [6R,7R]-7-[2-(5-amino-1,2,4-thiadiazol-3-yl)-2-(Z)-(methoxyimino)acetamido]-3-[1-(methylamino)pyridinium-4-thiomethyl]ceph-3-em-4-carboxylate The product of Example 50(a) (0.3 g, 0.27 mmol) was deprotected as in Example 2 (i,b) to give the title compound (0.048 g, 34%); $\upsilon_{max}$ (KBr) 1762, 1670 and 1617 cm$^{-1}$; $\delta_H$ [D$_2$O+(CD$_3$)$_2$CO] 3.16 (3H, s), 3.53 and 3.79 (2H, ABq, J 18Hz), 4.13 (3H, s), 4.31 and 4.59 (2H, ABq, J 14Hz), 5.23 (1H, d, J 5Hz), 5.90 (1H, d, J 5Hz), 8.00 (2H, d, J 7Hz), and 8.71 (2H, d, J 7Hz); m/z (F.A.B., thioglycerol) MH$^+$ 537.

EXAMPLE 51

[6R, 7R]-7-[2-(2-Amino-4-thiazolyl)-2-(Z)-[3,4-(methylenedioxy)benzyloxyimino]acetamido]-3-[1-(methylamino)pyridinium-4-thiomethyl)ceph-3-em-4-carboxylate a) 4-Methoxybenzyl [6R, 7R]-7-[1-(methylamino)pyridinium-4-thiomethyl]-7-[2-(Z)-[3,4-(methylenedioxy)benzyloxyimino)- 2-(2-tritylamino-4-thiazolyl)acetamido] ceph-3-em-4-carboxylate iodide The product of Preparation 36 (0.375 g, 0.6 mmol) was acylated with the product of Preparation 37 (0.352 g, 0.6 mmol) by the method described in Example 49(a). The product was purified by chromatography on silica gel 60, eluting with mixtures of ethanol in dichloromethane (0.186 g, 26%); $\upsilon_{max}$ (KBr) 1775, 1719 and 1675 cm$^{-1}$; $\delta_H$ (CDCl$_3$) 3.07 (3H, d, J 6Hz), 3.41 and 3.65 (2H, ABq, J 18Hz), 3.81 (3H, s), 4.27 and 4.47 (2H, ABq, J 13Hz), 5.00 (1H, d, J 5Hz), 5.05–5.28 (4H, m), 5.86 (1H, dd, J 5 and 9Hz), 5.94 (2H, s), 6.65–7.44 (25H, m), 7.70 (2H, d, J 7Hz), 8.77 (3H, d, J 7Hz); m/z (F.A.B., thioglycerol) M$^+$ 1018.

b) [6R, 7R]-7-[2-(2-Amino-4-thiazolyl)-2-(Z)-[3,4-(methylenedioxy)benzyloxyimino]acetamido]-3-[1-(methylamino(pyridinium-4-thiomethyl]ceph-3-em-4-carboxylate The product of Example 51(a) (0.176 g, 0.15 mmol) was deprotected as described in Example 2(ii) (b) to give the title compound (0.03 g, 30%); $\upsilon_{max}$ (KBr) 1765 and 1670 cm$^{-1}$; $\delta_H$ [(CD$_3$)$_2$SO] 2.99 (3H, br s), 3.20–3.50 (2H, m), 4.39 and 4.59 (2H, ABq, J 14Hz), 5.01 (3H, m), 5.57 (1H, dd, J 5 and 8Hz), 6.00 (2H, s), 6.71 (1H, s), 6.80–6.97 (3H, m), 7.23 (2H, br, exch.), 8.52 and 8.81 (each 2H, d, J 7Hz), 9.60 (1H, d, J 8Hz, exch.), 8.45–8.70 (1H, br, exch.); m/z (F.A.B., thioglycerol/acetic acid) MH$^+$ 656.

EXAMPLE 52

[6R,7R]-3-[1-Amino-5-methoxy-2-(methoxymethyl)-pyridinium-4-thiomethyl]-7-[2-(2-amino-4-thiazolyl)-2-(Z)-(methoxyimino)acetamido] -ceph-3-em-4-carboxylate a) 4-Methoxybenzyl-[6R,7R]-3-[1-(t-butyloxycarbonylamino)-5-methoxy-2-(methoxymethyl)pyridinium-4-thiomethyl] -7-[2-(2-amino-4-thiazolyl)-2-(Z)-(methoxyimino)-acetamido] -ceph-3-em-4-carboxylate iodide A solution of 4-methoxybenzyl-[6R,7R]-3-(chloromethyl)- 7-[2-(2-amino-4-thiazolyl)-2(Z)-(methoxyimino)acetamido] ceph-3-em-4-carboxylate (0.184 g, 0.33 mmol) in acetonitrile (5 ml) was treated with sodium iodide (0.05 g, 0.33 mmol) and the product from Preparation 38 (0.10 g, 0.33 mmol). After stirring at room temperature for 2.5 h the solvent was removed under reduced pressure and the residue chromatographed on silica gel 60 eluting with 5% ethanol in dichloromethane to give the title compound (0.144 g, 45%) as a pale brown foam; $\upsilon_{max}$ (KBr) 3300, 2930, 1780, 1720, 1680, and 1610 cm$^{-1}$; $\delta_H$ (CDCl$_3$+D$_2$O) inter alia 1.53 (9H, s), 3.46 (3H, s), 3.81 (3H, s), 3.98 (3H, s), 4.05 (3H, s), 4.68 (2H, m), 5.11 (1H, d, J 4.8Hz), 5.24 (2H, m), 6.01 (1H, d, J 4.8Hz), 6.77 (1H, s), 6.88 (2H, d, J 8.6Hz), 7.33 (2H, d, J 8.6Hz), 7.60 (1H, s), and 8.17 (1H, s); m/z (F.A.B. thioglycerol) M$^+$ 816.

b) [6R,7R]-3-[1-Amino-5-methoxy-2-(methoxymethyl)pyridinium-4-thiomethyl]-7-[2-(2-amino-4-thiazolyl)-2-(Z)-(methoxyimino)acetamido]ceph-3-em-4-carboxylate The product of Example 52(a) (0.134 g, 0.14 mmol) was treated with trifluoroacetic acid (1 ml) and the reaction mixture stirred for 1 h with ice-bath cooling. The mixture was then diluted with toluene and concentrated under reduced pressure. The residue was covered with water and the pH adjusted to pH 6 using saturated sodium hydrogen carbonate solution. The mixture was then washed with ethyl acetate and the aqueous phase concentrated under reduced pressure. The residue was purified on Diaion HP20SS resin eluting with water, tetrahydrofuran mixtures to give the title compound (0.017 g, 20%) as a freeze-dried solid; $\upsilon_{max}$ (KBr) 1760, 1670, and 1600 cm$^{-1}$; $\delta_H$ (D$_2$O) 3.43 (1H, d, J 17.6Hz), 3.44 (3H, s), 3.69 (1H, d, J 17.6Hz), 3.95 (3H, s), 3.99 (3H, s), 4.11 (1H, d, J 13.5Hz), 4.34 (1H, d, J 13.5Hz), 5.14 (1H, d, J 4.6Hz), 5.73 (1H, d, J 4.6Hz), 6.96 (1H, s), 7.79 (1H, s), and 8.22 (1H, s); m/z (F.A.B. thioglycerol) MH$^+$ 596.

EXAMPLE 53

[6R,7R]-3-(1-Amino-3-methoxy-2-methylpyridinium-4-thiomethyl)-7-[2-(2-amino-4-thiazolyl)-2-(Z)-(methoxyimino)-acetamido] -ceph-3-em-4-carboxylate a) 4-Methoxybenzyl-[6R,7R]-3-[1-(t-butyloxycarbonylamino)-3-methoxy-2-methylpyridinium-4-thiomethyl] -7-[2-(2-amino-4-thiazolyl)-2-(Z)-(methoxyimino)-acetamido] -ceph-3-em-4-carboxylate iodide A solution of 4-methoxybenzyl-[6R,7R]-3-(chloromethyl)- 7-[2-(2-amino-4-thiazolyl)-2(Z)-(methoxyimino)acetamido] ceph-3-em-4-carboxylate (0.150 g, 0.27 mmol) in acetonitrile (5 ml) was treated with sodium iodide (0.04 g, 0.27 mmol) and the product from Preparation 39 (0.147 g, 0.54 mmol). After stirring at room temperature for 1.5 h the solvent was removed under reduced pressure and the residue chromatographed on silica gel 60 eluting with ethanol dichloromethane mixtures to give the title compound (0.116 g, 47%) as a brown foam; $\upsilon_{max}$ (KBr) 3350, 1780, 1720, 1680, and 1610 cm$^{-1}$; $\delta_H$ (CDCl$_3$) inter alia 1.50 and 1.53 (9H, 2 x s) 2.56 and 2.61 (3H, 2 x s), 3.45 (2H, d, J 17.3Hz), 3.64 (3H, s), 3.84 (3H, s), 3.70–3.94 (2H, m), 4.03 (3H, s), 5.17 (1H, d, J 4.7Hz), 5.20–5.33 (2H, m), 6.04 (1H, dd, J 9.6 and 4.7Hz), 6.63 (0.7H, s), 6.69 (0.3H, s), 6.91 (2H, d, J 8.7Hz), 7.27–7.37 (3H, m), 8.02 (0.7H, d, J 6.9Hz), 8.14 (0.3H, d, J 6.6Hz); m/z (F.A.B. thioglycerol) M$^+$ 786.

b) [6R,7R]-3-(1-Amino-3-methoxy-2-methylpyridinium-4-thiomethyl]-7-[2-(2-amino-4-thiazolyl)-2-(Z)-(methoxyimino)acetamido] ceph-3-em-4-carboxylate The product of Example 53(a) (0.103 g, 0.11 mmol) was treated with trifluoroacetic acid and the reaction mixture stirred with ice-cooling for 1.5 h. The mixture was then diluted with toluene and concentrated under reduced pressure. The residue was covered with water and the pH adjusted to pH6 using saturated sodium hydrogen carbonate solution. The mixture was then washed with ethyl acetate and the aqueous phase concentrated under reduced pressure. The residue was purified by Diaion HP20SS resin, eluting with water, tetrahydrofuran mixtures, to give the title compound (0.027 g, 42%) as a freeze-dried solid; $\upsilon_{max}$ (KBr) 3310, 1760, 1670, 1600, and 1530 cm$^{-1}$; $\delta_H$ (D$_2$O) 2.64 (3H, s), 3.45 (1H, d, J 17.7Hz), 3.73 (1H, d, J 17.6Hz), 3.88 (3H, s), 3.96 (3H, s), 4.06 (1H, d, J 13.6Hz), 4.37 (1H, d, J 13.6Hz), 5.15 (1H, d, J 4.7Hz), 5.75 (1H, d, J 4.6Hz), 6.98 (1H, s), 7.60 (1H, d, J 7.1Hz), and 8.32 (1H, d, J 7.0Hz); m/z (F.A.B. thioglycerol) M$^+$ 566.

EXAMPLE 54

[6R, 7R]-7-[2-(2-Ammonio-4-thiazolyl)-2-(Z)-(methoximino)acetamido]
-3-[1-(methylamino)pyridinium-4-thiomethyl]
ceph-3-em-4-carboxylic acid, dichloride salt

[6R,7R]-7-[2-(2-Amino-4-thiazolyl)-2-(Z)-(methoximino)acetamido- 3-[1-(methylamino)pyridinium-4-thiomethyl]ceph -3-em-4-carboxylate (0.1 g, 0.19 mmol) was dissolved in 2N hydrochloric acid (0.5 ml) and then the solution was added dropwise to vigorously stirred isopropanol (26 ml). After cooling at 0° C. for 20 minutes, the precipitate was filtered off, washed with cold isopropanol, and dried in vacuo to afford the title product (0.073 g, 64%); $\upsilon_{max}$ (KBr) 1776, 1710, 1671, 1623 and 1540 cm$^{-1}$; $\delta_H$ (D$_2$O) 3.01 (3H, s), 3.49 and 3.74 (2H, ABq, J 17.8Hz), 4.02 (3H, s), 4.18 and 4.41 (2H, ABq, J 13.6Hz), 5.17 (1H, d, J 4.5Hz), 5.74 (1H, d, J 4.5Hz), 7.11 (1H, s), 7.79 (2H, d, J 7.2Hz), and 8.52 (2H, d, J 7.2Hz).

EXAMPLE 55

[6R,7R]-3-(1-Aminopyridinium-4-thiomethyl)-7-[2-(2 -ammonio-4-thiazolyl)-2-(Z)-(methoximino)acetamido] ceph-3-em-4-carboxylic acid, dichloride salt

[6R,7R]-3-(1-Aminopyridinium-4-thiomethyl)-7-[2-(2 -amino-4-thiazolyl)-2-(Z)-(methoximino)acetamido]ceph-3-em-4-carboxylate (0.05 g, 0.09 mmol) was converted to the title product (0.03 g; 53%) using the method described in Example 54; $\upsilon_{max}$ (KBr) 1774, 1710, 1670, 1628, and 1540 cm$^{-1}$; $\delta_H$ (D$_2$O) 3.48 and 3.74 (2H, ABq, J 17.7Hz), 4.02 (3H, s), 4.18 and 4.41 (2H, ABq, J 13.6Hz), 5.16 (1H, d, J 4.7Hz), 5.74 (1H, d, J 4.7Hz), 7.11 (1H, s), 7.74 (2H, d, J 7.1Hz), and 8.40 (2H, d, J 7.1Hz).

EXAMPLE 56

[6R, 7R]-7-[2-(2-Ammonio-4-thiazolyl)-2-(Z)-(methoximino)acetamido]
-3-[1-(methylamino(pyridinium-4-thiomethyl]
ceph-3-em-4-carboxylic acid, sulphate salt

[6R,7R]-7-[2-(2-Amino-4-thiazolyl)-2-(Z)-(methoximino)acetamido] -3-[1-(methylamino)pyridinium-4-thiomethyl] ceph-3-em-4-carboxylate (0.1 g, 0.19 mmol) was converted to the title product (0.128 g, 100%) using the method described in Example 54, replacing hydrochloric acid with sulphuric acid; $\upsilon_{max}$ (KBr) 1773, 1716, 1670, 1623 and 1541 cm$^{-1}$; $\delta_H$ (D$_2$O) 3.01 (3H, s), 3.51 and 3.76 (2H, ABq, J 17.8Hz), 4.03 (3H, s), 4.28 and 4.41 (2H, ABq, J 13.5Hz), 5.19 (1H, d, J 4.6Hz), 5.75 (1H, d, J 4.6Hz), 7.12 (1H, s), 7.79 (2H, d, J 7.2Hz) and 8.53 (2H, d, J 7.2Hz).

EXAMPLE 57

[6R, 7R]-7-[2-(2-Amino-4-thiazolyl)-2-(Z)-(methoxyimino)acetamido]
-3-[1-[(2-methoxyethyl)amino]pyridinium-
4-thiomethyl]ceph-3-em-4-carboxylate a) 4-Methoxybenzyl [6R, 7R]-3-[1-(t-butyloxycarbonyl)-
1-[(2-methoxyethyl)aminopyridinium-4-thiomethyl]
-7-[2-(Z)-(methoxyimino)-2-(2-tritylamino-4
-thiazolyl]acetamido]ceph-3-em-4-carboxylate 4-Methoxybenzyl [6R,7R]-3-(chloromethyl)-7-[2-(Z)-(methoxyimino)- 2-(2-tritylamino-4-thiazolyl)acetamido]-ceph- 3-em-4-carboxylate (0.08 g, 0.1 mmol) in acetonitrile (5 ml) was treated with sodium iodide (0.015 g, 0.1 mmol) and 1-[N-(t-butyloxycarbonyl)-N-(2 -methoxyethyl)amino] -4-thiopyridone (0.028 g, 0.1 mmol). The mixture was stirred for 3 h, then filtered through celite and the filtrate added to vigorously stirred diethyl ether. The precipitate was filtered off and dried to give the title compound (0.054 g, 46%); $\upsilon_{max}$ (KBr) 1784, 1727, 1677, and 1615 cm$^{-1}$; $\delta_H$ (CDCl$_3$+ CD$_3$OD) 1.52 (9H, s), 3.38 (3H, s), 3.60 (1H, d, J 17Hz), partially covered by 3.61 (2H, t, J 5Hz), 3.81 (3H, s), partially covering 3.82 (1H, d, J 17Hz), 4.06 (3H, s), 4.19 (2H, t, J 5Hz), 4.47 and 4.60 (2H, ABq, J 12Hz), 5.09 (1H, d, J 5Hz), 5.23 (2H, s), 5.92 (1H, d, J 5Hz), 6.71 (1H, s), 6.89 (2H, d, J 8.5Hz), 7.31 (17H, m), 7.99 (2H, d, J 7Hz)., and 8.60 (2H, d, J 7Hz); m/z (F.A.B., thioglycerol) M$^+$ 1042.

b) [6R, 7R]-7-[2-(2-Amino-4-thiazolyl)-2-(Z)-(methoxyimino)acetamido]
-3-[1-[(2-methoxyethyl)amino]
pyridinium-4-thiomethyl]ceph-3-em-4-carboxylate The product from Example 57(a) (0.05 g, 0.04 mmol) was treated with trifluoroacetic acid (1 ml) and stirred for 5 minutes. The mixture was diluted with toluene (1 ml) and then evaporated to dryness under reduced pressure. The residue was diluted with water (5 ml) and neutralised with aqueous sodium hydrogen carbonate to pH 6.5. Purification on Diaion HP20SS resin eluting with water, tetrahydrofuran mixtures gave the title compound (0.015 g, 60%); $\upsilon_{max}$ (KBr) 1763, 1669, and 1617 cm$^{-1}$; $\delta_H$ (D$_2$O) 3.31 (3H, s), 3.44 and 3.71 (2H, ABq, J 18.5Hz), 3.47 (2H, m), 3.58 (2H, m), 3.95 (3H, s), 4.14 and 4.40 (2H, ABq, J 14Hz), 5.15 (1H, d, J 4.5Hz), 5.74 (1H, d, J 4.5Hz), 6.97 (1H, s), 7.80 (2H, d, J 5Hz), and 8.51 (2H, d, J 5Hz); m/z (F.A.B., thioglycerol) M$^+$ 580.

EXAMPLE 58

6R,7R]-7-[2-(2-Amino-4-thiazolyl)-2-(Z)-(methoxyimino)acetamido]
-3-[1-(1,2,4-triazol-4-yl)pyridinium-
4-thiomethyl]ceph-3-em-4-carboxylate b) 4-Methoxybenzyl
[6R,7R]-7-[2-(Z)-(methoxyimino)-
2-(2-tritylamino-4-thiazolyl)acetamido]-3-[1
-(1,2,4-triazol-4-yl)pyridinium-4-thiomethyl]ceph-3-em-
4-carboxylate iodide 4-Methoxybenzyl [6R,7R]-3-(chloromethyl)-7-[2-(Z)-(methoxyimino)- 2-(2-tritylamino-4-thiazolyl)acetamido] -ceph-3-em-4-carboxylate (0.15 g, 0.19 mmol) in acetonitrile (5 ml) was treated successively with sodium iodide (0.58 g, 0.28 mmol) and 1-(1,2,4-triazol-4-yl)-4 -thiopyridone (0.05 g, 0.28 mmol). N,N-Dimethylformamide (1 ml) was added to give a clear solution. The mixture was stirred for 2 h, then filtered through celite and the filtrate added to vigorously stirred diethyl ether (50 ml). The precipitate was filtered off, dried and purified on silica gel 60 eluting with ethanol, dichloromethane (1:9) to give the title compound (0.156 g, 78%); $\upsilon_{max}$ (KBr) 1779, 1718, 1670 and 1614 cm$^{-1}$; $\delta_H$ (CDCl$_3$+CD$_3$OD) 3.61 and 3.80 (2H, ABq, J 18Hz), 3.81 (3H, s), 4.03 (3H, s), 4.47 and 4.62 (2H, ABq, J 12Hz), 5.14 (1H, d, J 5Hz), 5.24 (2H, s), 5.88 (1H, d, J 5Hz), 6.69 (1H, s), 6.88 (2H, d), 7.32 (17H, m), 8.02 (2H, d, J 7Hz), 8.82 (2H, d, J 7Hz), and 9.25 (2H, s); m/z (F.A.B., 3-nitrobenzyl alcohol) M$^+$ 936.

b) [6R, 7R]-7-[2-(2-Amino-4-thiazolyl)-2-(Z)-(methoxyimino)acetamido] -3-[1-(1,2,4-triazol-4-yl)pyridinium-4-thiomethyl]ceph-3-em-4-carboxylate p The product from Example 58(a) (0.07 g, 0.07 mmol) was treated with trifluoroacetic acid (2 ml) and stirred for 10 minutes. Toluene (2 ml) was added and the mixture was evaporated to dryness under reduced pressure. The residue was redissolved in a mixture of acetonitrile and water. After removal of the organic solvent under reduced pressure the mixture was purified on Diaion HP20SS resin to give the title compound (0.00359; 9%); $\upsilon_{max}$ (KBr) 1762, 1670, and 1616 cm$^{-1}$; $\delta_H$ (D$_2$O) 3.57 and 3.85 (2H, ABq, J 17.5Hz), 4.05 (3H, s), 4.42 and 4.56 (2H, ABq, J 13.5Hz), 5.30 (1H, d, J 4.5Hz), 5.85 (1H, d, J 4.5Hz), 7.08 (1H, s), 8.18 (2H, d, J 7Hz), 8.91 (2H, d, J 7Hz), and 9.27 (2H, s); m/z (F.A.B., thioglycerol, acetic acid) MH$^+$ 574.

EXAMPLE 59

[6R, 7R]-7-[2 -(2-Amino-4-thiazolyl)-2-(Z)-(methoxyimino)-acetamido] -3-[1-[(6-chloropyridin-2-yl)amino] pyridinium-4-thiomethyl]ceph-3-em-4-carboxylate a) 4-Methoxybenzyl [6R, 7R]-3-[1-[(6-chloropyridin-2-yl)amino]pyridinium-4-thiomethyl]-7-[2-(Z)-(methoxyimino)-2-(2-tritylamino-4-thiazolyl)acetamido]ceph-3-em-4-carboxylate iodide 4-Methoxybenzyl [6R,7R]-3-(chloromethyl)-7-[2-(Z)-(methoxyimino)- 2-(2-tritylamino-4-thiazolyl)acetamido] -ceph-3-em-4-carboxylate (0.20 g, 0.25 mmol) in dichloromethane (5 ) was treated successively with 1-[(6 -chloropyridin-2-yl)amino]-4-thiopyridone (0.07 g, 0.29 mmol) and sodium iodide (0.038 g, 0.25 mmol). The mixture was stirred for 2.5 h, then filtered through celite and the filtrate added to vigorously stirred diethyl ether (50 ml). The precipitate was filtered off and dried to give the title compound (0.227 g, 80%); $\upsilon_{max}$ (KBr) 1784, 1719, 1661, and 1618 cm$^{-1}$; $\delta_H$ (CDCl$_3$+ CD$_3$OD) 3.58 and 3.77 (2H, ABq, J 17Hz), 3.76 (3H, s), 4.00 (3H, s), 4.39 and 4.52 (2H, ABq, J 12.5Hz), 5.15 (1H, d, J 5Hz), 5.22 and 5.28 (2H, ABq, J 12.5Hz), 5.81 (1H, d, J 5Hz), 6.71 (1H, s), 6.86 (2H, d, J 8.5Hz), 6.93 (1H, d, J 8Hz), 7.08 (1H, d, J 8Hz), 7.32 (17H, m), 7.76 (1H, t, J 8Hz), 7.91 (2H, d, J 7Hz), and 8.49 (2H, d, J 7Hz); m/z (F.A.B., thioglycerol) M$^+$ 995.

b) [6R, 7R]-7-[2-(2-Amino-4-thiazolyl)-2-(Z)-(methoxyimino)acetamido] -3-[1-[(6-chloropyridin-2-yl)amino] pyridinium-4-thiomethyl]ceph-3-em-4-carboxylate The product from Example 59(a) (0.22 g, 0.20 mmol) in dichloromethane (20 ml) was treated with trifluoroacetic acid (1 ml, 13 mmol) and stirred for 2 h. Toluene (1 ml) was added and the mixture evaporated to dryness under reduced pressure. The residue was redissolved in acetonitrile and water, then neutralised with aqueous sodium hydrogen carbonate to pH 7.0. The organic solvent was removed under reduced pressure. Purification of the aqueous mixture on Diaion HP20SS resin eluting with water, tetrahydrofuran mixtures gave the title compound (0.08 g, 64%); $\upsilon_{max}$ (KBr) 1764, 1670, and 1622 cm$^{-1}$; $\delta_H$ (D$_2$O+CF$_3$CO$_2$D) 3.58 and 3.77 (2H, ABq, J 18Hz), 4.01 (3H, s), 4.43 and 4.53 (2H, ABq, J 14Hz), 5.21 (1H, d, J 4.5Hz), 5.71 (1H, d, J 4.5 Hz), 6.82 (1H, d, J 8Hz), 7.07 (1H, d, J 8Hz), 7.10 (1H, s), 7.72 (1H, t, J 8Hz), 7.90 (2H, d, J 7Hz), and 8.52 (2H, d, J 7Hz); m/z (F.A.B., thioglycerol) MH$^+$ 633.

EXAMPLE 60

[6R, 7R]-7-[2-(2-Amino-4-thiazolyl)-2-(Z)-(methoxyimino)acetamido] -3-[1-(pyrazineamino(pyridinium-4-thiomethyl] ceph-3-em-4-carboxylate a) 4-Methoxybenzyl [6R, 7R]-7-[2-(2-amino-4-thiozolyl)-2-(Z)-(methoxyimino)acetamido]-3-[1-(pyrazineamino-(pyridinium- 4-thiomethyl]ceph-3-em-4-carboxylate iodide 4-Methoxybenzyl [6R,7R]-3-(chloromethyl)-7-[2-(Z)-(methoxyimino)- 2-(2-tritylamino-4-thiazolyl)acetamido] -ceph-3-em-4-carboxylate (0.095 g, 0.12 mmol) in acetonitrile (5 ml) was treated with 1-(pyrazine amino)-4-thiopyridone (0.024 g, 0.12 mmol) and sodium iodide (0.018 g, 0.12 mmol). The mixture was stirred at room temperature for 4 h followed by filtration and dropwise addition to diethyl ether (40 ml). The precipitate was filtered and dried in vacuo to give the title compound (0.054 g, 47%); $\delta_H$ 3.60 and 3.79 (2H, ABq, J 18Hz), 3.81 (3H, s), 4.15 (3H, s), 4.40 and 4.61 (2H, ABq, J 13Hz), 5.14 (1H, d, J 5Hz), 5.24 and 5.95 (2H, ABq, J 12Hz), 5.96 and 6.0 (1H, dd, J 5Hz), 6.81 (1H, s), 6.92 (2H, d, J 8.5Hz), 7.25–7.45 (17H, m), 7.86 (2H, d, J 6.5Hz), 8.06 (1H, s), 8.32 (1H, s), 8.55 (2H, d, J 6.5Hz), and 8.83 (1H, s); m/z (F.A.B., thioglycerol) MH$^+$ 962.

b) [6R, 7R]-7-[2-(2-Amino-4-thiazolyl)-(Z)-(methoxyimino)acetamido] -3-[1-(pyrazineamino)pyridinium-4-thiomethyl]ceph-3-em-4-carboxylate The product of Example 60(a) (0.05 g, 0.05 mmol) was treated with trifluoroacetic acid (1 ml). The mixture was stirred at room temperature for 5 minutes, toluene (10 ml) was added and the mixture evaporated to dryness under reduced pressure. Purification on Diaion HP20SS resin gave the title compound (0.012 g, 39%); $\upsilon_{max}$ (KBr) 1766, 1670, 1620, and 1530 cm$^{-1}$; $\delta_H$ (D$_2$O) 3.48 and 3.76 (2H, ABq, J 18Hz), 3.96 (3H, s), 4.21 and 4.48 (2H, ABq, J 13.5Hz), 5.19 (1H, d, J 4.5Hz), 5.77 (1H, d, J 4.5Hz), 7.0 (1H, s), 7.95 (2H, d, J 7Hz), 8.08 (1H, s), 8.19 (1H, s), 8.34 (1H, s), and 8.53 (2H, d, J 7Hz).

EXAMPLE 61

[6R, 7R]-7-[2-(2-Amino-4-thiazolyl)-2-(Z)-
(methoxyimino)acetamido]
-3-[1-[(2-methyl-4-thiazolyl)methylamino]
pyridinium-4-thiomethyl]ceph-3-em-4-carboxylate a) 4-Methoxybenzyl 6R,
7R]-3-[1-[N-(t-butyloxycarbonyl)-N-[
(2-methyl-4-thiazolyl)methyl]amino]pyridinium-
4-thiomethyl]-7-[2-(Z)-(methoxyimino)-2-(2-
tritylamino-
4-thiazolyl)acetamido]ceph-3-em-4-carboxylate
iodide 4-Methoxybenzyl [6R,7R]-3-(chloromethyl)-7-[2-(Z)-(methoxyimino)- 2-(2-tritylamino-4-thiazolyl)acetamido] ceph-3-em-4-carboxylate (0.095 g, 0.12 mmol) in acetonitrile (10 ml) was treated with 1-[N-(t-butyloxycarbonyl)-N-(2-methyl-4-thiazolyl)methylamino]-4-thiopyridone (0.04 g, 0.12 mmol) and sodium iodide (0.019 g, 0.13 mmol). The mixture was stirred at room temperature for 3.5 h, then filtered and evaporated under reduced pressure to a smaller volume and added dropwise to diethylether (40 ml). The precipitate was filtered to give the title compound (0.109 g, 83%); $\delta_H$ 1.59 (9H, s), 2.72 (3H, s), 3.53 and 3.86 (2H, ABq, J 18.5Hz), 3.81 (3H, s), 4.07 (3H, s), 4.44 and 4.55 (2H, ABq, J 12Hz), 5.10 (1H, d, J 5Hz), 5.24 (4H, d, J 8Hz), 5.94 and 5.98 (1H, dd, J 5Hz), 6.72 (1H, s), 6.89 (2H, d, J 8.5Hz), 7.01 (1H, s), 7.25–7.38 (17H, m), 7.93 (2H, d, J 7Hz), and 8.68 (2H, d, J 7Hz); m/z (F.A.B., thioglycerol) MH$^+$ 1095.

b) [6R, 7R]-7-[2-(2-Amino-4-thiazolyl)-2-(Z)-
(methoxyimino)acetamido-
3-[1-[(2-methyl-4-thiazolyl)methylamino]
pyridinium-4-thiomethyl]ceph-3-em-4-carboxylate The product of Example 61(a) (0.104 g, 0.09 mmol) was treated with trifluoroacetic acid (1 ml). The mixture was stirred for 5 minutes, toluene (10 ml) was added and the mixture evaporated to dryness under reduced pressure. Purification on Diaion HP20SS resin gave the title compound (0.029 g, 50%); $\upsilon_{max}$ (KBr) 1767, 1668, 1619, and 1530 cm$^{-1}$; $\delta_H$ [D$_2$O+(CD$_3$)$_2$CO] 2.69 (3H, s), 3.47 and 3.73 (2H, ABq, J 17.5Hz), 3.99 (3H, s), 4.26 and 4.46 (2H, ABq, J 14Hz), 4.54 (2H, s), 5.19 (1H, d, J 4.5Hz), 5.79 (1H, d, J 4.5Hz), 6.97 (1H, s), 7.27 (1H, s), 7.86 (2H, d, J 7Hz), and 8.41 (2H, d, J 7Hz); m/z (F.A.B., thioglycerol) MH$^+$ 633.

EXAMPLE 62

[6R, 7R]-7-[2-(2-Amino-4-thiazolyl)-2-(Z)-
(methoxyimino)acetamido]
-3-[1-[(2-imidazolin-2-yl)amino]pyridinium-
4-thiomethyl]ceph-3-em-4-carboxylate a) 4-Methoxybenzyl [6R,7R]-3-[1-[(2-imidazolin-2
-yl)amino]pyridinium-4-thiomethyl]-7-[2-(Z)-
(methoxyimino)-
2-(2-tritylamino-4-thiazolyl)acetamido]ceph-3
-em-4-carboxylate iodide 4-Methoxybenzyl [6R,7R]-3-(chloromethyl)-7-[2-(Z)-(methoxyimino)- 2-(2-tritylamino-4-thiazolyl)acetamido] -ceph-3-em-4-carboxylate (0.1 g, 0.126 mmol) in N,N-dimethylformamide (1 ml) and acetonitrile (5 ml) was treated with 1-[(2-imidazolin-2-yl)amino]-4-thiopyridone (0.03 g, 0.15 mmol) and sodium iodide (0.019 g, 0.13 mmol). The mixture was stirred for 3.5 h then filtered. The filtrate was evaporated to a smaller volume and added to stirred diethyl ether (40 ml). The precipitate was filtered off and dried in vacuo to give the title compound (0.078 g, 65%); $\delta_H$ (CDCl$_3$) 3.65 (4H, s), 3.65–3.91 (2H, m), 3.81 (3H, s), 4.08 (3H, s), 4.36 and 4.42 (2H, ABq, J 13.5Hz), 5.20 and 5.31 (2H, ABq, J 11.7Hz), 5.21 (2H, d, J 5Hz), 5.93 (1H, dd, J 5Hz), 6.75 (1H, br s), 6.89 (2H, d, J 8.5Hz), 7.08 (1H, br s), 7.24–7.35 (15H, m), 7.38 (2H, d, J 8.5Hz), 7.54 (2H, d, J 7Hz), and 7.98 (2H, d, J 7Hz); m/z (F.A.B., thioglycerol) M$^+$ 952.

b) [6R,7R]-7-[2-(2-Amino-4-thiazolyl)-2-(Z)-
(methoxyimino)acetamido]
-3-[1-[(2-imidazolin-2-yl)amino]
pyridinium-4-thiomethyl]ceph-3-em-4-carboxylate The product of Example 62(a) (0.078 g, 0.08 mmol) was treated with trifluoroacetic acid (1 ml). The mixture was stirred for 5 minutes, toluene (5 ml) was then added and the mixture evaporated under reduced pressure. Purification on Diaion HP20SS resin gave the title compound (0.035 g, 73%); $\upsilon_{max}$ (KBr) 1765, 1616, 1528 and 1474 cm$^{-1}$; $\delta_H$ (CDCl$_3$) 3.46 and 3.75 (2H, ABq, J 17.5Hz), 3.57 (4H, s), 3.97 (3H, s), 4.13 and 4.44 (2H, ABq, J 14Hz), 5.16 (1H, d, J 4.6Hz), 5.76 (1H, d, J 4.6Hz), 6.97 (1H, s), 7.80 (2H, d, J 7Hz), and 8.35 (2H, d, J 7Hz); m/z (F.A.B., thioglycerol) MH$^+$ 590.

EXAMPLE 63

[6R, 7R]-7-[2-(2-Amino-4-thiazolyl)-2-(Z)-
(methoxyimino)acetamido]
-3-[1-(phthalazin-1-yl)pyridinium-4
-thiomethyl]ceph-3-em-4-carboxylate a) 4-Methoxybenzyl
[6R,7R]-7-[2-(Z)-(methoxyimino)-
2-(2-tritylamino-4-thiazolyl)acetamido]-3-[1-
(phthalazin- 1-yl)
pyridinium-4-thiomethyl]ceph-3-em-4 -carboxylate
iodide 4-Methoxybenzyl [6R,7R]-3-(chloromethyl)-7-[2-(Z)-methoxyimino)- 2-(2-tritylamino-4-thiazolyl)acetamido] -ceph-3-em-4-carboxylate (0.14 g, 0.17 mmol) in acetonitrile (10 ml) was treated with 1-(phthalazin-1-yl-amino)-4-thiopyridone (0.05 g, 0.19 mmol) and sodium iodide (0.027 g, 0.18 mmol). The mixture was stirred for 3 h, then filtered. The filtrate was evaporated to a smaller volume and added dropwise to diethylether (40 ml) with stirring. The precipitate was left stirring for a further 10 minutes, recovered, and dried in vacuo to give the title product (0.149 g, 87%); $\delta_H$ (CDCl$_3$) 3.6 and 3.77 (2H, ABq, J 18Hz), 3.72 (3H, s), 4.06 (3H, s), 4.27 and 4.66 (2H, ABq, J 1 3.5Hz), 5.17 and 5.31 (2H, ABq, J 11.6Hz), 5.30 (2H, s), 5.9 (1H, q, J 5Hz), 6.39 (1H, br s), 6.83 (2H, d, J 8.5Hz), 7.27–7.30 (18H, m), 7.37 (2H, d, J 8.5Hz), 7.71 (2H, d, J 7Hz), 7.77–7.90 (2H, m), 8.01 (2H, d, J 7Hz), 8.30 (1H, s), and 8.41 (1H, d, J 7Hz); m/z (F.A.B., thioglycerol) MH$^+$ 1012.

b) [6R,7R]-7-[2-(2-Amino-4-thiazolyl)-2-(Z)-
(methoxyimino)acetamido]
-3-[1-(phthalazin-1-yl)pyridinium-
4-thiomethyl]ceph-3-em-4-carboxylate The product of Example 63(a) (0.14 g, 0.14 mmol) was treated with trifluoroacetic acid (1 ml) in dichloromethane (20 ml). The mixture was stirred for 2 h, toluene (5 ml) was added and the mixture evaporated to dryness under reduced pressure. Purification on Diaion HP20SS resin gave the title compound (0.038 g, 43%); $\upsilon_{max}$ (KBr) 1767, 1670, 1611, and 1533 cm$^{-1}$; δ (D$_2$O) 3.60 and 3.86 (2H, ABq, J 17.5Hz), 4.04 (3H, s), 4.35 and 4.59 (2H, ABq, J 13.5Hz), 5.27 (1H, d, J 4.5Hz), 5.86 (1H, d, J 4.5Hz), 7.0 (1H, s), 8.02–8.08 (3H, m), 8.13 (2H, d, J 7Hz), 8.52 (2H, m), and 8.61 (2H, d, J 7Hz); m/z (F.A.B., thioglycerol) MH$^+$ 650.

EXAMPLE 64

[6R,7R]-7-[2-(2-Amino-4-thiazolyl)-2-(Z)-(methoxyimino)acetamido]
-3-[-3-[1-[(cyanomethyl)amino]pyridinium-4-thiomethyl]ceph-3-em-4-carboxylate a) 4-Methoxybenzyl [6R, 7R]-3-[1-[N-(t-butyloxycarbonyl)-N-(cyanomethyl)-amino] pyridinium-4-thiomethyl]-
7-[2-(Z)-(methoxyimino)-2-(2-tritylamino-4-thiazolyl)-acetamido] ceph-3-em-4-carboxylate iodide 4-Methoxybenzyl [6R,7R]-3-(chloromethyl)-7-[2-(Z)-(methoxyimino)- 2-(2-tritylamino-4-thiazolyl)acetamido] -ceph-3-em-4-carboxylate (0.14 g, 0.17 mmol) in acetonitrile (10 ml) was treated with 1-[N-(t-butyloxycarbonyl)-N-(cyanomethyl)amino] -4-thiopyridone (0.05 g, 0.19 mmol) and sodium iodide (0.026 g, 0.17 mmol). The mixture was stirred for 2 h, filtered and then evaporated under reduced pressure to a smaller volume. The solution was added dropwise to diethyl ether (40 ml) with stirring and left stirring for a further 20 minutes. The product was isolated by filtration and dried in vacuo (0.122 g, 68%); δ$_H$ (CDCl$_3$) 1.58 (9H, s), 3.56 and 3.79 (2H, ABq, J 17Hz), 3.81 (3H, s), 4.06 (3H, s), 4.35 and 4.57 (2H, ABq, J 12Hz), 5.13 (1H, d, J 5Hz), 5.24 (2H, ABq, J 10Hz), 5.46 (2H, s), 5.92 (1H, q, J 5Hz), 6.70 (1H, s), 6.89 and 7.36 (4H, 2d, J 8.5Hz), 7.29 (15H, s), 7.95 (2H, d, J 7Hz), and 8.80 (2H, d, J 7Hz); m/z (F.A.B., thioglycerol) MH$^+$ 1023.

b) 6R, 7R]-7-[2-(2-Amino-4-thiazolyl)-2-(Z)-(methoxyimino)acetamido]
-3-[1-(cyanomethyl)amino]
pyridinium-4-thiomethyl]ceph-3-em-4-carboxylate The product of Example 64(a) (0.122 g, 0.12 mmol) was treated with trifluoroacetic acid (2 ml). The reaction mixture was stirred for 5 minutes, toluene (5 ml) was added and the mixture evaporated under reduced pressure. Purification on Diaion HP20SS resin gave the title compound (0.025 g, 38%); $\upsilon_{max}$ (KBr) 1767, 1669, 1617, and 1528 cm$^{-1}$; δ$_H$ (D$_2$O) 3.43 and 3.72 (2H, ABq, J 17.5Hz), 3.94 (3H, s), 4.15 and 4.41 (2H, ABq, J 13.5Hz), 4.39 (2H, s), 5.15 (1H, d, J 4.5Hz), 5.74 (1H, d, J 4.5Hz), 6.97 (1H, s), 7.85 (2H, d, J 7Hz), and 8.58 (2H, d, J 7Hz); m/z (F.A.B., thioglycerol) MH$^+$ 561.

EXAMPLE 65

[6R, 7R]-7-[2-(2-Amino-4-thiazolyl)-2-(Z)-(methoxyimino)acetamido]
-3-[1-(prop-2-yn-1-ylamino)pyridinium-4-thiomethyl]ceph-3-em-4-carboxylate a) 4-Methoxybenzyl [6R, 7R]-3-[1-[N-(t-butyloxycarbonyl)-N-(prop-2-yn-1-yl)amino]pyridinium-4-thiomethyl]
-7-[2-(Z)-(methoxyimino)-2-(2-tritylamino-4-thiazolyl)acetamido] ceph-3-em-4-carboxylate 4-Methoxybenzyl [6R,7R]-3-(chloromethyl)-7-[2-(Z)-(methoxyimino)- 2-(2-tritylamino-4-thiazolyl)acetamido] ceph-3-em-4-carboxylate (0.125 g, 0.18 mmol) in acetonitrile (10 ml) was treated with 1-[N-(t-butyloxycarbonyl)-N-(prop- 2-yn-1-yl)amino]-4-thiopyridone (0.046 g, 0.17 mmol) and sodium iodide (0.024 g, 0.16 mmol). The mixture was stirred for 35 minutes, then filtered and evaporated under reduced pressure to a smaller volume. The solution was added dropwise to diethyl ether (40 ml) with stirring and left stirring for a further 20 minutes. The product was isolated by filtration and dried in vacuo (0.103 g, 64%); δ$_H$ (CDCl$_3$), 1.55 (9H, s), 3.54 and 3.87 (2H, ABq, J 18Hz), 3.81 (3H, s), 4.07 (3H, s), 4.48 and 4.62 (2H, ABq, J 12Hz), 4.91 (2H, d, J 2Hz), 5.1 (1H, d, J 5Hz), 5.23 (2H, s), 5.96 (1H, q, J 5Hz), 6.72 (1H, s), 6.77 (1H, d, J 9Hz), 6.89 (2H, d, J 8.5Hz), 7.02 (1H, s), 7.30 (15H, s), 7.35 (2H, d, J 8.5Hz), and 8.08 and 8.70 (4H, 2d, J 7Hz); m/z (F.A.B., thioglycerol) MH$^+$ 1022.

b) [6R,7R]-7-[2-(2-Amino-4-thiazolyl)-2-(Z)-(methoxyimino)acetamido]
-3-[1-(prop-2-yn-1-ylamino)pyridinium-4-thiomethyl]ceph-3-em-4-carboxylate The product of Example 65(a) (0.103 g, 0.1 mmol) was treated with trifluoroacetic acid (2 ml). The reaction mixture was stirred for 5 minutes, toluene (10 ml) was added and the mixture evaporated under reduced pressure. Purification on Diaion HP20SS resin gave the title compound (0.033; 59%); $\upsilon_{max}$ (KBr) 1779, 1675, 1623, and 1527 cm$^{-1}$; δ$_H$ (D$_2$O) 2.78 (1H, s), 3.49 and 3.75 (2H, ABq, J 17.5Hz), 4.02 (3H, s), 4.09 (2H, s), 4.23 and 4.43 (2H, ABq, J 13.5Hz), 5.18 (1H, d, J 4.5Hz), 5.75 (1H, d, J 4.5Hz), 7.11 (1H, s), and 7.81 and 8.55 (4H, 2d, J 6.5Hz); m/z (F.A.B., thioglycerol) MH$^+$ 560.

EXAMPLE 66

[6R, 7R]-7-[2-(2-Amino-4-thiazolyl)-2-(Z)-(methoximino)acetamido]
-3-[1-(methylamino(pyridinium-4-thiomethyl]
-ceph-3-em-4-carboxylate-1-oxide To a solution of [6R,7R]-7-[2-(2-amino-4-thiazolyl)-2-(Z)-(methoximino)acetamido]-3-[1-(methylamino)pyridinium- 4-thiomethyl]ceph-3-em-4-carboxylate (0.058 g, 0.11 mmol) in water (4 ml) and methanol (2 ml) at 0° C. was added peracetic acid (0.2 ml. of a 3.3% v/v solution in acetic acid, 0.11 mmol). After 20 minutes. further peracid (0.04 ml) was added and the reaction stirred a further 1 h. After neutralisation to pH 7 with saturated sodium hydrogen carbonate solution, the volume was reduced in vacuo and the aqueous solution poured onto HP20SS resin. Elution with aqueous tetrahydrofuran afforded the title product (0.045 g, 75%); $\upsilon_{max}$ (KBr) 1777, 1670, 1616 and 1527 cm$^{-1}$; δ$_H$ (D$_2$O) 3.03 (3H, s), 3.68 and 3.96 (2H, ABq, J 18.2Hz), 3.99 (3H, s), 4.15 and 4.54 (2H, ABq, J 14Hz), 4.94 (1H, d, J 4Hz), 5.96 (1H, d, J 4Hz), 6.99 (1H, s), 7.81 (2H, d, J 7.1Hz), and 8.53 (2H, d, J 7.1Hz); m/z (F.A.B., thioglycerol) MH$^+$ 552.

EXAMPLE 67

[6R, 7R]-3-(1-Amino-2,6-dimethylpyridinium-4-thiomethyl)-
7-[2-(2-amino-4-thiazolyl)-2-(Z)-(methoxyimino)-acetamido] ceph-3-em-4-carboxylate a) 4-Methoxybenzyl[6R, 7R]-3-[2-(t-butyloxycarbonylamino)-2,6-dimethylpyridinium-4-thiomethyl]-7-[2 -(Z)-(methoxyimino)-2-(2-tritylamino-4-thiazolyl)-acetamido] ceph-3-em-4-carboxylate iodide 4-Methoxybenzyl [6R,7R]-3-(chloromethyl)-7-[2-(Z)-(methoxyimino)- 2-(2-tritylamino-4-thiazolyl)acetamido]

-ceph-3-em-4-carboxylate (0.10 g, 0.12 mmol) in acetonitrile (5 ml) was treated with sodium iodide (0.02 g, 0.13 mmol) and 1-(t-butyloxycarbonyl)-2,6-dimethyl-4-thiopyridone (0.026 g, 0.12 mmol). The mixture was stirred for 2 h., then evaporated to dryness under reduced pressure. The residue was purified on silica gel 60 eluting with ethanol and dichloromethane (1:20) to give the title compound (0.051 g, 39%); $\upsilon_{max}$ ($CH_2Cl_2$) 1785, 1720, 1680, and 1610 $cm^{-1}$; $\delta_H$ ($CDCl_3$) 1.54 (9H, s), 2.65 (6H, s), 3.55 and 3.64 (2H, ABq, J 17.5Hz), 3.81 (3H, s), 3.96 (3H, s), 4.14 and 4.51 (2H, ABq, J 13Hz), 5.08 (1H, d, J 5Hz), 5.22 and 5.27 (2H, ABq, J 12Hz), 5.90 (1H, d, J 5Hz), 6.63 (1H, s), 6.91 (2H, m), 7.31 (18H, m), 7.48 (1H, m); m/z (F.A.B., 3-nitrobenzylalcohol, sodium acetate $MH^+$ 1012, $MNa^+$ 1034.

b) [6R,7R]-3-(1-Amino-2,6-dimethylpyridinium-4 -thiomethyl)-7-[2-(2-amino-4-thiazolyl)-2-(Z)- (methoxyimino)acetamido] ceph-3-em-4-carboxylate The product of Example 67(a) (0.051 g, 0.045 mmol) was treated with trifluoroacetic acid (1 ml) and stirred for 10 minutes. Toluene (1 ml) was added to the mixture which was then evaporated to dryness under reduced pressure. Purification of the residue on Diaion HP20SS resin eluting with acetone, water mixtures gave the title compound (0.009 g, 35%); $\upsilon_{max}$ (KBr) 1762, 1660 sh, and 1617 $cm^{-1}$; $\delta_H$ ($D_2O$) 2.66 (6H,s), 3.42 and 3.73 (2H, ABq, J 18Hz), 3.96 (3H, s), 4.03 and 4.48 (2H, ABq, J 14Hz), 5.12 (1H, d, J 5Hz), 5.74 (1H, d, J 5Hz), 6.99 (1H, s), and 7.50 (2H, s); m/z (F.A.B., thioglycerol) $MH^+$ 550.

We claim:

1. A compound of formula (I):

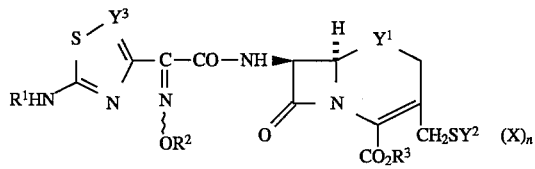

wherein:

$Y^1$ is sulphur, —SO—, or —$SO_2$—;

$R^1$ is hydrogen or an amino protecting group;

$R^2$ is ($C_{1-12}$)alkyl, ($C_{2-12}$)alkenyl, ($C_{2-12}$)alkynyl, ($C_{3-7}$)cycloalkyl, ($C_{5-8}$)cycloalkenyl, each of which is substituted by a phenyl group which may be unsubstituted or substituted up to 3 times with ($C_{1-6}$)alkoxy or hydroxy or a ($C_{1-6}$)alkylene dioxy group; and wherein each of the $R^2$ substituents hereinbefore defined, is also substituted by carboxyl or esterified carboxy; and $CO_2R^3$ is carboxy or a carboxylate anion, or the group $R^3$ is a readily removable carboxy protecting group;

$Y^2$ is a group of the formula:

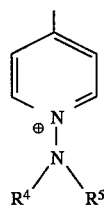

wherein the pyridinium group is unsubstituted or substituted at a ring carbon atom available for substitution by up to four substituents selected from ($C_{1-6}$)alkyl, and ($C_{1-6}$)alkoxy;

$R^4$ and $R^5$ which may be the same or different are selected from hydrogen, a group $R^6$, or a readily removable amino protecting group;

$R^6$ is ($C_{1-6}$)alkyl, ($C_{3-7}$)cycloalkyl, ($C_{2-6}$)alkenyl, ($C_{5-8}$)cycloalkenyl, ($C_{2-6}$)alkynyl, each of which may be unsubstituted or substituted by halogen, cyano, azido, nitro, carboxy, ($C_{1-6}$)alkoxycarbonyl, carbamoyl, mono- or di-($C_{1-6}$)alkylcarbamoyl, sulphono, sulphamoyl, mono- and di-($C_{1-6}$)alkylsulphamoyl, amino, mono- and di-($C_{1-6}$)alkylamino, acylamino, ($C_{1-6}$)alkoxycarbonylamino, hydroxy, ($C_{1-6}$)alkoxy, acyloxy, oxo, phenylcarbonyl, naphthylcarbonyl, heterocyclylcarbonyl, ($C_{1-6}$)alkylthio, ($C_{1-6}$)alkanesulphinyl, ($C_{1-6}$)alkanesulphonyl, phenyl, naphthyl or heterocyclyl; wherein the phenyl or naphthyl may be unsubstituted or substituted up to 5 times by halogen, ($C_{1-6}$)alkyl, phenyl, ($C_{1-6}$)alkoxy, hydroxy($C_{1-6}$)alkyl, mercapto($C_{1-6}$)alkyl, halo($C_{1-6}$)alkyl, mercapto, hydroxy, amino, mono- or di-($C_{1-6}$)alkylamino, nitro, carboxy, ($C_{1-6}$)alkoxycarbonyl, ($C_{1-6}$)alkoxycarbonyl($C_{1-6}$)alkyl, ($C_{1-6}$)alkylcarbonyloxy, formyl, or ($C_{1-6}$)alkylcarbonyl; wherein the heterocyclyl moiety may be unsubstituted or substituted up to 3 times by ($C_{1-6}$)alkyl, ($C_{1-6}$)alkoxy, ($C_{1-6}$)alkoxy-($C_{1-6}$)alkyl, halo($C_{1-6}$)alkyl, hydroxy, amino, mono- or di-($C_{1-6}$)alkylamino, acylamino, carboxy, carboxy salts, carboxy esters, carbamoyl, ($C_{1-6}$)alkoxycarbonyl, phenyloxycarbonyl, naphthyloxycarbonyl, ($C_{1-6}$)alkoxycarbonyl($C_{1-6}$)alkyl, oxo, or a phenyl or naphthyl group which is unsubstituted or substituted up to 5 times by halogen, ($C_{1-6}$)alkyl, phenyl, ($C_{1-6}$)alkoxy, hydroxy($C_{1-6}$)alkyl, mercapto($C_{1-6}$)alkyl, halo($C_{1-6}$)alkyl, mercapto, hydroxy, amino, mono- or di-($C_{1-6}$)alkylamino, nitro, carboxy, ($C_{1-6}$)alkoxycarbonyl, ($C_{1-6}$)alkoxycarbonyl($C_{1-6}$)alkyl, ($C_{1-6}$)alkylcarbonyloxy, formyl, or ($C_{1-6}$)alkylcarbonyl; and the heterocyclyl moiety is aromatic or non-aromatic, single or fused rings containing up to four heteroatoms in each ring selected from oxygen, nitrogen and sulphur;

$Y^3$ is nitrogen or —CH;

X is an inorganic or organic anion; and n is 0 or 1; with the proviso that when (i) $CO_2R^3$ is carboxylate n is O and (ii) $CO_2R^3$ is carboxy or the group $R^3$ is a readily removable carboxy protecting group, then n is 1 and the anion X is present in the appropriate stoichiometric proportion to balance the positive charge on the pyridinium group.

2. The compound according to claim 1 in which $R^2$ is a substituted ($C_{1-6}$)alkyl.

3. The compound according to claim 2 in which $R^2$ is methyl substituted by a phenyl group which is unsubstituted or substituted up to 3 times by ($C_{1-6}$)alkoxy or hydroxy.

4. The compound according to claim 3 in which the methyl is further substituted by a carboxy group.

5. The compound according to claim 2 in which $R^2$ is carboxy(3,4-dihydroxyphenyl)methyl or (methylenedioxy)benzyl.

6. The compound according to claim 3 in which $R^4$ and $R^5$ are each selected from hydrogen, methyl, ethyl, carboxymethyl, methoxyethyl, cyanomethyl, propargyl, 4-carboxybutan-1-yl, 2-amino-2-(methoxycarbonyl)ethyl, cyclopropylmethyl, propyl, cyclopentyl, prop-2-en-1-yl, butyl, hexyl, isopropyl, 2-hydroxyethyl, isoxazolylmethyl, thiazolylmethyl.

7. The compound according to claim 1 in which, in the group $Y^2$, the pyridinium ring is bonded to sulphur by a ring carbon atom which is α- or γ- to the pyridinium nitrogen.

8. A compound of formula (Ia) or a pharmaceutically acceptable salt or a pharmaceutically acceptable in vivo hydrolysable ester thereof:

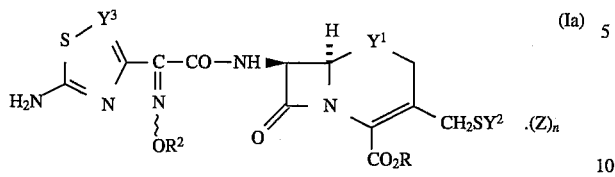

wherein $R^2$, $Y^1$, $Y^2$, $Y^3$ and n are as defined in claim 1, with the proviso that $R^4$ and $R^5$ is not a readily removable amino protecting group; the group $CO_2R$ is carboxy or a carboxylate anion and Z is a pharmaceutically acceptable inorganic or organic anion present in the appropriate stoichiometric proportion to balance the positive charge on the pyridinium ring of the group $Y^2$.

9. A compound of formula (I):

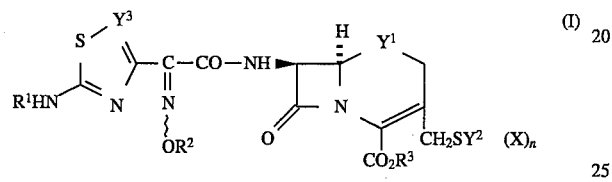

wherein:

$Y^1$ is sulphur, —SO—, or —$SO_2$;

$R^1$ is hydrogen or an amino protecting group;

$R^2$ is hydrogen, $(C_{1-12})$alkyl, $(C_{2-12})$alkenyl, $(C_{2-12})$alkynyl, $(C_{3-7})$cycloalkyl, $(C_{5-8})$cycloalkenyl, each of which may be unsubstituted or substituted by carboxyl, esterified carboxy, hydroxy, alkoxy, cyano, carbamoyl, N-substituted carbamoyl, phenyloxy, naphthyloxy, phenylalkoxy, naphthlalkoxy, mercapto, alkylthio, phenylthio, naphthylthio, amino, substituted amino, halogen, nitro, azido, formyl, acyl, acyloxy, pthalimido, acylamino, alkoxycarbonylamino, phenalkoxy-carbonylamino or naphthalkoxy-carbonylamino;

$CO_2R^3$ is carboxy or a carboxylate anion, or the group $R^3$ is a readily removable carboxy protecting group;

$Y^2$ is a group of the formula:

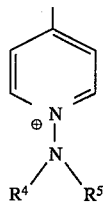

wherein the pyridinium group is unsubstituted or substituted by up to four substituents selected from $(C_{1-6})$alkyl and $(C_{1-6})$alkoxy;

$R^4$ and $R^5$ which may be the same or different are selected from hydrogen, a group $R^6$, or a readily removable amino protecting group; or $R^6$ is $(C_{1-6})$alkyl, $(C_{3-7})$cycloalkyl, $(C_{2-6})$alkenyl, $(C_{5-8})$cycloalkenyl, $(C_{2-6})$alkynyl, each of which may be unsubstituted or substituted by halogen, cyano, azido, nitro, carboxy, $(C_{1-6})$alkoxycarbonyl, carbamoyl, mono- or di-$(C_{1-6})$alkylcarbamoyl, sulphono, sulphamoyl, mono- and di-$(C_{1-6})$alkylsulphamoyl, amino, mono- and di-$(C_{1-6})$alkylamino, acylamino, $(C_{1-6})$alkoxycarbonylamino, hydroxy, $(C_{1-6})$alkoxy, acyloxy, oxo, phenylcarbonyl, naphthylcarbonyl, heterocylcylcarbonyl, $(C_{1-6})$alkylthio, $(C_{1-6})$alkanesulphinyl, $(C_{1-6})$alkanesulphonyl, phenyl, naphthyl, or heterocyclyl; wherein the phenyl or naphthyl group may be unsubstituted or substituted up to 5 times by halogen, $(C_{1-6})$alkyl, phenyl, $(C_{1-6})$alkoxy, hydroxy$(C_{1-6})$alkyl, mercapto$(C_{1-6})$alkyl, halo$(C_{1-6})$alkyl, mercapto, hydroxy, amino, mono- or di-$(C_{1-6})$alkylamino, nitro, carboxy, $(C_{1-6})$alkoxycarbonyl, $(C_{1-6})$alkoxycarbonyl$(C_{1-6})$alkyl, $(C_{1-6})$alkylcarbonyloxy, formyl, or $(C_{1-6})$alkylcarbonyl; wherein the heterocyclyl moiety may be unsubstituted or substituted up to 3 times by $(C_{1-6})$alkyl, $(C_{1-6})$alkoxy, $(C_{1-6})$alkoxy$(C_{1-6})$alkyl, halo$(C_{1-6})$alkyl, hydroxy, amino, mono- or di-$(C_{1-6})$alkylamino, acylamino, carboxy, carboxy salts, carboxy esters, carbamoyl, $(C_{1-6})$alkoxycarbonyl, phenyloxycarbonyl, naphthyloxycarbonyl, $(C_{1-6})$alkoxycarbonyl$(C_{1-6})$alkyl, oxo, or a phenyl or naphthyl group which is unsubstituted or substituted up to 5 times by halogen, $(C_{1-6})$alkyl, phenyl, $(C_{1-6})$alkoxy, hydroxy$(C_{1-6})$-alkyl, mercapto$(C_{1-6})$alkyl, halo$(C_{1-6})$alkyl, mercapto, hydroxy, amino, mono- or di-$(C_{1-6})$alkylamino, nitro, carboxy, $(C_{1-6})$alkoxycarbonyl; $(C_{1-6})$alkoxycarbonyl$(C_{1-6})$alkyl, $(C_{1-6})$alkylcarbonyloxy, formyl, or $(C_{1-6})$alkylcarbonyl; and wherein the heterocyclyl moiety is aromatic or non-aromatic, single or fused rings containing up to four heteroatoms in each ring selected from oxygen, nitrogen and sulphur; or $Y^3$ is nitrogen or CH;

X is an inorganic or organic anion; and n is 0 or 1; with the proviso that when (i) $CO_2R^3$ is carboxylate, n is 0, and (ii) $CO_2R^3$ is carboxy or the group $R^3$ is a readily removable carboxy protecting group, then n is 1 and the anion X is present in the appropriate stoichiometric proportion to balance the positive charge on the pyridinium group.

10. A compound of formula (II):

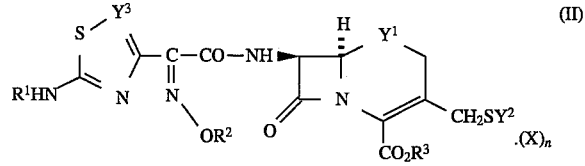

wherein $R^1$, $R^2$, $R^3$, X, $Y^1$, $Y^2$, $Y^3$ and n are as defined with respect to formula (I) according to claim 1.

11. A compound of the formula (II):

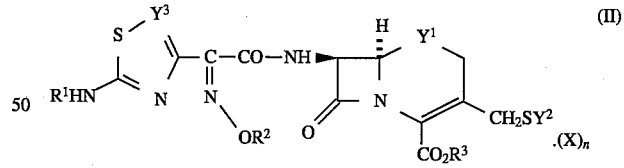

wherein $R^1$, $R^2$, $R^3$, X, Y, $Y^2$, $Y^3$ and n are as defined with respect to formula (I) according to claim 9.

12. A pharmaceutical composition comprising a compound of formula (Ia) as defined in claim 8 or a pharmaceutically acceptable salt or in vivo hydrolysable ester thereof, in combination with a pharmaceutically acceptable excipient or diluent.

13. The pharmaceutical composition as claimed in claim 12 further comprising a β-lactamase inhibitor.

14. A method of treating bacterial infections in humans and animals which method comprises administering a therapeutically effective amount of a compound of formula (Ia) as defined in claim 8 or a pharmaceutically acceptable salt or in vivo hydrolysable ester thereof to a patient in need thereof.

15. A compound of formula (Ia) or a pharmaceutically acceptable salt or a pharmaceutically acceptable in vivo hydrolysable ester thereof:

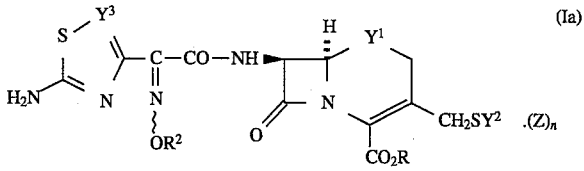

wherein $R^2$, $Y^1$, $Y^2$, $Y^3$ and n are as defined in claim 9, with the proviso that $R^4$ and $R^5$ is not a readily removable amino protecting group; the group $CO_2R$ is carboxy or a carboxylate anion and Z is a pharmaceutically acceptable inorganic or organic anion present in the appropriate stoichiometric proportion to balance the positive charge on the pyridinium ring of the group $Y^2$.

16. The compound according to claim 9 in which $R^2$ is a substituted or unsubstitued $(C_{1-6})$alkyl, substituted or unsubstitued $(C_{3-7})$alkyl, or hydrogen.

17. The compound according to claim 16 wherein $R^2$ is methyl substituted or unsubstituted by a carboxy group.

18. The compound according to claim 16 wherein $R^2$ is hydrogen, methyl, 1-carboxy-1-methylethyl, cyclopentyl, or ethyl.

19. The compound according to claim 9 wherein $R^4$ and $R^5$ is each selected from hydrogen, methyl, ethyl, carboxymethyl, methoxyethyl, cyanomethyl, propargyl, 4-carboxybutan-1-yl, 2-amino-2-(methoxycarbonyl)ethyl, cyclopropylmethyl, propyl, cyclopentyl, prop-2-en-1-yl, butyl, hexyl, isopropyl, 2-hydroxyethyl, pyridyl, isoxazolylmethyl, thiazolylmethyl, chloropyridinyl, pyrazinyl, imidazolinyl, benzopyrazidinyl, acetyl, benzoyl, 3,4-dihydroxybenzoyl, 4-nitrobenzoyl, 4-methoxybenzoyl, 4-carboxybenzoyl, 4-aminobenzoyl, 2-furanoyl, 3,4-dihydroxycinnamoyl, carbamoyl, N-methylcarbamoyl and t-butyoxycarbonyl; or the groups $R^4$ and $R^5$ together with the nitrogen to which they are attached form a piperazinyl, triazolyl, pyrrolidinyl or piperidinyl group, each of which may be substituted or unsubstituted; or $R^4$ and $R^5$ together form an isopropylidene group.

20. A pharmaceutical composition comprising a compound of formula (Ia) as defined in claim 15 or a pharmaceutically acceptable salt or in vivo hydrolysable ester thereof, in combination with a pharmaceutically acceptable excipient or diluent.

21. The pharmaceutical composition according to claim 20 in which the compound is [6R,7R]-7-[2-(2-Amino-4-thiazolyl)-2-(Z)-(methoxyimino)acetamido]-3-[1-(methylamino)-pyridinium-4-thiomethyl]ceph-3-em-4-carboxylic acid or pharmacuetically acceptable salts thereof.

22. A method of treating bacterial infections in humans and animals which method comprises administering a therapeutically effective amount of a compound of formula (Ia) as defined in claim 9 or a pharmaceutically acceptable salt or in vivo hydrolysable ester thereof to a patient in need thereof.

23. A compound and pharmaceutically acceptable salts and in-vivo hydrolysable esters thereof, selected from the group consisting of:

[6R, 7R]-7-[2-(2-Amino-4-thiazolyl)-2-(Z)-[(R,S)-carboxy(3,4-dihydroxyphenyl)methyloxyimino]acetamido] -3-[1-(methylamino(pyridinium-4-thiomethyl]ceph-3-em-4-carboxylate;

6R, 7R]-7-[2-(2-Amino-4-thiazolyl)-2-(Z)-[(R)-carboxy(3,4-dihydroxyphenyl)methyloxyimino]acetamido] -3-[1-(methylamino(pyridinium-4-thiomethyl]ceph-3-em-4-carboxylate;

[6R, 7R]-3-[1-Aminopyridinium-4-thiomethyl] -7-[2-(2-amino-4-thiazolyl)-2-(Z)-[(R, S)-carboxy(3,4-dihydroxyphenyl)methyloxyimino]acetamido]ceph-3-em-4-carboxylate;

[6R,7R]-3-[1-Aminopyridinium-4-thiomethyl] -7-[2-(2-amino-4-thiazolyl)-2-(Z)-[(S)-carboxy (3,4-dihydroxyphenyl)methyloxyimino]acetamido]ceph-3-em-4-carboxylate;

[6R, 7R]-3-[1-Aminopyridinium-4-thiomethyl]-7-[2-(2-amino-4-thiazolyl)-2-(Z)-[(R)-carboxy(3,4-dihydroxyphenyl)methyloxyimino]acetamido]ceph-3-em-4-carboxylate;

[6R, 7R]-7-[2-(2-Amino-4-thiazolyl)-2-(Z)-[3,4-(methylenedioxy)benzyloxyimino]acetamido]-3-[1-(methylamino(pyridinium-4-thiomethyl)ceph-3-em-4-carboxylate;

[6R, 7R]-7-[2-(2-Amino-4-thiazolyl)-2-(Z)-(methoxyimino)acetamido] -3-[1-(dimethylamino(pyridinium-4-thiomethyl]-ceph-3-em-4-carboxylate;

[6R, 7R]-7-[2-(2-Amino-4-thiazolyl)-2-(Z)-(1-carboxy-1-methylethoxyimino)acetamido]-3-[1-(methylamino(pyridinium-4-thiomethyl]ceph-3-em-4-carboxylate;

[6R, 7R]-3-(1-Aminopyridinium-4-thiomethyl)-7-[2-(2-amino-4-thiazolyl)-2-(,Z)-(methoxyimino)acetamido] ceph- 3-em-4-carboxylate;

[6R,7R]-[2-(2-Amino-4-thiazolyl)-2-(Z)-(methoxyimino)acetamido] -3-[1-(carboxymethylamino)pyridinium-4-thiomethyl]ceph-3-em-4-carboxylate;

[6R, 7R]-7-[2-(2-Amino-4-thiazolyl)-2-(Z)-(methoxyimino)acetamido] -3-[1-(ethylamino(pyridinium-4-thiomethyl]ceph-3-em-4-carboxylate;

6R, 7R]-7-[2-(2-Amino-4-thiazolyl)-2-(Z)-(cyclopentyloxyimino)acetamido] -3-[1-(methylamino(pyridinium-4-thiomethyl]ceph-3-em-4-carboxylate;

[6R, 7R]-7-[2-(2-Amino-4-thiazolyl)-2-(Z)-(hydroxyimino)acetamido] -3-[1-(methylamino(pyridinium-4-thiomethyl]ceph-3-em-4-carboxylate;

[6R, 7R]-7-[2-(2-Amino-4-thiazolyl)-2-(Z)-(methoxyimino)acetamido] -3-[1-(4-carboxybutan-1-yl)aminopyridinium-4-thiomethyl]ceph-3-em-4-carboxylate;

[6R, 7R]-7-[2-(2-Amino-4-thiazolyl)-2-(Z)-(ethoxyimino)acetamido]-3-[1-(methylamino(pyridinium-4-thiomethyl]ceph-3-era-4-carboxylate;

[6R,7R]-3-[1-[(2S)-2-Amino-2-(methoxycarbonyl)ethylamino] pyridinium-4-thiomethyl]-7-[2-(2-amino-4-thiazolyl)-2-(Z)-(methoxyimino)acetamido]ceph-3-em-4-carboxylate;

[6R,7R]-7-[2-(2-Amino-4-thiazolyl)-2-(Z)-(methoxyimino)acetamido]-3-[1-(cyclopropylmethylamino)pyridinium-4-thiomethyl]ceph-3-em-4-carboxylate;

[6R, 7R]-3-(1-Aminopyridinium-4-thiomethyl)-7-[2-amino-4-thiazolyl)-2-(Z)-(methoxyimino)acetamido]ceph-3-em-4-carboxylate;

[6R, 7R]-7-[2-(2-Amino-4-thiazolyl)-2-(Z)-(methoxyimino)acetamido]-3-[1-(propylamino(pyridinium-4-thiomethyl]-ceph-3-em-4-carboxylate;

[6R, 7R]-7-[2-(2-Amino-4-thiazo 1 yl)-2-(Z)-(methoxyimino)acetamido] -3-[1-(cyclopentylamino(pyridinium-4-thiomethyl]ceph-3-em-4-carboxylate;

[6R, 7R]-7-[2-(2-Amino-4-thiazolyl)-2-(Z)-(methoxyimino)acetamido] -3-[1-(prop-2-en-1-yl)aminopyridinium-4-thiomethyl]ceph-3-em-4-carboxylate;

[6R, 7R]-7-[2-(2-Amino-4-thiazolyl)-2-(Z)-(methoxyimino)acetamido] -3-[1-butylaminopyridinium-4-thiomethyl] ceph-3-em-4-carboxylate;

[6R,7R]-7-[2-(2-Amino-4-thiazolyl)-2-(Z)(methoxyimino)acetamido]-3-[1-(hexylamino)pyridinium-4-thiomethyl] ceph-3-em-4-carboxylate;

[6R,7R]-7-[2-(2-Amino-4-thiazolyl)-2-(Z)-(methoxyimino) acetamido]-3-[1-(1-isopropyl)aminopyridinium-4-thiomethyl] ceph-3-em-4-carboxylate;

[6R, 7R]-7-[2-(2-Amino-4-thiazolyl)-2-(Z)-(methoxyimino)acetamido] -2-[1-[(2-hydroxyethyl)amino] pyridinium-4-thiomethyl]ceph-3-em-4-carboxylate;

[6R, 7R]-7-[2-(2-Amino-4-thiazolyl)-2-(Z)-(methoxyimino)acetamido] -3-[1-(3,5-dimethylisoxazol-4-yl)methylaminopyridinium-4-thiomethyl]ceph-3-em-4-carboxylate;

[6R, 7R]-7-[2-(5-Amino-1,2,4-thiadiazol-3-yl)-2-(Z)-(methoxyimino)acetamido]-3-[1-(methylamino)pyridinium-4-thiomethyl]ceph-3-em-4-carboxylate;

[6R,7R]-3-(1-Amino-3-methoxy-2-methylpyridinium-4-thiomethyl)-7-[2-(2-amino-4-thiazolyl)-2-(Z)-(methoxyimino)acetamido] -ceph-3-em-4-carboxylate;

[6R, 7R]-7-[2-(2-Amino-4-thiazolyl)-2-(Z)-(methoxyimino)acetamido] -3-[1-[(2-methoxyethyl)amino] pyridinium-4-thiomethyl]ceph-3-em-4-carboxylate;

6R, 7R]-7-[2-(2-Amino-4-thiazolyl)-2-(Z)-(methoxyimino)acetamido] -3-[1-[(2-methyl-4-thiazolyl)m ethylamino]pyridinium-4-thiomethyl]ceph-3-em-4-carboxylate;

[6R, 7R]-7-[2-(2-Amino-4-thiazolyl)-2-(Z)-(methoxyimino)acetamido] -3-[1-[(cyanomethyl)amino] pyridinium-4-thiomethyl]ceph-3-em-4-carboxylate;

[6R, 7R]-7-[2-(2-Amino-4-thiazolyl)-2-(Z)-(methoxyimino)acetamido] -3-[1-(prop-2-yn-1-ylamino)pyridinium-4-thiomethyl]ceph-3-em-4-carboxylate;

[6R, 7R]-7-[2-(2-Amino-4-thiazolyl)-2-(Z)-(methoximino)acetamido]-3-[1-(methylamino(pyridinium-4-thiomethyl]ceph-3-em-4-carboxylate-1-oxide; and

[6R, 7R]-3-(1-Amino-2,6-dimethylpyridinium-4-thiomethyl)- 7-[2-(2-amino-4-thiazolyl)-2-(Z)-(methoxyimino)acetamido]ceph-3-em-4-carboxylate.

24. The compound [6R,7R]-7-[2-(2-Amino-4-thiazolyl)-2-(Z)-[(R)-carboxy(3,4-dihydroxyphenyl)methyloxyimino] acetamido]-3-[1-(methylamino)pyridinium-4 -thiomethyl]ceph-3-em-4-carboxylate or pharmaceutically acceptable salts thereof.

25. The pharmaceutical composition according to claim 12 in which the compound is [6R,7R]-7-[2-(2-Amino-4-thiazolyl)-2-(Z)-[(R)-carboxy(3,4-dihydroxyphenyl)methyloxyimino] acetamido]-3-[1-(methylamino)pyridinium-4-thiomethyl]ceph-3-em-4-carboxylate or pharmaceutically acceptable salts thereof.

26. The compound [6R,7R]-7-[2-(2-Amino-4-thiazolyl)-2-(Z)-(methoxyimino)acetamido]-3-[1-(methylamino)pyridinium- 4-thiomethyl]ceph-3-em-4-carboxylic acid or pharmaceutically acceptable salts thereof.

27. The compound according to claim 3 wherein the phenyl group is 3,4-dihydroxyphenyl, 3,4-diacetoxy or methylenedioxyphenyl.

* * * * *